US008476227B2

(12) United States Patent
Kaplan et al.

(10) Patent No.: US 8,476,227 B2
(45) Date of Patent: Jul. 2, 2013

(54) METHODS OF ACTIVATING A MELANOCORTIN-4 RECEPTOR PATHWAY IN OBESE SUBJECTS

(75) Inventors: Lee M. Kaplan, Wellesley, MA (US); Nicholas Stylopoulos, Boston, MA (US); Jason L. Harris, Mason, OH (US)

(73) Assignees: Ethicon Endo-Surgery, Inc., Cincinnati, OH (US); The General Hospital Corporation, Boston, MA (US)

(*) Notice: Subject to any disclaimer, the term of this patent is extended or adjusted under 35 U.S.C. 154(b) by 0 days.

(21) Appl. No.: 12/980,635

(22) Filed: Dec. 29, 2010

(65) Prior Publication Data

US 2011/0263490 A1    Oct. 27, 2011

Related U.S. Application Data

(60) Provisional application No. 61/297,483, filed on Jan. 22, 2010.

(51) Int. Cl.
*A61K 38/00* (2006.01)
*A61P 3/04* (2006.01)

(52) U.S. Cl.
USPC .......................................................... 514/4.8

(58) Field of Classification Search
None
See application file for complete search history.

(56) References Cited

U.S. PATENT DOCUMENTS

| | | | |
|---|---|---|---|
| 4,498,843 A | 2/1985 | Schneider et al. |
| 4,578,770 A | 3/1986 | Mitani |
| 4,596,792 A | 6/1986 | Vyas |
| 4,599,230 A | 7/1986 | Milich et al. |
| 4,599,231 A | 7/1986 | Milich et al. |
| 4,601,903 A | 7/1986 | Frasch |
| 4,608,251 A | 8/1986 | Mia |
| 4,772,631 A | 9/1988 | Holloway et al. |
| 4,927,836 A | 5/1990 | Holloway et al. |
| 4,937,267 A | 6/1990 | Holloway et al. |
| 4,978,338 A | 12/1990 | Melsky et al. |
| 5,434,184 A | 7/1995 | Holloway et al. |
| 5,453,270 A | 9/1995 | Bills |
| 5,486,359 A | 1/1996 | Caplan et al. |
| 5,731,408 A | 3/1998 | Hadley et al. |
| 5,736,396 A | 4/1998 | Bruder et al. |
| 5,789,654 A | 8/1998 | Lowell et al. |
| 5,811,094 A | 9/1998 | Caplan et al. |
| 5,827,735 A | 10/1998 | Young et al. |
| 5,827,740 A | 10/1998 | Pittenger |
| 5,837,539 A | 11/1998 | Caplan et al. |
| 5,837,670 A | 11/1998 | Hartshorn |
| 5,843,723 A | 12/1998 | Dubensky, Jr. et al. |
| 5,911,992 A | 6/1999 | Braswell et al. |
| 6,069,147 A | 5/2000 | Williams et al. |
| 6,071,747 A | 6/2000 | Strosberg et al. |
| 6,072,100 A | 6/2000 | Mooney et al. |
| 6,197,580 B1 | 3/2001 | Susulic et al. |
| 6,207,878 B1 | 3/2001 | Campbell et al. |
| 6,224,873 B1 | 5/2001 | Jones |
| 6,451,336 B2 | 9/2002 | Sugano et al. |
| 6,475,530 B1 | 11/2002 | Kuhrts |
| 6,532,386 B2 | 3/2003 | Sun et al. |
| 6,565,847 B1 | 5/2003 | Gorsek |
| 6,602,694 B1 | 8/2003 | Albrandt et al. |
| 6,605,297 B2 | 8/2003 | Nadachi et al. |
| 6,620,594 B1 | 9/2003 | Giacobino et al. |
| 6,645,229 B2 | 11/2003 | Matsumura et al. |
| 6,908,987 B2 | 6/2005 | Spiegelman et al. |
| 6,922,590 B1 | 7/2005 | Whitehurst |
| 6,927,288 B2 | 8/2005 | Ito |
| 6,983,753 B1 | 1/2006 | Lenhard et al. |
| 7,060,437 B1 | 6/2006 | Kopchick |
| 7,091,006 B2 | 8/2006 | Spiegelman et al. |
| 7,135,611 B2 | 11/2006 | MacDougald et al. |
| 7,191,007 B2 | 3/2007 | Desai et al. |
| 7,250,283 B2 | 7/2007 | Spiegelman et al. |
| 7,264,602 B1 | 9/2007 | Longsworth |
| 7,300,409 B2 | 11/2007 | Kopanic, Jr. et al. |
| 7,367,341 B2 | 5/2008 | Anderson et al. |
| 7,396,642 B2 | 7/2008 | Yamaoka et al. |
| 7,440,806 B1 | 10/2008 | Whitehurst et al. |
| 7,476,406 B1 | 1/2009 | Smidt |

(Continued)

FOREIGN PATENT DOCUMENTS

| | | |
|---|---|---|
| EP | 377695 A1 | 7/1990 |
| EP | 1060728 A1 | 12/2000 |

(Continued)

OTHER PUBLICATIONS

Boyce RS and Duhl DM. Curr. Opin. Investig. Drugs, 5(10):1063-1071, Oct. 2004.*
Ste Marie L et al., PNAS 97(22):12339-44, Oct. 2000.*
Balthasar N, et al. Cell 123:493-505, Nov. 4, 2005.*
van Marken Lichtenbelt W, et al. NEJM 360:1500-1508, 2009.*
"3m CoTran® 9702 Membrane" Brochure 2009 (2 pages).
"3m CoTran® 9705 Membrane" Brochure 2009 (2 pages).
"3m CoTran® 9706 Membrane" Brochure 2009 (2 pages).
"3m CoTran® 9707 Membrane" Brochure 2009 (2 pages).
"3m CoTran® 9712 Membrane" Brochure 2009 (2 pages).
"3m CoTran® 9715 Membrane" Brochure 2009 (2 pages).
"3m CoTran® 9716 Membrane" Brochure 2009 (2 pages).
"3m CoTran® 9728 Membrane" Brochure 2009 (2 pages).
"3M CoTran® Membranes" copyright 2010 at 3M website.

(Continued)

*Primary Examiner* — Robert Landsman
(74) *Attorney, Agent, or Firm* — Nutter McClennen & Fish LLP

(57) ABSTRACT

Methods and therapeutics are provided for treating metabolic disorders by activation of melanocortin signaling pathways. Generally, the methods and therapeutics can induce activation of melanocortin receptor signaling to increase energy expenditure and induce weight loss. In one embodiment, a method for performing a diagnostic procedure can be chosen, energy expenditure then assess in light of the diagnostic procedure and a definitive procedure(s) can be selected dependent on the outcome of the energy assessment. In another embodiment, a diagnostic procedure can be chosen to activate melanocortin receptor pathways, energy expenditure can be assessed and a definitive procedure(s) can be chosen that selectively and optimally activate melanocortin receptor pathways.

20 Claims, 25 Drawing Sheets

U.S. PATENT DOCUMENTS

| | | | |
|---|---|---|---|
| 7,526,061 B2 | 4/2009 | Kobayashi | |
| 7,576,052 B2 | 8/2009 | Kahn et al. | |
| 7,599,736 B2 | 10/2009 | DiLorenzo | |
| 7,599,743 B2 | 10/2009 | Hassler, Jr. et al. | |
| 7,599,744 B2 | 10/2009 | Giordano et al. | |
| 7,647,112 B2 | 1/2010 | Tracey et al. | |
| 2001/0032337 A1 | 10/2001 | Forman | |
| 2003/0082168 A1 | 5/2003 | Yegorova | |
| 2003/0104081 A1 | 6/2003 | Rombi | |
| 2003/0119775 A1 | 6/2003 | Surwit et al. | |
| 2003/0212016 A1 | 11/2003 | Gimeno et al. | |
| 2003/0220238 A1 | 11/2003 | Adams et al. | |
| 2004/0077556 A1 | 4/2004 | Chinery | |
| 2005/0043524 A1 | 2/2005 | Bhanot et al. | |
| 2005/0045498 A1 | 3/2005 | Purcell et al. | |
| 2005/0080026 A1 | 4/2005 | Steuernagel et al. | |
| 2005/0136429 A1 | 6/2005 | Guarente et al. | |
| 2005/0169839 A1 | 8/2005 | Fong | |
| 2005/0177067 A1 | 8/2005 | Tracey et al. | |
| 2005/0261223 A1 | 11/2005 | Czech et al. | |
| 2005/0277998 A1 | 12/2005 | Tracey et al. | |
| 2005/0288740 A1 | 12/2005 | Hassler et al. | |
| 2006/0008540 A1 | 1/2006 | Xiu | |
| 2006/0014178 A1 | 1/2006 | Whitson et al. | |
| 2006/0084637 A1 | 4/2006 | Alemany | |
| 2006/0121158 A1 | 6/2006 | Ferruzzi et al. | |
| 2006/0195146 A1 | 8/2006 | Tracey et al. | |
| 2006/0195153 A1 | 8/2006 | DiUbaldi et al. | |
| 2006/0204599 A1 | 9/2006 | Wheat | |
| 2006/0223104 A1 | 10/2006 | Kahn et al. | |
| 2007/0082843 A1 | 4/2007 | Stojanovic-Susulic | |
| 2007/0185541 A1 | 8/2007 | DiUbaldi et al. | |
| 2007/0244375 A1* | 10/2007 | Jenkins et al. | 600/301 |
| 2008/0046012 A1 | 2/2008 | Covalin et al. | |
| 2008/0080026 A1 | 4/2008 | Mestha et al. | |
| 2008/0132962 A1 | 6/2008 | DiUbaldi et al. | |
| 2008/0138449 A1 | 6/2008 | Heuer et al. | |
| 2008/0139875 A1 | 6/2008 | Tracey et al. | |
| 2008/0147146 A1 | 6/2008 | Wahlgren et al. | |
| 2008/0200376 A1* | 8/2008 | MacCoss et al. | 514/12 |
| 2008/0293830 A1 | 11/2008 | Katagiri et al. | |
| 2009/0012555 A1 | 1/2009 | Makower | |
| 2009/0018594 A1 | 1/2009 | Laufer et al. | |
| 2009/0024144 A1 | 1/2009 | Zeiner et al. | |
| 2009/0054487 A1 | 2/2009 | Kolonics et al. | |
| 2009/0062193 A1 | 3/2009 | Weyer et al. | |
| 2009/0081715 A1 | 3/2009 | Burns-Guydish et al. | |
| 2009/0093858 A1 | 4/2009 | DiUbaldi | |
| 2009/0132018 A1 | 5/2009 | DiUbaldi et al. | |
| 2009/0149918 A1 | 6/2009 | Krulevitch et al. | |
| 2009/0157149 A1 | 6/2009 | Wahlgren et al. | |
| 2009/0171375 A1 | 7/2009 | Coe et al. | |
| 2009/0202387 A1 | 8/2009 | Dlugos, Jr. et al. | |
| 2009/0202659 A1 | 8/2009 | Gimble | |
| 2009/0204131 A1 | 8/2009 | Ortiz et al. | |
| 2010/0056948 A1 | 3/2010 | Hornby et al. | |
| 2010/0161001 A1 | 6/2010 | DiUbaldi et al. | |
| 2010/0161005 A1 | 6/2010 | Wahlgren et al. | |
| 2010/0239648 A1 | 9/2010 | Smith et al. | |
| 2010/0249677 A1 | 9/2010 | DiUbaldi et al. | |
| 2010/0312295 A1 | 12/2010 | Vase et al. | |
| 2011/0152987 A1 | 6/2011 | Wahlgren et al. | |

FOREIGN PATENT DOCUMENTS

| | | |
|---|---|---|
| EP | 1172113 A1 | 1/2002 |
| JP | 2001-259047 A | 9/2001 |
| JP | 5-21940 A | 1/2005 |
| WO | 8911701 A1 | 11/1989 |
| WO | 9100730 | 1/1991 |
| WO | 9322277 | 11/1993 |
| WO | 9506411 | 3/1995 |
| WO | 9814200 | 4/1998 |
| WO | 9845313 | 10/1998 |
| WO | 9856397 | 12/1998 |
| WO | 9900123 | 1/1999 |
| WO | 0155109 A1 | 8/2001 |
| WO | 0170337 A1 | 9/2001 |
| WO | 0170708 A1 | 9/2001 |
| WO | 0212887 A2 | 2/2002 |
| WO | 0215909 A1 | 2/2002 |
| WO | 0218327 A2 | 3/2002 |
| WO | 02059095 A1 | 8/2002 |
| WO | 02059107 A1 | 8/2002 |
| WO | 02059108 A1 | 8/2002 |
| WO | 02059117 A1 | 8/2002 |
| WO | 02067869 A2 | 9/2002 |
| WO | 02068387 A2 | 9/2002 |
| WO | 02068388 A2 | 9/2002 |
| WO | 02081443 A1 | 10/2002 |
| WO | 02085925 A2 | 10/2002 |
| WO | 03006620 A2 | 1/2003 |
| WO | 03007949 A1 | 1/2003 |
| WO | 03009847 A1 | 2/2003 |
| WO | 03009850 A1 | 2/2003 |
| WO | 03026576 A2 | 4/2003 |
| WO | 2004078716 A1 | 9/2004 |
| WO | 2004078717 A1 | 9/2004 |
| WO | 2004087159 A1 | 10/2004 |
| WO | 2005033254 A1 | 4/2005 |
| WO | 2005040109 A1 | 5/2005 |
| WO | 2005047251 A1 | 5/2005 |
| WO | 2005077935 A1 | 8/2005 |
| WO | 2006019787 A2 | 2/2006 |
| WO | 2006020277 A2 | 2/2006 |
| WO | 2006072393 A2 | 7/2006 |
| WO | 2007015157 A2 | 2/2007 |
| WO | 2007015162 A1 | 2/2007 |
| WO | 2007041052 A2 | 4/2007 |
| WO | 2007041061 A2 | 4/2007 |
| WO | 2007047496 A2 | 4/2007 |
| WO | 2008063330 A2 | 5/2008 |
| WO | 2008087190 A2 | 7/2008 |
| WO | 2009008991 A2 | 1/2009 |
| WO | 2009067501 A2 | 5/2009 |
| WO | 2009097542 A2 | 8/2009 |
| WO | 2009117415 A2 | 9/2009 |

OTHER PUBLICATIONS

"Shining a light on disease—tracking light-emitting bacteria during infection," Society for General Microbiology, Sep. 9, 2009 (1 page).

Accornero et al., "Selective Activation of peripheral nerve fibre groups of different diameter by triangular shaped stimulus pulses," J Physiol, 1977, 273:539-560.

Bakshi RK et al., Bioorg Med Chem Lett. Jul. 15, 2005;15(14):3430-3.

Berkner et al. (1988) BioTechniques 6:616.

Bing, C. et al., "Hyperphagia in cold-exposed rats is accompanied by decreased plasma leptin but unchanged hypothamalic NPY," Am J Physiol Regulatory Integrative Comp Physiol 274:62-68, 1998.

Birks, R.I., "Regulation by patterned preganglionic neural activity of transmitter stores in a sympathetic ganglion," J Physiol, 1978, 280: 559-572.

Boshart et al. (1985) Cell 41:521-530.

Bostock et al., "Velocity recovery cycles of C fibres innervating human skin," J Physiol, 2003, 553.2, 649-663.

Bouillaud et al., "Increased Level of mRNA for the Uncouping Protein in Brown Adipose Tissue of Rats during Thermogenesis Induced by Cold Exposure or Norepinephrine Infusion," The Journal of Biological Chemistry V. 259, No. 18, p. 11583-11586 (1984).

Bredenbeek, P. J., et al., J. Virol. (1993) 67: 6439-6446.

Bugajksi AJ et al., "Effect of long-term vagal stimulation on food intake and body weight during diet induced obesity in rats," J Phys Pharm, 58 (Supp 1): 5-12, (Mar. 2007).

Cannon, B. et al., "Brown Adipose Tissue: Function and Physiological Significance," Physiol Rev., 2004: 84: 277-359.

Capecchi (1980) Cell 22:479-488.

Cassiede P., et al., J. Bone Miner. Res. (1996) 11(9): 1264-1273.

Cheneval et al. (1991) Proc. Natl. Acad. Sci. USA 88:8465-9.

Chu et al.. (1981) Gene 13:197.

Clark et al. J. Drug. Target 7, 269-83 (1999).

Collins, Si, "The cervical sympathetic nerves in surgery of the neck," Otolaryngol Head Neck Surg, 1991, 105:544.

Crago et al., "The choice of pulse duration for chronic electrical stimulation via surface, nerve, and intramuscular electrodes," Ann Biomed Eng, 1974, 2: 252-264.
Current Protocols in Molecular Biology, Ausubel et al. (eds.) Greene Publishing Associates, (1989), Sections 9.10-9.14.
Davidson, B. L., et al., Nature Genetics (1993) 3: 219-223.
Davis et al. (1986) Basic Methods in Molecular Biology, Elsevier.
Douglas, J., et al., Nature Biotech. (1999) 17: 470-475.
Drazen, D. L. & Woods, S. C., Curr. Opin. Clin. Nutr. Metab. Care 2003; 6:621-629.
Dull, T., et al., J. Virol. (1998) 72: 8463-8471.
Ekblom et al., Ann. N.Y. Acad. Sci., 857:194-211, 1998.
Felgner et al. (1987) Proc. Natl. Acad. Sci. USA 84:7413 7417.
Flaim et al. 1976, "Functional and Anatomical Characteristics of the Nerve-Brown Adipose Interation in the Rat," Pfluegers Arch. 365, 9-14.
Foster et al., "Heterogeneity of the Sympathetic Innervation of Rat Interscapular Brown Adipose Tissue via Intercostal Nerves," Can J Physiol. Pharmacol. Jun. 1982;60(6):747-54.
Frolov, I., et al., Proc. Natl. Acad. Sci. USA (1996) 93: 11371-11377.
Global Prior Art, Executive Summary & Search Report for State of the Art Search Surrounding Brown Adipose Tissue Manipulation, Sep. 24, 2009.
Graham et al. (1973) Virol. 52:456 467.
Gronthos, S., Blood (1994) 84(12): 4164-4173.
Heaton, "The Distribution of Brown Adipose Tissue in the Human," J Anat., May 1972, 112(Pt 1): 35-39.
Herlitze S, Landmesser LT, Curr Opin Neurobiol. Feb. 2007;17(1):87-94. Epub Dec. 15, 2006. Review.
Herpin TF et al., J Med Chem. Mar. 27, 2003;46(7):1123-6.
Hodgkin & Huxley, "A quantitative description of membrane current and its application to conduction and excitation in nerve," J Physiol, 1952, 117:500-544.
Horowitz et al., "Norepinephrine-induced depolarization of brown fat cells," Proc. N. A. S, 1969, 64: 113-120.
International Search Report and Written Opinion for PCT/US 10/62464 dated Feb. 24, 2011 (8 pages).
Jaiswal, N., et al., J. Cell Biochem. (1997) 64(2): 295-312.
Johnstone, B., et al., (1998) 238(1): 265-272.
Kafri, T. et al., J. Virol. (1999) 73: 576-584.
Klein et al. (1987) Nature 327:70 73.
Ladner et al. (1987) EMBO J. 6: 2693-2698.
Lever et al., "Demonstration of a Catecholaminergic Innervation in Human Perirenal Brown Adipose Tissue At Various Ages in the Adult," Anat Rec., Jul. 1986, 215(3): 251-5, 227-9.
Lin et al. 2002. "Spatially discrete, light driven protein expression." Chemistry & Biology, vol. 9, 1347-53.
Makino, S., et al., J. Clin. Invest. (1999) 103(5): 697-705).
Mannino et al. (1988) BioTechniques 6:682-690.
Masamoto et al., "Intragastric Administration of TRPV1, TRPV3, TRPM8, and TRPA1 Agonists Modulates Autonomic Thermoregulation in Different Manners in Mice," Bioscience, Biotechnology, and Biochemistry. vol. 73 (2009), No. 5 pp. 1021-1027.
Mayer and Heckel. 2006. "Biologically Active Molecules with a 'Light Switch'."Angew. Chem. Int. Ed. 45, 4900-4921.
McKnight et al. (1984) Cell 37: 253-262.
McMinn, J. E., Baskin, D. G. & Schwartz, M. W., Obes Rev 2000; 1:37-46.
Minokoshi et al., "Sympathetic Activation of Lipid Synthesis in Brown Adipose Tissue in the Rat," J. Pysio. (1988) 398, 361-70.
Mochizuki, H., et al., J. Virol. (1998) 72: 8873-8883.
Molecular Biology of the Cell, 3rd Edition, ed. By Alberts et al., New York: Garland Publishing, 1994, Ch. 19.
National Institute of Health, Clinical Guidelines on the Identification, Evaluation, and Treatment of Overweight and Obesity in Adults (1998).
Ng et al. (1985) Mol. Cell Biol. 5: 2720-2732.
Palucki BL et al., Bioorg Med Chem Lett. Jan. 3, 2005;15(1):171-5.
Rehnmark et al. In J Biol Chem 265: 16464-16471, 1990.
Reimann et al., "Characterization and Functional Role of Coltage Gated Cation Conductances in the Glucagon-Like Peptide-1 Secreting GLUTag cell line," J Physiol, 2005, 161-175.

Rial et al., "The Structure and Function of the Brown Fat Uncoupling Protein UCP1: Current Status," Biofactors 8 p. 209-219 (1998).
Ricquier et al., "Contribution to the Identification and Analysis of the Mitochondrial Uncoupling Proteins," Journal of Bioenergetics and Biomembranes vol. 31, No. 5 (Oct. 1999).
Rosell et al., "Skin Impedance From 1 Hz to 1MHz," IEEE Transactions on Biomedical Engineering, vol. 35, No. 8, Aug. 1988, 649-651.
Rosenfeld et al. (1991) Science 252:431-434.
Rosenfeld et al. (1992) Cell 68:143-155.
Rothwell et al, "A Role for Brown Adipose Tissue in Diet-Induced Thermogenesis," Nature, vol. 281, Sep. 6, 1979.
Saito et al. 2009. "High Incidence of Metabolically Active Brown Adipose Tissue in Healthy Adult Humans: Effects of Cold Exposure and Adiposity." Diabetes. 58, 1526-31.
Salmons, B. and Gunzburg, W. H., "Targeting of Retroviral Vectors for Gene Therapy," Hum. Gene Therapy (1993) 4: 129-141.
Sambrook et al. (1989) Molecular Cloning, a laboratory manual, Cold Spring Harbor Laboratories, N. Y.
Schmelz et al., "Delayed responses to electrical stimuli reflect C-fiber responsiveness in human microneurography," Exp Brain Res, 1995, 104: 331-336.
Sebhat IK et al. J Med Chem. Oct. 10, 2002;45(21):4589-93.
Seydoux et al., "Impaired Metabolic Response to Nerve Stimulation in Brown Adipose Tissue of Hypothyroid Rats," Molecular and Cellular Endocrinology 25 p. 213-226 (1982).
Shigekawa et al. (1988) BioTechniques 6:742-751.
Shimizu et al., "Sympathetic Activation of Glucose Utilization in Brown Adipose Tissue in Rats," Journal of Biochemistry, vol. 110, No. 5, 1991, pp. 688-692.
Solicore Flexion Batteries Product Line, available at Solicore, Inc. website, date of first publication unknown, revision 3 date Jan. 2007 (1 page).
Solicore SF-2529 Product Brochure, date of first publication unknown, revision 2 date Aug. 2008 (3 pages).
Solicore SF-4823 Product Brochure, date of first publication unknown, revision 2 date Aug. 2008 (3 pages).
Stylopoulos et al., "Roux-en-Y Gastric Bypass Enhances Energy Expenditure and Extends Lifespan in Diet-Induced Obese Rats," Obesity 17 (Oct. 1, 2009), 1839-47.
Sustained and Controlled Release Drug Delivery Systems, J.R. Robinson, ed., Marcel Dekker, Inc., New York, 1978.
Sutton, R., et al., J. Virol. (1998) 72: 5781-5788.
Tajino K, et al, "Application of Menthol to the Skin of Whole Trunk in Mice Induces Autonomic and Behavioral Heat-Gain Responses," Am J Physiol Regul Integr Comp Physiol. Nov. 2007; 293(5):R2128-35, Epub Aug. 29, 2007.
Testerman et al. 2006. "Electrical Stimulation as Therapy for Neurological Disorders: The basics of Implantable Neurological Stimulators." IEEE Engineering in Medicine and Biology Magazine. September/October, 74-8.
U.S. Appl. No. 12/605,409, filed Oct. 26, 2009.
U.S. Appl. No. 12/976,648, filed Dec. 22, 2010.
U.S. Appl. No. 12/980,635, filed Dec. 29, 2010.
U.S. Appl. No. 12/980,659, filed Dec. 29, 2010.
U.S. Appl. No. 12/980,695, filed Dec. 29, 2010.
U.S. Appl. No. 12/980,710, filed Dec. 29, 2010.
van Marken Lichtenbelt et al, "Cold Activated Brown Adipose Tissue in Healthy Men," N. Engl. J. Med., Apr. 2009, 360, 1500 1508.
Virtanen et al., "Functional Brown Adipose Tissue in Healthy Adults," The New England Journal of Medicine, vol. 360, No. 15, Apr. 9, 2009, 1518-1525.
Wagner, E. et al., Proc. Natl. Acad. Sci USA (1992) 89: 6099-6103.
Weidner et al., "Time course of post-excitatory effects separates afferent human C fibre classes," J Physiol, 2000, 527: 185-191.
Wells J, Kao C, Jansen ED, Konrad P, Mahadevan-Jansen A., "Application of infrared light for in vivo neural stimulation," J Biomed Opt. Nov.-Dec. 2005;10(6):064003.
Wells J, Kao C, Konrad P, Milner T, Kim J, Mahadevan-Jansen A, Jansen ED., "Biophysical mechanisms of transient optical stimulation of peripheral nerve," Biophys J. Oct. 1, 2007;93(7):2567-80. Epub May 25, 2007.

Wells J, Kao C, Mariappan K, Albea J, Jansen ED, Konrad P, Mahadevan-Jansen A., "Optical stimulation of neural tissue in vivo," Opt Lett. Mar. 1, 2005;30(5):504-6.

Wells J, Konrad P, Kao C, Jansen ED, Mahadevan-Jansen A., "Pulsed laser versus electrical energy for peripheral nerve stimulation," J Neurosci Methods. Jul. 30, 2007;163(2):326-37. Epub Mar. 31, 2007.

Wells JD, Thomsen S, Whitaker P, Jansen ED, Kao CC, Konrad PE, Mahadevan-Jansen A., "Optically mediated nerve stimulation: Identification of injury thresholds.," Lasers Surg Med. Jul. 2007;39(6):513-26.

Wold, W., Adenovirus Methods and Protocols, Humana Methods in Molecular Medicine (1998), Blackwell Science, Ltd.

Wu et al., "A pilot study to evaluate the effect of splanchnic nerve stimulation on body composition and food intake in rats," Obes Surg, 2009, 19:1581-1585.

Xiong, C., et al., Science (1989) 243: 1188-1191.

Xu et al. (2001) Hum Gene Ther. 12:563-73.

Yin et al., "Inhibitory Effects of Intestinal Electrical Stimulation on Food Intake, Weight Loss, and Gastric Emptying in Rats," Am J Physiol Regul Integr Comp Physiiol, 2007, R78-82.

Yoo, et al., J. Bone Joint Surg. Am. (1998) 80(12): 1745-1757.

Zhao et al. (2009) Reproduct. Biol. Endrocrin. 7: 37-45.

Zheng et al., "Stimulation of sympathetic innervations in the upper gastrointestinal tract as a treatment for obesity," Med Hyp, 2009, 72: 706-710.

Zhixiong Ye et al., Bioorg Med Chem Lett. Jul. 15, 2005;15(14):3501-5.

International Search Report and Written Opinion on PCT/US10/62469 dated Apr. 25, 2011.

International Preliminary Report on Patentability mailed Aug. 2, 2012 for Application No. PCT/US2010/062469 (8 Pages).

* cited by examiner

METHODS OF ACTIVATING A MELANOCORTIN-4 RECEPTOR PATHWAY IN OBESE SUBJECTS

CROSS REFERENCE TO RELATED APPLICATIONS

The present application claims priority to Provisional U.S. Provisional Application Ser. No. 61/297,483, filed Jan. 22, 2010 and entitled "Diagnostic Methods And Combination Therapies Involving MC4R," which is incorporated by reference herein in its entirety.

The present application is being filed concurrently with U.S. application Ser. No. 12/980,659, entitled "Methods and Devices for Activating Brown Adipose Tissue Using Electrical Energy." U.S. Provisional Application Ser. No. 61/297,483, filed Jan. 22, 2010 and entitled "Diagnostic Methods and Combination Therapies Involving MC4R," which this application claims priority to was filed concurrently with U.S. Provisional Application Ser. No. 61/297,405 entitled "Methods and Devices for Activating Brown Adipose Tissue," which claims priority to U.S. Provisional Application Ser. No. 61/297,405, filed Jan. 22, 2010, all of which are also incorporated by reference herein in their entirety.

FIELD OF THE INVENTION

The present invention relates to methods and devices for the treatment of metabolic disease.

BACKGROUND OF THE INVENTION

Obesity represents the most prevalent of body weight disorders, and it is the most important nutritional disorder in the Western world, with estimates of its prevalence ranging from 30% to 50% of the middle-aged population. The number of overweight and obese Americans has continued to increase since 1960, a trend that is not slowing down. Today, 64.5 percent of adult Americans (about 199 million) are categorized as being overweight or obese. Obesity is becoming a growing concern as the number of people with obesity continues to increase and more is learned about the negative health effects of obesity. Each year, obesity causes at least 300,000 deaths in the U.S., and healthcare costs of American adults with obesity amount to more than $147 billion (Centers for Disease Control and Prevention). Severe obesity, in which a person is 100 pounds or more over ideal body weight, in particular poses significant risks for severe health problems. Accordingly, a great deal of attention is being focused on treating patients with obesity.

Even mild obesity increases the risk for premature death, diabetes, hypertension, atherosclerosis, gallbladder disease and certain types of cancer. Because of its high prevalence and significant health consequences, its treatment should be a high public health priority.

Surgical procedures to treat severe obesity have included various forms of gastric and intestinal bypasses (stomach stapling), biliopancreatic diversion, adjustable gastric banding, vertical banded gastroplasty, gastric plications, and sleeve gastrectomies (removal of all or a portion of the stomach). Such surgical procedures have increasingly been performed laparoscopically. Reduced postoperative recovery time, markedly decreased post-operative pain and wound infection, and improved cosmetic outcome are well established benefits of laparoscopic surgery, derived mainly from the ability of laparoscopic surgeons to perform an operation utilizing smaller incisions of the body cavity wall. However, such surgical procedures risk a variety of complications during surgery, pose undesirable post-operative consequences such as pain and cosmetic scarring, and often require lengthy periods of patient recovery. Patients with obesity thus rarely seek or accept surgical intervention, with less than about 1% of patients with obesity being surgically treated for this disorder. Furthermore, even if successfully performed and initial weight loss occurs, surgical intervention to treat obesity may not result in lasting weight loss, thereby indicating a patient's need for additional, different obesity treatment.

Nonsurgical procedures for treating obesity have also been developed. However, effective therapies for increasing energy expenditure leading to improvements in metabolic outcomes, e.g., weight loss, have focused on pharmaceutical approaches, which have various technical and physiological limitations.

It has been recognized in, for example, U.S. Pat. No. 6,645,229 filed Dec. 20, 2000 and entitled "Slimming Device," that brown adipose tissue (BAT) plays a role in the regulation of energy expenditure and that stimulating BAT can result in patient slimming. BAT activation is regulated by the sympathetic nervous system and other physiological, e.g., hormonal and metabolic, influences. When activated, BAT removes free fatty acids (FFA) and oxygen from the blood supply for the generation of heat. The oxidative phosphorylation cycle that occurs in the mitochondria of activated BAT is shown in FIGS. 1 and 2.

Accordingly, there is a need for improved methods and devices for treating obesity.

SUMMARY OF THE INVENTION

The present invention generally provides methods and compositions for treating metabolic disorders involving activation of melanocortin pathways. In one aspect, a method for determining an appropriate intervention in a subject with a metabolic disorder is disclosed. In another aspect, a method for determining an appropriate intervention that activates a melanocortin receptor pathway in a subject with a metabolic disorder is disclosed. In a further aspect, a method for activating a melanocortin-4 receptor pathway to induce weight loss in a subject with a metabolic disorder is disclosed. In yet another aspect, a composition for activating melanocortin receptor pathways in a target tissue in a subject to induce weight loss is disclosed.

One method can be directed to determining an appropriate intervention in a subject with a metabolic disorder by performing a first non-surgical intervention, measuring energy expenditure of the subject to assess the subject's response to the first intervention and selecting a second intervention appropriate for the subject based on the measured energy expenditure. In one embodiment, the method can further induce weight loss in the subject.

The first and second intervention of the method can be the same or different procedures. The interventions can also activate a melanocortin receptor pathway, such as MC3R and/or MC4R. Furthermore, the first intervention can be a temporary procedure. In one particular embodiment, the first intervention can be selected from a melanocortin-4 receptor agonist therapy or activation of brown adipose tissue. In another embodiment, the second intervention can be a melanocortin-4 receptor agonist therapy, activation of brown adipose tissue, or a surgical procedure, such as, gastric bypass, biliopancreatic diversion, vertical sleeve gastrectomy, adjustable gastric banding, vertical banded gastroplasty, intragastric balloon therapy, gastric plication, Magenstrasse and Mill, small bowel transposition, biliary diversion and duodenal endoluminal barrier. Moreover, the first intervention can be performed in tandem with the second intervention for a combination therapy.

Another aspect can be directed to a method of determining an appropriate intervention in a subject with a metabolic disorder by performing a first intervention that activates a melanocortin receptor pathway, measuring melanocortin receptor pathway activation to assess the subject's response to the first intervention and selecting a second intervention appropriate for the subject based on the measured activation and the second intervention's ability to activate the melanocortin receptor pathway. In particular, the melanocortin receptor pathway can be a MC3R and/or MC4R pathway. Furthermore, according to the method, melanocortin receptor pathway activation can induce weight loss in the subject.

As described above, the first and second intervention of the method can be the same or different procedure. Furthermore, the first intervention can be a temporary procedure. In one particular embodiment, the first intervention can be selected from a melanocortin-4 receptor agonist therapy, activation of brown adipose tissue or the temporary deployment of duodenal endoluminal barrier. In another embodiment, the second intervention can be a melanocortin-4 receptor agonist therapy, activation of brown adipose tissue, or a surgical procedure, such as, gastric bypass, biliopancreatic diversion, vertical sleeve gastrectomy, adjustable gastric banding, vertical banded gastroplasty, intragastric balloon therapy, gastric plication, Magenstrasse and Mill, small bowel transposition, biliary diversion and duodenal endoluminal barrier. Moreover, the first intervention can be performed in tandem with the second intervention for a combination therapy.

In a more particular embodiment, the method can be directed to measuring melanocortin receptor pathway activation. Measurements can be performed either indirectly by assessing energy expenditure or directly by detecting markers of melanocortin receptor activation.

A further embodiment can be directed to regional or tissue specific activation of a melanocortin receptor pathway. The first intervention, second intervention or both interventions can selectively activate the receptor pathway in a cell of a region of a brain, a spinal cord, a sympathetic nervous system, a parasympathetic nervous system, an enteric nervous system, a gastrointestinal tract and a pancreas.

Targeted activation can also be accomplished through a composition for activating melanocortin receptor pathways in a target tissue in a subject to induce weight loss. The composition can include a therapeutic agent that activates melanocortin receptor pathways and a pharmaceutically acceptable carrier. The therapeutic agent can derive its targeting capabilities by being hound to a carrier molecule and/or being formulated for delivery to a target tissue. The target tissue can be any region of the body including, but not limited to, a brain, a spinal cord, a sympathetic nervous system, a parasympathetic nervous system, an enteric nervous system, a gastrointestinal tract and a pancreas.

One additional aspect of the invention can be directed to activating a melanocortin-4 receptor pathway to induce weight loss in a subject with a metabolic disorder by performing a first intervention that activates MC4R pathway, measuring MC4R pathway activation to assess the subject's response to the first intervention and selecting a second intervention appropriate based on the measured MC4R pathway activation and its ability to activate the MC4R pathway to induce weight loss.

BRIEF DESCRIPTION OF THE DRAWINGS

The invention will be more fully understood from the following detailed description taken in conjunction with the accompanying drawings, in which.

DETAILED DESCRIPTION OF THE INVENTION

Figure 1:
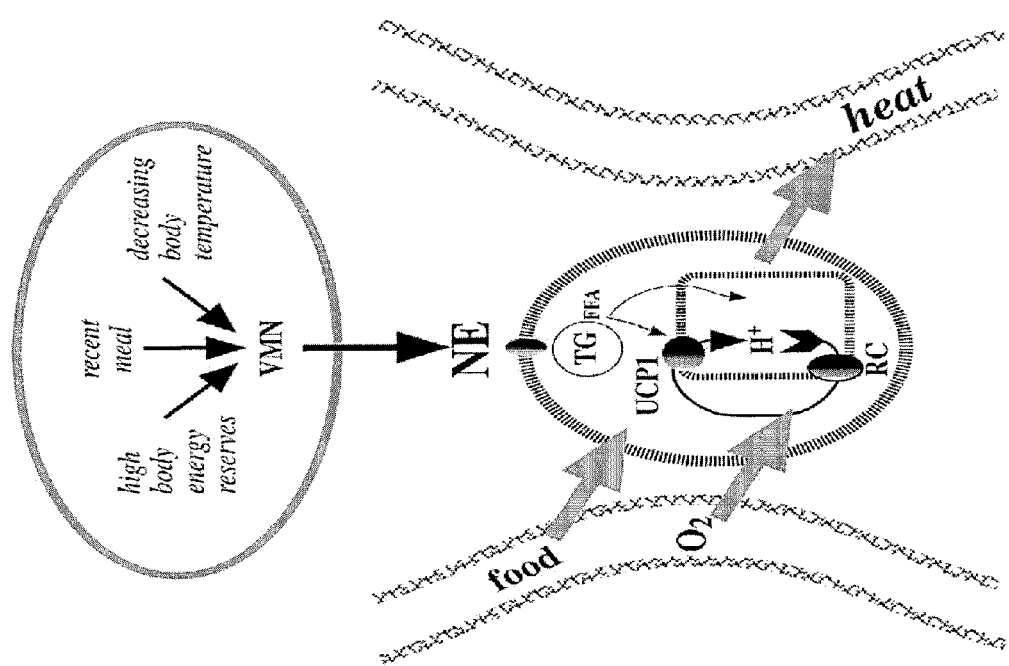
FIG. 1 is a schematic view of an oxidative phosphorylation cycle that occurs in mitochondria within BAT cells.
Figure 2:
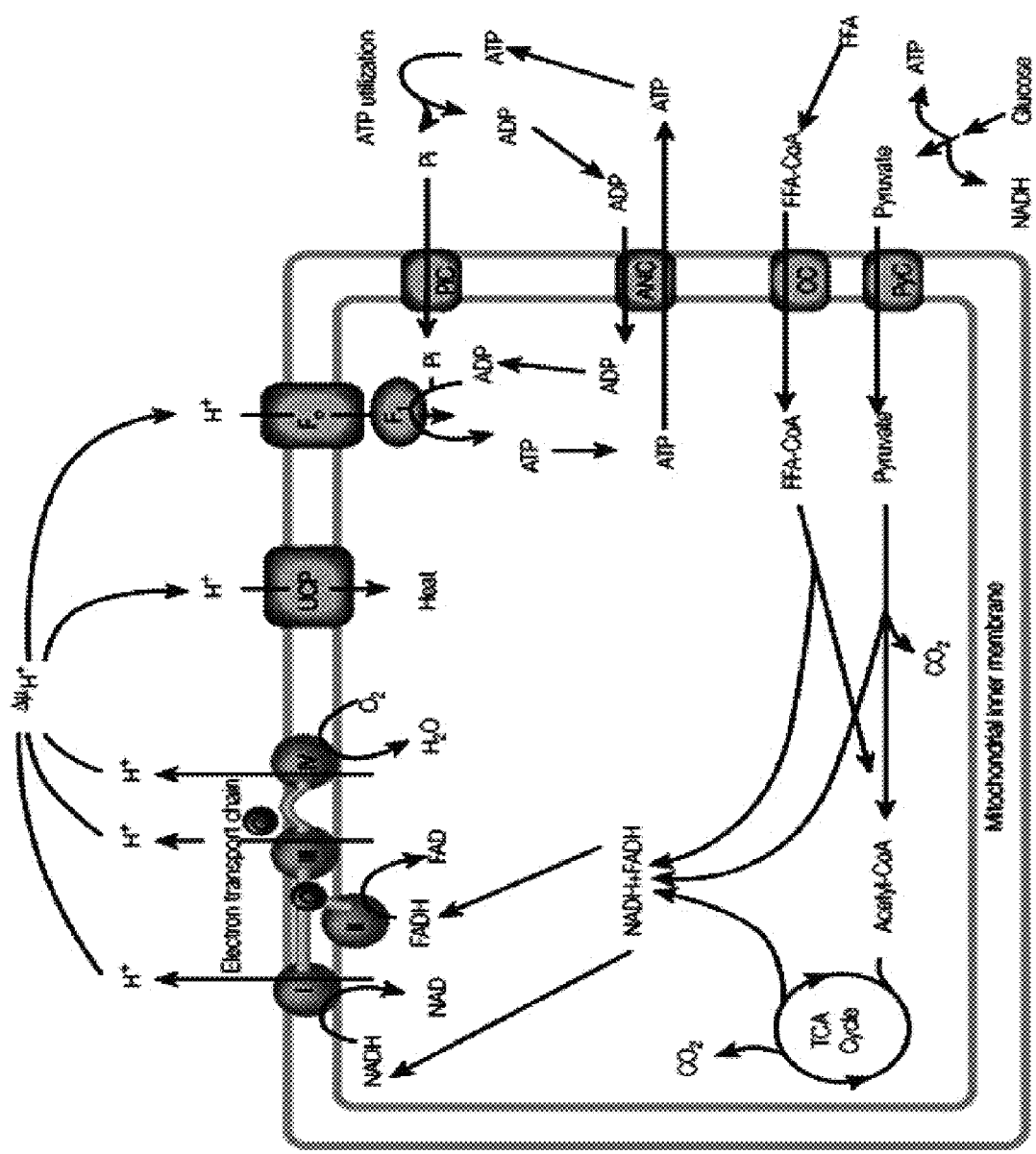
FIG. 2 is a schematic view of BAT mitochondria showing an oxidative phosphorylation cycle that occurs in the mitochondria.

Certain exemplary embodiments will now be described to provide an overall understanding of the principles of the structure, function, manufacture, and use of the therapeutics and methods disclosed herein. One or more examples of these embodiments are illustrated in the accompanying drawings. Those skilled in the art will understand that the therapeutics and methods specifically described herein and illustrated in the accompanying drawings are non-limiting exemplary embodiments and that the scope of the present invention is defined solely by the claims. The features illustrated or described in connection with one exemplary embodiment may be combined with the features of other embodiments. Such modifications and variations are intended to be included within the scope of the present invention.

All publications, patents and patent applications cited herein are hereby incorporated by reference in their entirety. As used in this specification and the appended claims, the singular forms "a," "an," and "the" include plural references unless the content clearly dictates otherwise. The terms used in this invention adhere to standard definitions generally accepted by those having ordinary skill in the art. In case any further explanation might be needed, some terms have been further elucidated below.

As used herein, the term "obesity" or "obese" typically refers to an individual having a body mass index (BMI) of 30 $kg/m^2$ or more. See National Institute of Health, Clinical Guidelines on the Identification, Evaluation, and Treatment of Overweight and Obesity in Adults (1998). The term "overweight" describes an individual having a body mass index (BMI) of 25 $kg/m^2$ or greater, but less than 30 $kg/m^2$ or an individual who has a desire to lose weight regardless of their BMI. BMI is a measure expressing the relationship (or ratio) of weight-to-height based on a mathematical formula in which a person's body weight in kilograms is divided by the square of his or her height in meters (i.e., $wt/(ht)^2$).

The term "energy expenditure," as used herein, refers to the amount of energy (calories), that a person uses to breathe, circulate blood, digest food, support routine physiological functions and be physically active. To prevent weight gain, energy intake (caloric intake) must be balanced with energy expenditure.

The term "metabolic disorder" as used herein, refers to disorders, diseases, and conditions that are caused or characterized by abnormal energy use or consumption or altered responses to ingested or endogenous nutrients, energy sources, hormones or other signaling molecules within the body. Some non-limiting examples can be obesity, diabetes, including type II diabetes, insulin-resistance syndrome, syndrome X, inflammatory and immune disorders, cancer, neurodegenerative disorders, and other disorders of metabolism.

The term "subject" as used herein refers to any living organism, including, but not limited to, humans, nonhuman primates such as chimpanzees and other apes and monkey species; farm animals such as cattle, sheep, pigs, goats and horses; domestic mammals such as dogs and cats; laboratory animals including rodents such as mice, rats, rabbits and guinea pigs, and the like. The term does not denote a particular age or sex. In a specific embodiment, the subject is human.

The terms "treating," "treatment" or "intervention" refer to the administration of one or more therapeutic agents or procedures to a subject who has a condition or disorder or a predisposition toward a condition or disorder, with the purpose to prevent, alleviate, relieve, alter, remedy, ameliorate, improve, affect, slow or stop the progression, slow or stop the worsening of the disease, at least one symptom of condition or disorder, or the predisposition toward the condition or disorder.

The term "bariatric surgery" as used herein refers to a surgical procedure to alter gastrointestinal structure or function so as to affect body weight, body composition, or energy balance regulation or otherwise alter metabolic function. Some non-limiting examples can be any form of gastric bypass, Roux-en-Y gastric bypass (RYGB), biliopancreatic diversion, vertical sleeve gastrectomy, adjustable gastric banding, vertical banded gastroplasty, intragastric balloon therapy, gastric plication and other forms of gastric volume reduction (see also US Patent Application Publication No. 2009/0024144, incorporated herein by reference), Magenstrasse and Mill, small bowel transposition, biliary diversion, duodenal endoluminal barrier and variations of the procedures above as well as other methods known by those skilled in the art.

As used herein, "pharmaceutically acceptable carrier" includes any and all solvents, dispersion media, coatings, antibacterial and antifungal agents, isotonic and absorption delaying agents, and the like that are physiologically compatible.

A "therapeutically effective amount" as used herein refers to an amount effective, at dosages and for periods of time necessary, of a therapeutic to achieve the desired therapeutic result. A therapeutically effective amount is also one in which any toxic or detrimental effects of the therapeutic are outweighed by the therapeutically beneficial effects. A "prophylactically effective amount" refers to an amount effective, at dosages and for periods of time necessary, to achieve the desired prophylactic result. Typically, since a prophylactic dose is used in subjects prior to or at an earlier stage of disease, the prophylactically effective amount can be less than the therapeutically effective amount.

The term "dosage unit form" as used herein refers to physically discrete units suited as unitary dosages for the mammalian subjects to be treated, each unit containing a predetermined quantity of active compound calculated to produce the desired therapeutic effect in association with the required pharmaceutical carrier.

The invention is generally directed to therapeutic methods and compositions, separately or in combination, for inducing weight loss in a subject by utilizing activation of melanocortin receptor pathways, in particular MC3R and MC4R, to determine which therapeutic intervention(s) is appropriate. Melanocortin receptor pathway activation can be assessed either indirectly, for example, by measuring energy expenditure or directly, for example, by detecting markers indicative of melanocortin receptor activation. Additionally, the level of melanocortin receptor activation can be used to predict the efficacy of the therapeutic intervention's ability to induce weight loss, where the intervention can be a non-surgical or a surgical procedure. The therapeutic can also be a composition for activating melanocortin receptor pathways in a target tissue. The composition can be bound to a targeting molecule, such as a carrier molecule, and/or formulated for delivery to the target tissue.

Another useful embodiment of the invention can be directed to combining therapeutic interventions. A diagnostic or first intervention can be performed to assess energy expenditure and/or melanocortin receptor pathway activation. Then, depending on the level of energy expenditure and/or melanocortin receptor pathway activation, a second intervention can be chosen. The second intervention can be the same intervention as the first intervention or it can be a different intervention. Additionally, the second intervention can be useful for increasing energy expenditure and/or melanocortin receptor pathway activation when combined with the first intervention. Overall, the therapeutic methods and compositions of the invention find particular use in inducing weight loss in the subject with a metabolic disorder.

Melanocortin Pathway

Five subtypes of receptors have been cloned and characterized in the melanocortin family. These G-protein coupled receptors (GPCR) stimulate the cAMP signal transduction pathway in many different tissues, mediating a wide range of physiological functions. Melanocortin 1 receptor (MC1R) (SEQ ID NO:1) is mainly expressed in melanocytes, monocytes, and mast cells, primarily mediating pigmentation of the hair and skin and to block inflammation. MC2R (SEQ ID NO:2) is expressed in adipocytes and adrenal cells, primarily mediating steroidogenesis in the adrenal gland. MC3R (SEQ ID NO:3) is present in the brain, including the hyphothalamus, as well as in the heart, gut, and placenta, and has been associated with energy homeostasis and inflammation. MC5R (SEQ ID NO:4) is found in a wide range of tissues and is considered to play a role in regulation of the exocrine gland system.

The MC4R gene (SEQ ID NO:5) also encodes a 332-amino-acid, seven-transmembrane domain receptor (SEQ ID NO:6) that transduces its signal by coupling to a heterotrimeric G-protein and activating adenylate cyclase. MC4R regulates food intake by integrating a satiety signal provided by its agonist α-MSH and an orexigenic signal provided by its antagonist agouti-related protein (AGRP). Both of these ligands are expressed in distinct neuronal populations of the arcuate nucleus of the hypothalamus and are coordinately regulated by the adipocyte-secreted hormone leptin to control food intake and maintain long-term energy homeostasis.

In murine models, MC4R has been found to be involved in feeding behavior, the regulation of metabolism, sexual behavior, and male erectile function. Mice deficient for another neuronal melanocortin receptor (Mc3r−/− or Mc3rKO mice) develop a similar degree of obesity to Mc4r−/− mice when fed a high fat diet, but do not exhibit the same level of insulin resistance, hyperlipidemia and increased hepatic steatosis. Mc3rKO and Mc4rKO mice both exhibit an exaggerated diet-induced obesity, however the deterioration of insulin sensitivity in Mc4rKO mice is more rapid and severe. Severe insulin resistance in mice and humans is associated with hepatomegaly and steatosis, with increased hepatic lipogenesis. Mc4rKO mice develop hepatic insulin resistance and hepatomegaly in the obese state, and on a high fat diet (HFD) exhibit a marked deterioration of glucose homeostasis associated with severe glucose and insulin intolerance. On the other hand, Mc3rKO matched to Mc4rKO for fat mass (FM) exhibit a very modest impairment of glucose homeostasis.

It has been shown that MC4R mutations are associated with inherited human obesity. Heterozygous mutations in the MC4R gene have been implicated in a significant proportion of cases of severe childhood-onset obesity. Heterozygote mutations suggest an autosomal dominant inheritance pattern. However, based on other research and observations, these mutations seem to have an incomplete penetrance and some degree of codominance. A frequency of about 4% pathogenic MC4R mutation carriers in adult patients from France with obesity and a similar frequency (3.5%) in adults from Northern California with obesity was observed. About 5.8% of people with early onset obesity have been found to harbor at least one mutant allele. The prevalence of MC4R mutations in people with body mass index (BMI) greater than 30 make it the most commonly known genetic defect predisposing people to obesity. Individuals harboring homozygous or compound heterozygous MC4R mutations are extremely rare.

Some non-limiting examples of MC4R mutations that have been characterized and shown to cause pathogenic structural changes or non-pathogenic changes to the MC4 receptor protein can be Ser4Scr, Arg7His, Thr11Ala, Arg18His (G53A), Ile69Met (A207G), Ile69Arg, Met79Ile, Tyr80stop (C240A), Ile102Thr (T305C), Val103Ile, (T337-A334insertionA), Ser127Leu (C380T), (C461A), Ala135Ala, Ile137Tyr, Thr150Ile, Ala154Asp, (597-599deletionGAT), Gln156Pro, Ala175Thr, Thr178Thr, Ile195Ser, Ile198Ile, Met200del, Phe202Leu, Gly231Ser (G691A), Asn240Ser, Ile251Leu, Gly252Ser, Val253Ile, Leu263Val, Asn274Ser, Ser295Pro (T883C), Pro299His, Tyr302Phe, Arg305Trp (C913T), Gln307stop (C919T), Gly324Gly, Arg331Tyr and Tyr332His (T994C). Furthermore, polymorphisms have been shown to have an association with obesity. Some non-limiting examples can be rs17782313 Val50Met, Val103Ile, V103I, C172R, M208V, F202L, G55V, A178C (rs34114122 5' untranslated region), 1251 L and Ser58Cys, see also WO 09/117,415. Other mutations or genetic polymorphisms in and around the MC3R and/or MC4R gene locus associated with obesity or a predisposition to obesity or other metabolic disorders are also included. The mutations or genetic polymorphisms can be obtained from human studies and/or mouse genetic models.

Recent data suggest that MC4R exhibits a constitutive activity upon which agouti-related protein (AGRP) acts as an inverse agonist to reduce MC4R basal cAMP production. AGRP is a neuropeptide produced in neurons in the brain. AGRP is co-expressed with other neuropeptides to increase appetite, decrease metabolism and energy expenditure. Its inverse agonism is highly specific for MC3R and MC4R. AGRP is hypothesized to bind MSH receptors and act as a competitive antagonist for ligand binding. Moreover, polymorphisms of AGRP have been linked to binge eating and other eating disorders.

Assessment of Pathway Activation

As shown in the Examples, the level of MC4R pathway activation is correlated to weight loss. By measuring MC4R pathway activation, either indirectly or directly, a prediction can be made concerning which therapeutic regimen or procedure would likely result in weight loss. Indirect measurements can include measurements of energy expenditure. Methods of determining energy expenditure can involve continuous measurements of heat output (direct calorimetry) or inhaled/exhaled gas exchange (indirect calorimetry) in subjects. Measurements of the heat released from a person's body can determine how much energy an activity has consumed. In addition, indirect calorimetry can measure oxygen consumption, carbon dioxide production and/or nitrogen excretion to calculate a ratio that reflects energy expenditure. A component of energy expenditure can be calculated as basal energy expenditure, which is the amount of energy required to maintain the body's normal metabolic activity, i.e. respiration, body temperature, etc.

Such energy expenditure or metabolic heat production in a subject can be assessed using several techniques. For measurement of the basal metabolic rate, the subject must be within its thermal neutral zone, which is the range of environmental temperatures across which the subject's body temperature can be maintained at its basal metabolic rate. The subject must be in a postabsorptive state, quiescent, in sexual repose, and resting but conscious. Since the latter prerequisite is often difficult to achieve with non-human subjects, the fasting heat production is used for animals which are quiet, but not necessarily resting.

Energy expenditure or metabolic heat production can be detected externally by the subject's heat loss pattern. Radiation, through which 40 to 60% of heat is lost from a subject, can be readily measured using any commercially available pyrometer or temperature sensor, since most radiated heat loss can be displayed in the 5-12 μm wavelength range of the electromagnetic spectrum. Direct and indirect calorimetry are further methods for assessing energy expenditure. Direct calorimetry measures heat loss from a subject directly by placing the subject at rest or exercising in a chamber surrounded by a waterjacket. Heat emitted from the subject raises the temperature of the water. The difference in the temperature of water entering and leaving the chamber reflects the subject's energy expenditure. Indirect calorimetry measures gas exchange and relates it to heat production. Indirect calorimetry involves monitoring of the amount of oxygen consumed (or conversely, the amount of carbon dioxide produced), and calculating the amount of energy expended by the subject, depending on the food substrate being utilized (e.g., fat, carbohydrate or protein).

Furthermore, subjects can be screened for the presence or absence of mutations and/or polymorphisms or other genetic markers of MC3R and/or MC4R as a measure of pathway activation. The mutations and/or polymorphisms, including those listed above, can be in and around the genetic loci. Methods known by those skilled in the art can be utilized to screen one or more than one genetic change. A diagnostic oligonucleotide or a diagnostic oligonucleotide set can be used to compare nucleotide sequences from a subject to directly determine the genotype as it correlates with a specified trait or phenotype, such as a disease. In one aspect, the invention is directed to a gene expression system having at least one, at least two, at least three or four oligonucleotides wherein the at least one, at least two, at least three or four oligonucleotides has a nucleotide sequence which each detects the presence or expression of a different mutations and/or polymorphisms or other genetic markers of MC3R and/or MC4R.

One aspect of the present invention can also be directed to a kit or a diagnostic method for determining the presence or absence or level of melanocortin receptor activation, in particular MC3R and/or MC4R. By determining the level of melanocortin receptor activation, a prediction can be made regarding the efficacy of a therapeutic intervention (e.g., a surgical procedure) and/or the intervention's ability to induce weight loss. Determining the presence or absence or level of activation of MC3R and/or MC4R can include, but is not limited to, screening for mutations and/or polymorphisms in and around the genetic loci, measuring MC3R and/or MC4R expression levels, measuring differential gene expression compared to inverse agonists or antagonists gene expression, determining receptor activation through expression of downstream signaling molecules, detecting differential surface receptors, determining ligand availability/accessibility to the MC3R and MC4R binding sites on the receptor, determining the presence and/or level of inverse agonists or antagonists to MC3R and MC4R activation and determining activation of downstream effector molecules. The diagnostic system can be a diagnostic agent, a diagnostic oligonucleotide, a diagnostic oligonucleotide set or a diagnostic probe set. The oligonucleotide molecules can be genomic DNA, RNA, protein nucleic acid (PNA), cDNA or synthetic oligonucleotides.

Non-Surgical Interventions

With obesity reaching epidemic proportions worldwide, there is a pressing need for the development of adequate therapeutics in this area. In recent years, hormones and neuropeptides involved in the regulation of appetite, body energy expenditures and fat mass accumulation have emerged as potential anti-obesity drugs (McMinn, J. E., Baskin, D. G. & Schwartz, M. W., Obes Rev 2000; 1:37-46; Drazen, D. L. & Woods, S. C., Curr. Opin. Clin. Nutr. Metab. Care 2003; 6:621-629).

With a plethora of physiological functions of melanocortin receptors, a large number of compounds have been designed and synthesized in a search for potent agonists and antagonists. Early examples are synthetic peptides and peptide analogues that have been identified on the basis of the endogenous agonist, α-MSH. These peptide agonists have been used to characterize the function of these receptors. NDP-MSH is a highly potent and nonselective agonist of MC1R, 3R, 4R and 5R, and has been reported to attenuate food intake and body weight gain in rat models. A cyclic heptapeptide MT-II is an agonist with a similar non-selective profile, and its therapeutic use has been proven in clinical trials for the treatment of erectile dysfunction.

Small molecule agonists for the melanocortin receptors have been reported to have significant activity in drug trials for the treatment of obesity, sexual dysfunction or inflammation. For example, a series of potent and selective MC4R agonists has been identified, one of which demonstrated significant effect for augmenting erectile response in mice (J. Med. Chem. 2002, 45, 4849). A number of MC4R agonists have also been identified, which displayed hyphophasic activity and anti-obesity effect in the rat model (Bioorg. Med. Chem. Lett. 2005, 15, 171, Bioorg. Med. Chem. Lett. 2005, 15, 3430, Bioorg. Med. Chem. Letu. 2005, 15, 3501). A highly potent and selective MC1R agonist has been discovered, which showed efficacy in an acute mouse model of inflammation (J. Med. Chem. 2003, 46, 1123). In addition, a variety of small molecules as MCR agonists have been described in the patent applications (WO 01/55109, WO 01/70337, WO 01/70708, WO 02/018327, WO 02/059095, WO 02/059107, WO 02/059117, WO 02/059108, WO 02/081443, WO 02/085925, WO 02/15909, WO 02/067869, WO 02/068387, WO 02/068388, WO 03/006620, WO 03/007949, WO 03/009847, WO 03/009850, WO 2004/087159, WO 2004/078716, WO 2004/078717, WO 2005/040109, WO 2005/047251, WO 2005/077935, WO 2005/077935, WO 2006/019787, WO 2006/020277, WO 2007/041052, WO 2007/041061, WO 2007/047496, WO 2006/072393, WO 2007/015157, WO 2007/015162, WO 2008/087190 and U.S. Pat. No. 5,731,408).

In addition to agonists to melanocortin receptors, other molecules regulating the melanocortin signaling pathway can be exploited to mimic the effects demonstrated with activation of melanocortin signaling. Such candidates can be inhibitors of agouti-related protein (AGRP), for example, leptin, syndecan-3, tissue inhibitor of metalloprotease-3 (TIMP-3), and analogs or derivatives thereof. Therapeutics that can influence genetic modifications, either temporarily or permanently, can also include gene silencing methods, including but not limited to, siRNA, microRNA, RNAi, dsRNA and others known by those skilled in the art.

Alternatively, precise delivery of the therapeutic into specific sites of the brain, can be performed using stereotactic microinjection techniques. For example, the subject being treated can be placed within a stereotactic frame base (MRI-compatible) and then imaged using high resolution MRI to determine the three-dimensional positioning of the particular region to be treated. The MRI images can then be transferred to a computer having the appropriate stereotactic software, and a number of images can be used to determine a target site and trajectory for therapeutic microinjection. The software translates the trajectory into three-dimensional coordinates that are precisely registered for the stereotactic frame. In the case of intracranial delivery, the skull will be exposed, burr holes will be drilled above the entry site, and the stereotactic apparatus used to position the needle and ensure implantation at a predetermined depth. The therapeutic can be delivered to regions, such as the cells of the spinal cord, brainstem, (medulla, pons, and midbrain), cerebellum, diencephalon (thalamus, hypothalamus), telencephalon (corpus stratium, cerebral cortex, or within the cortex, the occipital, temporal, parietal or frontal lobes), cells of central nervous system, autonomic (sympathetic nervous system or parasympathetic nervous system) nervous system or combinations thereof. In another embodiment, the therapeutic is delivered using other delivery methods suitable for localized delivery, such as localized permeation of the blood-brain barrier. Particularly useful delivery methods can include those that deliver the therapeutic to regions of the brain capable of MC4R activation.

In addition to the sympathetic and parasympathetic nervous system, the therapeutic can be delivered to peripheral sites that include the enteric nervous system (gastrointestinal tract, pancreas, etc). The enteric nervous system plays a predominant role in neuronal modulation of gastrointestinal (GI) function. It is recognized that the enteric nervous system (ENS) has a unique ability to mediate reflex activity independently of input from the brain or spinal cord. Complex reflex activities involving motor activity, secretion, absorption, blood flow, and interaction with other organs such as the gall bladder or pancreas occur in the absence of extrinsic autonomic and sensory input. Thus sensory receptors, primary afferent neurons, interneurons, and motor neurons mediating these types of reflex loops are contained within the two neural networks of the ENS: myenteric neurons that control GI motility and the submucosal neurons that modulate GI blood flow and intestinal ion transport.

The extensive regulatory activities of the ENS are made possible by the presence and abundance of different types of neurons within the wall of the gastrointestinal tract. The ENS contains about $10^8$ neurons, approximately the number of neurons found in the spinal cord. Moreover, a surprisingly large number of established or candidate neurotransmitters can be found in enteric neurons. Most neurons contain several of these substances, and distinctive patterns of colocalization of mediators allow identification of different functional classes of neurons. For example, myenteric neurons can express receptors for both peptide and non-peptide (amines, amino acids, purines) neurotransmitters.

One embodiment of the invention is directed to a therapeutic for activating melanocortin receptor signaling pathways in specific regions of the body to induce weight loss in a subject. The therapeutic can be a biochemical therapeutic agent, physiological therapeutic (e.g., physical means of activating signaling pathways such as radiological and electrical therapeutic procedures). In an exemplary embodiment, the therapeutic can be a therapeutic agent which can be covalently linked to the macromolecular carrier, which can be a hydrophilic and biocompatible macromolecule. The macromolecular carrier can have a molecular weight in the region of 5,000-200,000 D. In one case, the macromolecular carrier can be a polypeptide, a polynucleotide, a polysaccharide or a synthetic polymer such as poly(acrylate) or poly(ethyleneglycol). The polypeptide can comprise an inert protein such as serum albumin, for example bovine serum albumin (BSA), or an antibody or a fragment thereof.

In one embodiment, the macromolecular carrier can be a cellular targeting polypeptide. In another embodiment, the carrier can be specific to a cellular target, such that the therapeutic has the ability to selectively accumulate in a particular tissue, cell, compartments within the cell, such as mitochondria, lysosomes, inner cell membrane(s), endoplasmic reticulum or at the cell surface. The carrier can be intracellular and/or extracellular.

In another embodiment, the therapeutic agent can be formulated for delivery to a target areas of the body. The formulation can be for stereotactic, oral, injectable, infusible delivery, intravenous, subcutaneous, intraperitoneal, intramuscular, inhalation, transdermal, perorally delivery as well as other means known by those skilled in the art.

The therapeutic agent of the invention can be incorporated into pharmaceutical compositions suitable for administration to a subject. Typically, the pharmaceutical composition comprises the therapeutic agent of the invention and a pharmaceutically acceptable carrier. Examples of pharmaceutically acceptable carriers include one or more of water, saline, phosphate buffered saline, dextrose, glycerol, ethanol and the like, as well as combinations thereof. In many cases, it will be preferable to include isotonic agents, for example, sugars, polyalcohols such as mannitol, sorbitol, or sodium chloride in the composition. Pharmaceutically acceptable carriers may further comprise minor amounts of auxiliary substances such as wetting or emulsifying agents, preservatives or buffers, which enhance the shelf life or effectiveness of the therapeutic agent.

The therapeutic agents of this invention may be in a variety of forms. These include, for example, liquid, semi-solid and solid dosage forms, such as liquid solutions (e.g., injectable and infusible solutions), dispersions or suspensions, tablets, pills, powders, liposomes and suppositories. The actual form to be utilized depends on the intended mode of administration and therapeutic application. Typical compositions are in the form of injectable or infusible solutions, such as compositions similar to those used for passive immunization of humans. One mode of administration is parenteral (e.g., intravenous, subcutaneous, intraperitoneal, intramuscular). In one embodiment, the therapeutic agent is administered by intravenous infusion or injection. In another embodiment, the therapeutic agent is administered by intramuscular or subcutaneous injection. In another embodiment, the therapeutic agent is administered perorally. In another embodiment, the therapeutic agent is administered locally to the target region. Local administration can be direct injection, such as intracerebral administration through stereotactic injection.

Therapeutic compositions typically must be sterile and stable under the conditions of manufacture and storage. The therapeutic agent can be formulated as a solution, microemulsion, dispersion, liposome, or other ordered structure suitable to high drug concentration. Sterile injectable solutions can be prepared by incorporating the active compound (i.e., antigen, antibody or antibody portion) in the required amount in an appropriate solvent with one or a combination of ingredients as enumerated above, as required, followed by filtered sterilization.

Generally, dispersions are prepared by incorporating the active compound into a sterile vehicle that contains a basic dispersion medium and the required other ingredients from those enumerated above. In the case of sterile, lyophilized powders for the preparation of sterile injectable solutions, the preferred methods of preparation are vacuum drying and spray-drying that yields a powder of the active ingredient plus any additional desired ingredient from a previously sterile-filtered solution thereof. The proper fluidity of a solution can be maintained, for example, by the use of a coating such as lecithin, by the maintenance of the required particle size in the case of dispersion and by the use of surfactants. Prolonged absorption of injectable compositions can be brought about by including in the composition an agent that delays absorption, for example, monostearate salts and gelatin.

As explained above, the therapeutic of the present invention can be administered by a variety of methods known in the art. As will be appreciated by the skilled artisan, the route and/or mode of administration will vary depending upon the desired results. In certain embodiments, the active compound may be prepared with a carrier that will protect the compound against rapid release, such as a controlled release formulation, including implants, transdermal patches, and microencapsulated delivery systems. Biodegradable, biocompatible polymers can be used, such as ethylene vinyl acetate, polyanhydrides, polyglycolic acid, collagen, polyorthoesters, and polylactic acid. Many methods for the preparation of such formulations are patented or generally known to those skilled in the art. See, e.g., *Sustained and Controlled Release Drug Delivery Systems*, J. R. Robinson, ed., Marcel Dekker, Inc., New York, 1978.

The pharmaceutical compositions of the invention may include a therapeutically effective amount or a prophylactically effective amount of the therapeutic of the invention. Both the therapeutically effective amount and the prophylactically effective amount of the therapeutic may vary according to factors such as the disease state, age, sex, and weight of the individual, and the ability of the therapeutic to elicit a desired response in the individual.

Dosage regimens may be adjusted to provide the optimum desired response (e.g., a therapeutic or prophylactic response). For example, a single bolus may be administered, several divided doses may be administered over time or the dose may be proportionally reduced or increased as indicated by the exigencies of the therapeutic situation. It is especially advantageous to formulate parenteral compositions in dosage unit form for ease of administration and uniformity of dosage. The specification for the dosage unit forms of the invention are dictated by and directly dependent on (a) the unique characteristics of the active compound and the particular therapeutic or prophylactic effect to be achieved, and (b) the limitations inherent in the art of compounding such an active compound for the treatment of sensitivity in individuals.

A typical dosage of a compound when employed in the method according to the present invention can be in the range from about 0.001 to about 100 mg/kg body weight per day, preferably from about 0.01 to about 50 mg/kg body weight per day, such as from about 0.05 to about 10 mg/kg body weight per day, administered in one or most doses, such as from 1 to 3 doses. A typical unit dosage form intended for oral administration one or more times per day, such as from one to three times per day, can suitably contain from about 0.05 to about 1000 mg, preferably from about 0.1 to about 500 mg, such as from about 0.5 to about 200 mg of the active compound. The exact dosage will depend upon the frequency and mode of administration, the gender, age, weight and general condition of the subject treated, the nature and severity of the condition treated, any concomitant diseases to be treated and other factors evident to those skilled in the art.

MC4R signaling can also influence adipose tissue to effect lipid mobilization and thermogenesis. It has been found that a majority of sympathetic premotor neurons projecting to the inguinal white fat depots express MC4R, implying an important role of MC4R signaling in the neural control of white adipose tissue function. MC4R is also expressed in sympathetic outflow neurons in brown adipose tissue (BAT) deposits, as well as parasympathetic preganglionic neurons.

Activation of brown adipocytes leads to mobilization of fat stores within these cells themselves. It also increases transport of free fatty acids (FFA) into these cells from the extracellular space and bloodstream. FFAs in the blood are derived primarily from fats metabolized and released from adipocytes in white adipose tissue (WAT) as well as from ingested fats. Stimulation of the sympathetic nervous system is a major means of physiologically activating BAT. Sympathetic stimulation also induces lipolysis in WAT and release of FFA from WAT into the bloodstream to maintain FFA levels. In this way, sympathetic stimulation leads ultimately to the transfer of lipids from WAT to BAT followed by oxidation of these lipids as part of the heat generating capacity of BAT.

Figure 3:
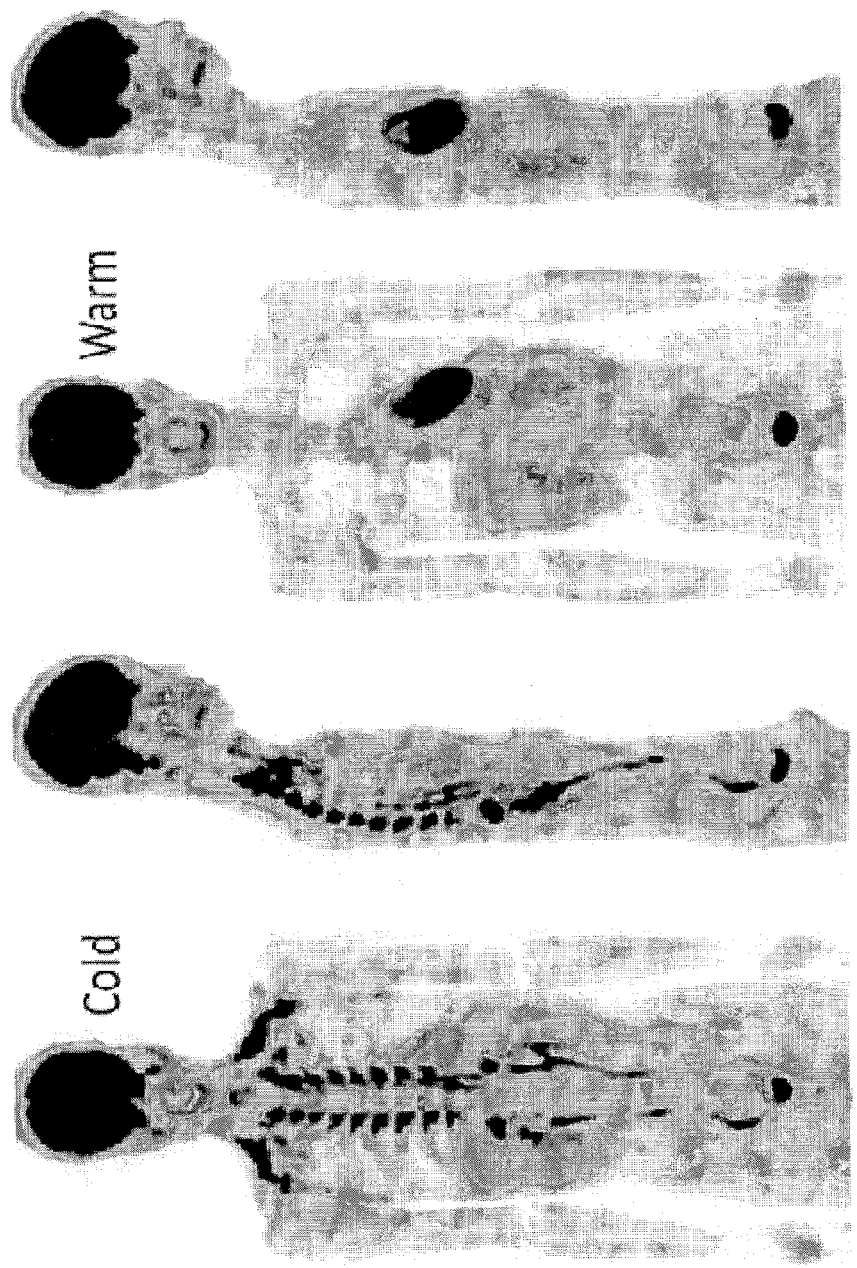
FIG. 3 is a schematic view of PET-CT images showing the locations of BAT depots in a patient subject to a cold environment and in the patient in a normal, warm environment.

The controlled activation of BAT can be optimized, leading to weight loss by reducing the stores of triglycerides in WAT. A person skilled in the art will appreciate that exposure to cold temperature leads to the activation of BAT to help regulate body temperature. This knowledge allows the location of BAT to be readily assessed using positron emission tomography—computed tomography (PET-CT) imaging. FIG. 3 shows scans of a patient subjected to a cold environment (left two images) and the same patient scanned in a normal, warm environment (right two images). Shown in black are regions of intense glucose uptake—namely, the brain, the heart, the bladder, and in the cold environment BAT. However these images show the locations of BAT depots—namely the nape of the neck, over the scapula, alongside the spinal cord, and around the kidneys as referenced by, for example, Rothwell et al, "A Role For Brown Adipose Tissue In Diet-Induced Thermogenesis," *Nature*, Vol. 281, 6 Sep. 1979, and Virtanen et al., "Functional Brown Adipose Tissue in Healthy Adults," *The New England Journal of Medicine*, Vol. 360, No. 15, Apr. 9, 2009, 1518-1525.

It is also conceived that non-radioactive based scanning or other imaging techniques could be used to measure changes in blood flow associated with the activation of BAT within a depot. The first technique involves the use of a contrast media containing microbubbles. The contrast media is injected into a patient whose BAT has been activated. An energy source such as low frequency ultrasound is applied to the region of interest to cause destruction of these bubbles. The rate of refill of this space is quantified. Increased rates of refill can be associated with active BAT depots. Another technique involves the use of a contrast media containing a fluorescent media. The contrast media is injected into a patient whose BAT has been activated. A needle based probe is placed in the region of interest that is capable of counting the amount of fluorescent contrast that passes the probe. Increased counts per unit time correspond to increased blood flow and can be associated with activated BAT depots.

A person skilled in the art will appreciate that adult humans have substantial BAT depots, as indicated, for example, in J. M. Heaton, "The Distribution Of Brown Adipose Tissue In The Human," *J. Anat.,* 1972 May, 112(Pt 1): 35-39. W. D. van Marken Lichtenbelt et al, "Cold-Activated Brown Adipose Tissue in Healthy Men," N. Engl. J. Med., 2009 April, 360, 1500-1508, and others. A person skilled in the art will also appreciate that BAT is heavily innervated by the sympathetic nervous system, as indicated, for example, in Lever et al., "Demonstration Of A Catecholaminergic Innervation In Human Perirenal Brown Adipose Tissue At Various Ages In The Adult," *Anat Rec.,* 1986 July, 215(3): 251-5, 227-9. Further, "[t]he thin unmyelinated fibers that contain norepinephrine (and not NPY) are those that actually innervate the brown adipocytes themselves. They form a dense network within the tissue, being in contact with each brown adipocyte (boutonen-passant), and their release of norepinephrine acutely stimulates heat production and chronically leads to brown adipose tissue recruitment". B. Cannon, and J. Nedergaard, "Brown Adipose Tissue: Function And Physiological Significance," *Physiol Rev.,* 2004:84:277-359.

Nerves innervating BAT can be stimulated to activate UCP1 and hence increase energy expenditure through heat dissipation through transcutaneous and/or direct stimulation of nerves innervating BAT. Transcutaneous and direct stimulation are each discussed below in more detail. In some embodiments, a pharmaceutical can be administered to a patient and/or the patient can be cooled in addition to transcutaneous and/or direct stimulation of BAT.

Whether BAT is activated directly and/or transcutaneously, target areas for BAT stimulation can include areas in the vicinity of BAT depots, e.g., the nape of the neck, over the scapula, alongside the spinal cord, and around the kidneys. Any BAT depot can be selected for activation. In the course of treating a patient, BAT nerves can be stimulated at any one or more BAT depots and can be stimulated simultaneously, e.g., two or more BAT depots being concurrently stimulated, or stimulated sequentially, e.g., different BAT depots being stimulated at different times. Simultaneous stimulation of BAT can help encourage more and/or faster energy expenditure. Sequential stimulation of BAT can help prevent the "burning out" of target nerves and can help stimulate the creation of new BAT cells. Sequential nerve stimulation can include stimulating the same BAT depot more than once, with at least one other BAT depot being activated before activating a previously activated BAT depot.

Figure 4:
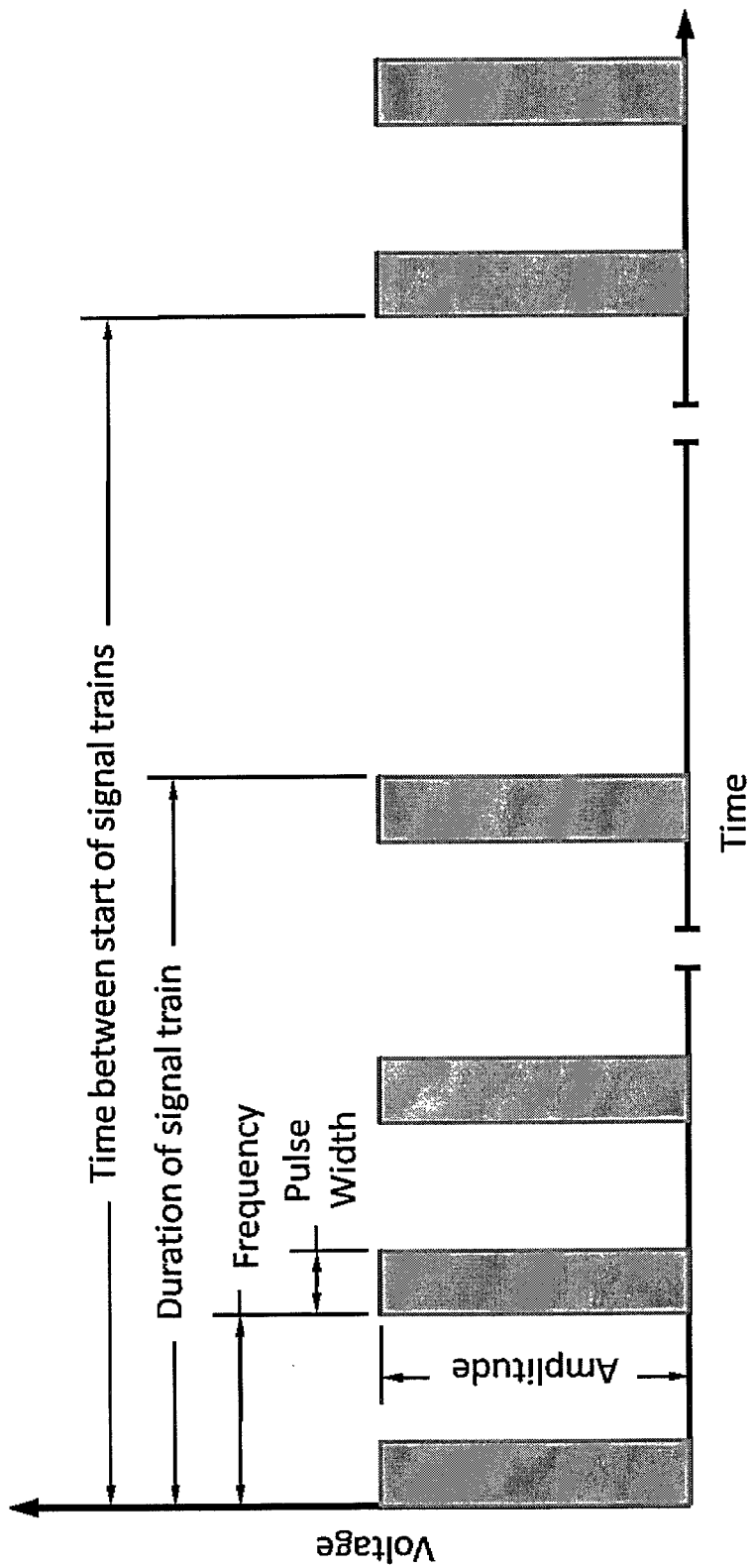
FIG. 4 is a graph showing voltage v. time for a generic electrical signal.

The electrical signal, whether transcutaneously or directly delivered, can be configured in a variety of ways. The stimulation "on" time amplitude can be higher for shorter periods and increased or decreased for longer periods of application. The electrical signal can have any "geometry" of the applied voltage, e.g., square waves, ramp waves, sine waves, triangular waves, and waveforms that contain multiple geometries. FIG. 4 illustrates amplitude, pulse width, activation signal pulse frequency, duration of signal train, and a time between start of signal trains for a generic (without any specified numerical parameters) electrical signal. In an exemplary embodiment, an electrical signal delivered to BAT can have a voltage having an amplitude in a range of about 1 to 20 V, e.g., about 10 V, e.g., about 4 V, about 7 V, etc.; a current having an amplitude in a range of about 2 to 6 mA, e.g., about 3 mA; a pulse width in a range about 10 µs to 40 ms, e.g., about 0.1 ms, about 2 ms, about 20 ms, etc.; an activation signal pulse frequency in a range of about 0.1 to 40 Hz, e.g., about 6 Hz; and a duration of signal train in a range of about 1 second to continuous, e.g., about 30 seconds, etc. A time between start of signal trains for a noncontinuous electrical signal delivered to BAT can be of any regular, predictable duration, e.g., hourly, daily, etc., such as about ten minutes, or can be of any irregular, unpredictable duration, e.g., in response to one or more predetermined trigger events, as discussed further below.

Figure 5:
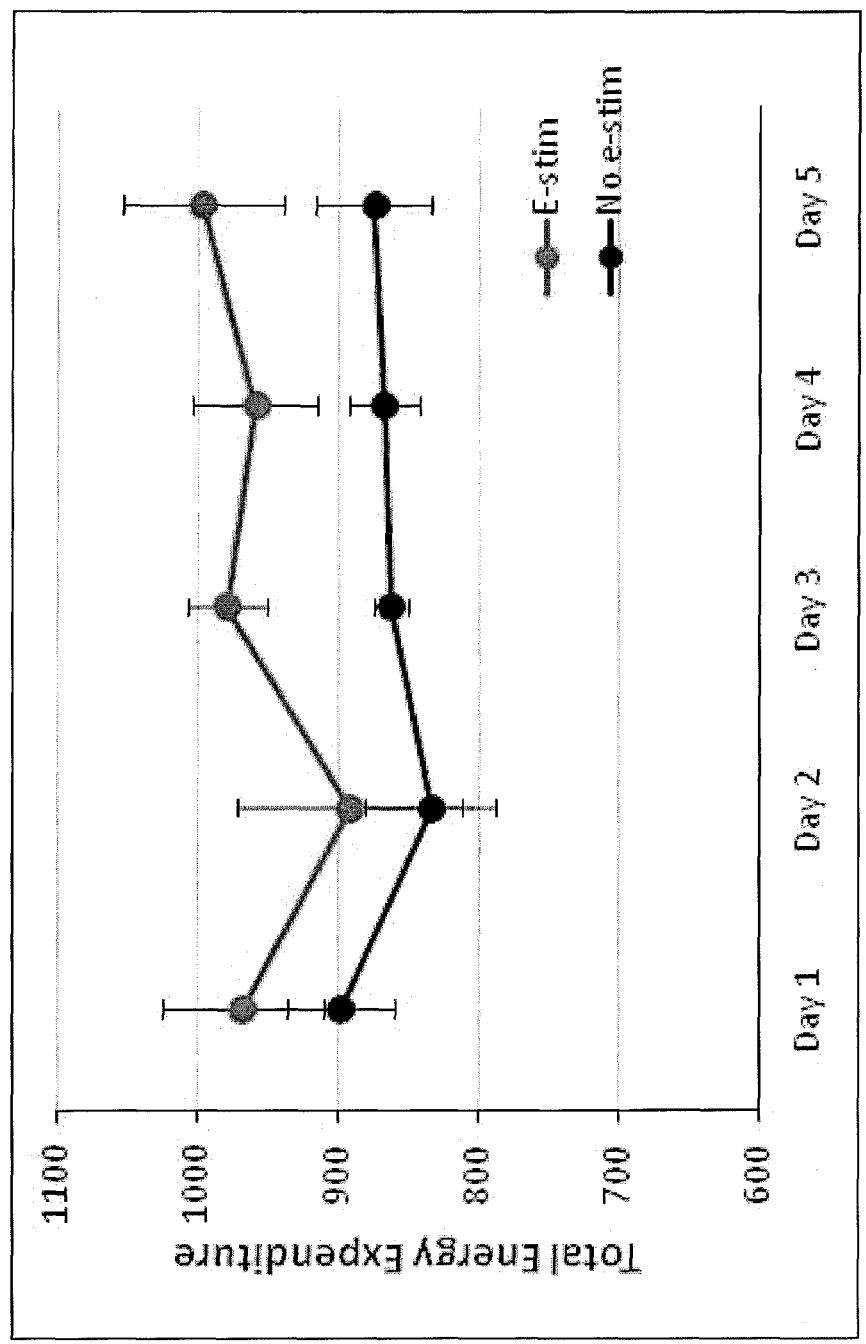
FIG. 5 is a graph showing total energy expenditure v. time for an experimental, continuous, direct electrical signal delivered to BAT depots in a group of subjects and showing total energy expenditure v. time for a group of non-stimulated control subjects.

In one non-limiting example, an electrical signal continuously delivered to BAT can be a pulse having an amplitude of about 7 V, a pulse width of about 0.1 ms, an activation signal pulse frequency of about 6 Hz. FIG. 5 shows one example of a graph of total energy expenditure v. time of continuous direct delivery of this electrical signal via implanted device to an interscapular BAT depot over a period of five days. Results of electrical stimulation using this electrical signal is shown by the graph line beginning at about 970 at Day 1, and a control of non-electrical stimulation is shown by the graph line beginning at about 900 at Day 1. As illustrated in the graph, the electrical signal delivery can lead to a sustained increase in oxygen consumption, which is correlated with increases in energy expenditure in the subjects, which are rats in the illustrated example. Over time, the increases in energy expenditure can lead to weight loss. Activity of the subjects receiving this electrical signal over the five day period was observed to be similar to activity of the subjects not receiving electrical stimulation over the five day period, thereby indicating that the illustrated increased energy expenditure of the stimulated subjects was due to the electrical stimulation and not due to increased physical activity and that the subjects were behaving normally during the stimulation treatment.

Figure 6:
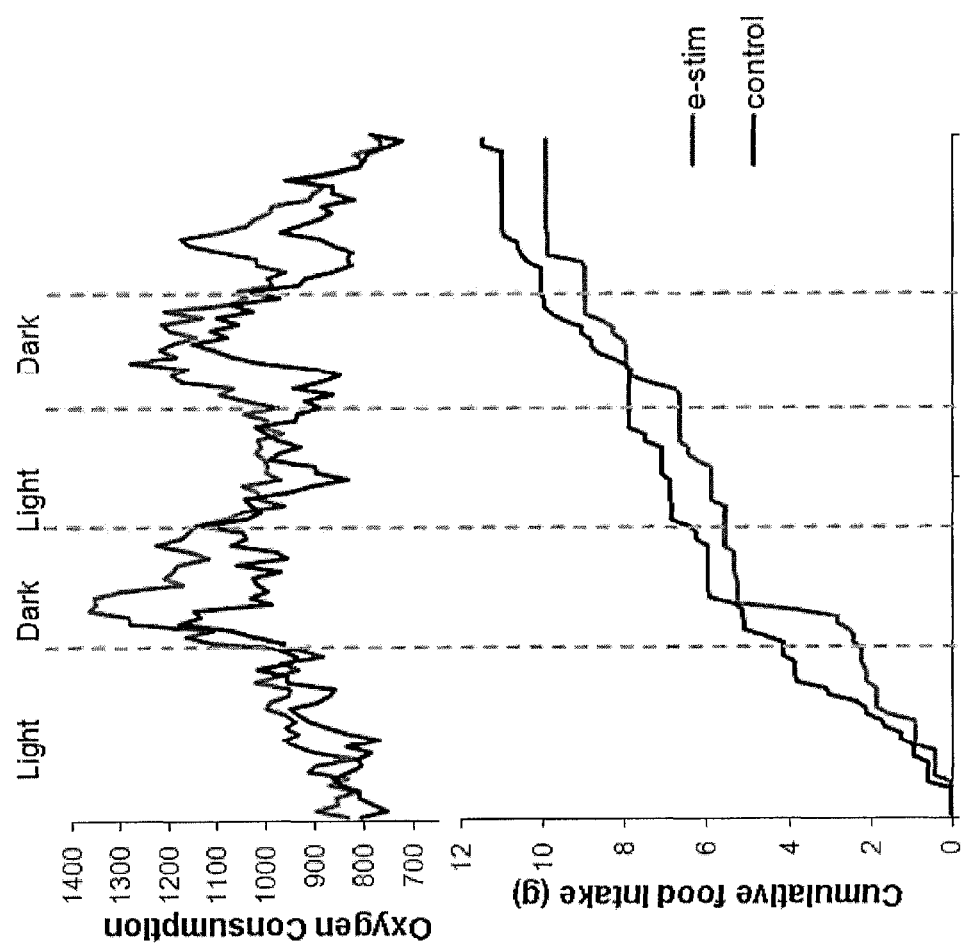
FIG. 6 is a graph showing a first plot of oxygen consumption v. time for the experimental, continuous, direct electrical signal delivered to BAT depots in the group of subjects of FIG. 5 and showing oxygen consumption v. time for the group of non-stimulated control subjects of FIG. 5, and showing a second plot of cumulative food intake v. time for the experimental, continuous, direct electrical signal delivered to BAT depots in the group of subjects of FIG. 5 and showing cumulative food intake v. time for the group of non-stimulated control subjects of FIG. 5.
Figure 7:
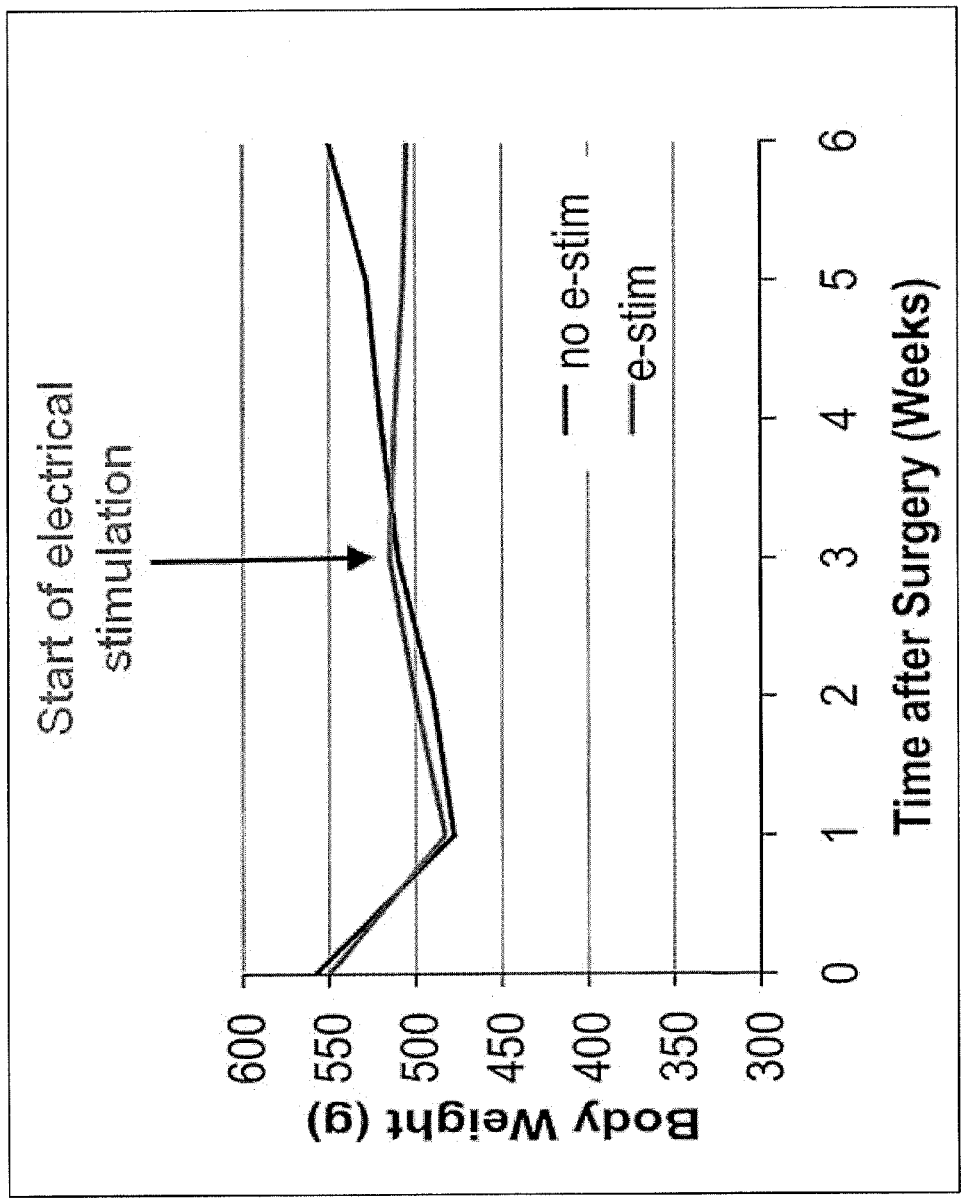
FIG. 7 is a graph showing body weight v. time for the experimental, continuous, direct electrical signal delivered to BAT depots in the group of subjects of FIG. 5 and showing body weight v. time for the group of non-stimulated control subjects of FIG. 5.

Oxygen consumption is plotted versus time for a 48 hour period in one example of a graph in FIG. 6 in which measurements were taken every 10 minutes. In the top plot in FIG. 6, results of electrical stimulation using this electrical signal are shown by the graph line beginning at about 825 at time zero, and a control of non-electrical stimulation is shown by the graph line beginning at about 800 at time zero. In the bottom plot of FIG. 6, results of electrical stimulation using this electrical signal are shown by the graph line which is at about 9 g at an end of the 48 time period, and a control of non electrical stimulation is shown by the graph line which is at about 11 g at the end of the 48 time period. Sustained moderate increases in energy expenditure were present for the electrically stimulated animals in the two light time periods, e.g., times when the animals were at rest, while more pronounced increases in energy expenditure were present for the electrically stimulated animals in the two dark time periods, e.g., when the animals were active and eating. Thus, when subjects stimulated with this electrical signal were active and eating, energy expenditure increased substantially, whereas moderate increases were observed at rest. Such an increase is consistent with diet-induced thermogenesis. The increase also demonstrates that continuous direct electrical stimulation can help ensure that at any time a subject eats, stimulated BAT can be ready to take the consumed calories and turn them into heat, thereby encouraging weight loss over time, as shown in one example of a graph in FIG. 7. Body weight is plotted versus time for a six week period in FIG. 7, with time zero representing a time of surgery to implant electrodes, which was performed on all subjects, and with week three marking a start time of electrical stimulation for the non-control group subjects. Results of electrical stimulation using this electrical signal are shown by the graph line beginning at about 550 g at time zero, and a control of non-electrical stimulation is shown by the graph line beginning at about 560 g at time zero. FIG. 7 illustrates that upon the start of electrical stimulation of BAT at week three, the electrically stimulated animals experienced continual weight loss until at least week six. In contrast, the control, non-electrically stimulated animals gained weight during the same period starting at week three, resulting in a difference in weight of about 15 percent between the stimulated group and the non-stimulated group.

Figure 8:
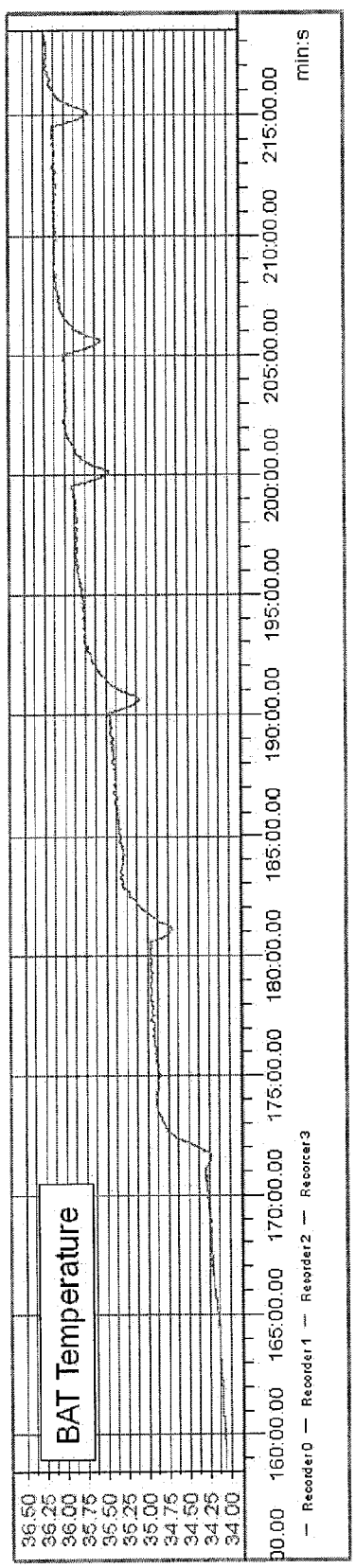
FIG. 8 is a graph showing BAT temperature v. time for an experimental, intermittent, direct electrical signal delivered to BAT depots in one subject.

In another non-limiting example, an electrical signal delivered to BAT can be a pulse having an amplitude of about 4 V, a pulse width of about 20 ms, an activation signal pulse frequency of about 6 Hz, a duration of signal train of about 30 seconds, and a time between start of signal trains of about 10 minutes. FIG. 8 shows one example of a graph of BAT temperature in degrees Celsius v. time of intermittent direct delivery of this electrical signal to a BAT depot of one patient. As illustrated in the graph, the electrical signal delivery can lead to a sustained increase in BAT temperature, which can be associated with a lagging increase in core temperature of the subjects, which are rats in the illustrated example. Over time, the sustained increase in BAT temperature can lead to weight loss.

Figure 9:
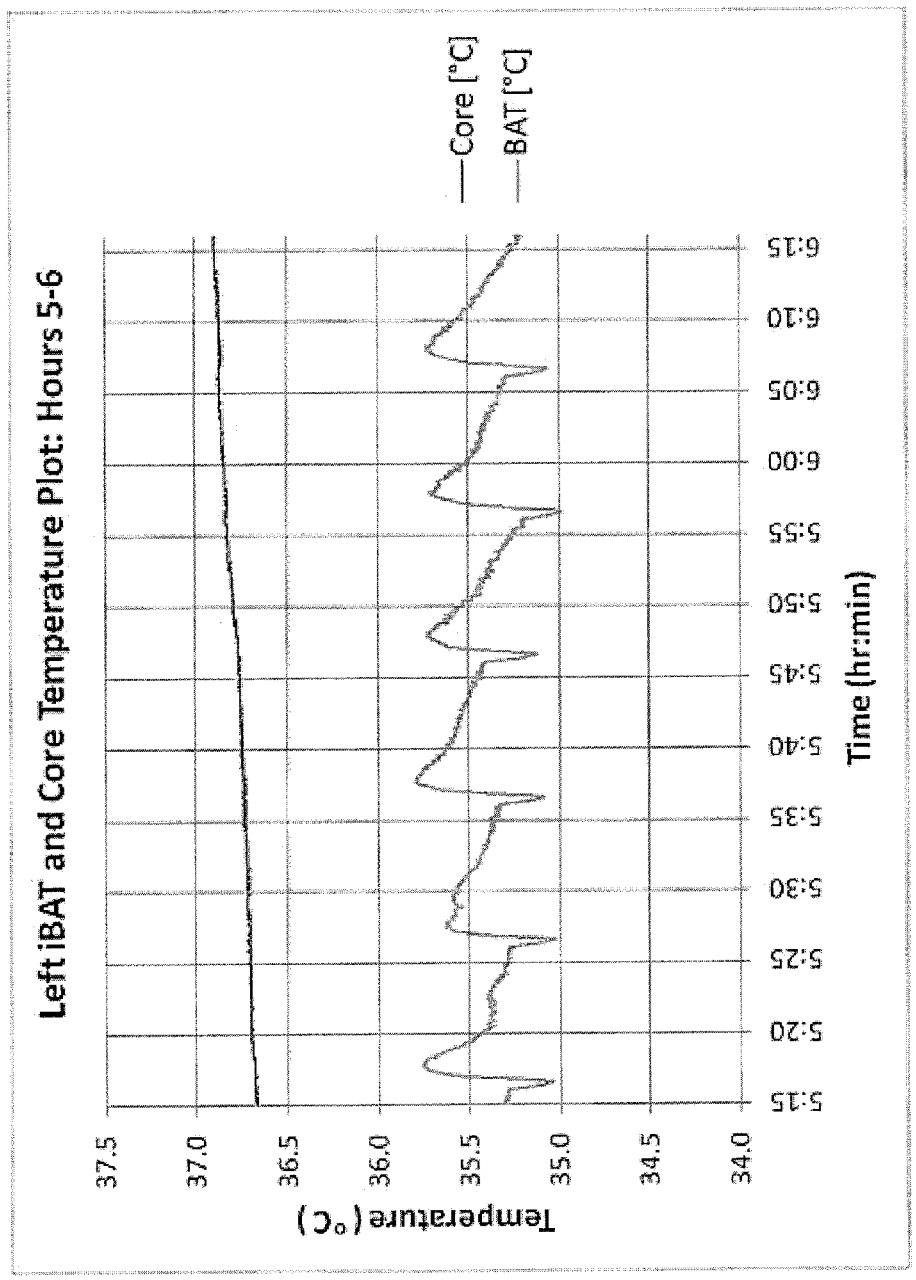
FIG. 9 is a graph showing BAT and core temperatures v. time for an experimental, intermittent, direct electrical signal delivered to BAT depots in one subject.

In another non-limiting example, an electrical signal delivered to BAT can be a pulse having an amplitude of about 10 V, a pulse width of about 2 ms, an activation signal pulse frequency of about 6 Hz, a duration of signal train of about 30 seconds, and a time between start of signal trains of about 10 minutes. FIG. 9 shows one example of a graph of BAT temperature v. time of direct delivery of this electrical signal to a BAT depot of one patient during hours 5 and 6 of intermittent electrical signal delivery to subjects (rats in this illustrated example). Core temperature is shown by the graph line beginning at about 36.7° C. at time 5:15, and BAT temperature is shown by the graph line beginning at about 35.3° C. at time 5:15. As illustrated in the graph, the electrical signal delivery can lead to a sustained activation of BAT. Over time, the sustained activation of BAT can lead to weight loss.

In another non-limiting example an electrical signal delivered to BAT can be configured as a monophasic square pulse having a square wave shape, a voltage alternating in amplitude from about 0 to 20 V, an activation signal pulse frequency in a range of about 5 to 10 Hz, a pulse width (duration) of about 2 ms, a pulse train on/off time of about 20 seconds "on" and about 40 seconds "off," and a treatment time of about 11 minutes, as described in more detail in Shimizu et al., "Sympathetic Activation of Glucose Utilization in Brown Adipose Tissue in Rats," *Journal of Biochemistry*, Vol. 110, No. 5, 1991, pgs 688-692. Further non-limiting examples of electrical signals that can be delivered to BAT are described in more detail in Flaim et al., "Functional and Anatomical Characteristics of the Nerve-Brown Adipose Interation in the Rat," *Pflügers Arch.*, 365, 9-14 (1976); Minokoshi et al., "Sympathetic Activation of Lipid Synthesis in Brown Adipose Tissue in the Rat," *J. Psysio.* (1988) 398, 361-70; and Horwitz et al., "Norepinephrine-Induced Depolarization of Brown Fat Cells." *Physiology* (1969) 64, 113-20.

In one embodiment, the same electrical signal can be delivered to a particular BAT depot, either continuously or sequentially. In another embodiment, a first electrical signal can be transcutaneously or directly delivered to a particular BAT depot, and then subsequently, either immediately thereafter or after a passage of a period of time, a second, different electrical signal can be delivered to the same particular BAT depot. In this way, chances of a BAT depot adapting to a particular electrical signal can be reduced, thereby helping to prevent the BAT depot from becoming less receptive to electrical stimulation.

Whether a continuous electrical signal or an intermittent electrical signal is transcutaneously delivered, e.g., with a transdermal patch as discussed further below, or subcutaneously delivered via an at least partially implanted device, the electrical signal can include a low frequency modulating signal and a high frequency carrier signal. Generally, the high frequency carrier signal can be used to pass through high impedance tissue (subcutaneous or transcutaneous) while the modulating signal, can be used to activate nervous tissue and/or electrically responsive brown adipocytes. The waveform can be generated by modulating a carrier waveform with a pulse envelope. Properties of the carrier waveform such as amplitude, frequency, and the like, can be chosen so as to overcome the tissue impedance and the stimulation threshold of the target nerve. The pulse envelope can be a waveform having a specific pulse width, amplitude and shape designed to selectively stimulate the target nerve. This waveform can be able to penetrate efficiently through tissue, such as the skin, to reach the target nerve with minimal loss in the strength of the electrical signal, thereby saving battery power that would otherwise have been used in several attempts to stimulate the target nerve with low frequency signals. Moreover, only the target nerve is stimulated, and non-target nerves, e.g., nerves associated with pain, are not stimulated. Exemplary embodiments of methods and devices for applying a signal including a high frequency carrier signal are described in more detail in U.S. Patent Publication No. 2009/0093858 filed Oct. 3, 2007 and entitled "Implantable Pulse Generators And Methods For Selective Nerve Stimulation," U.S. Patent Publication No. 2005/0277998 filed Jun. 7, 2005 and entitled "System And Method For Nerve Stimulation," and U.S. Patent Publication No. 2006/0195153 filed Jan. 31, 2006 and entitled "System And Method For Selectively Stimulating Different Body Parts."

Figure 10:
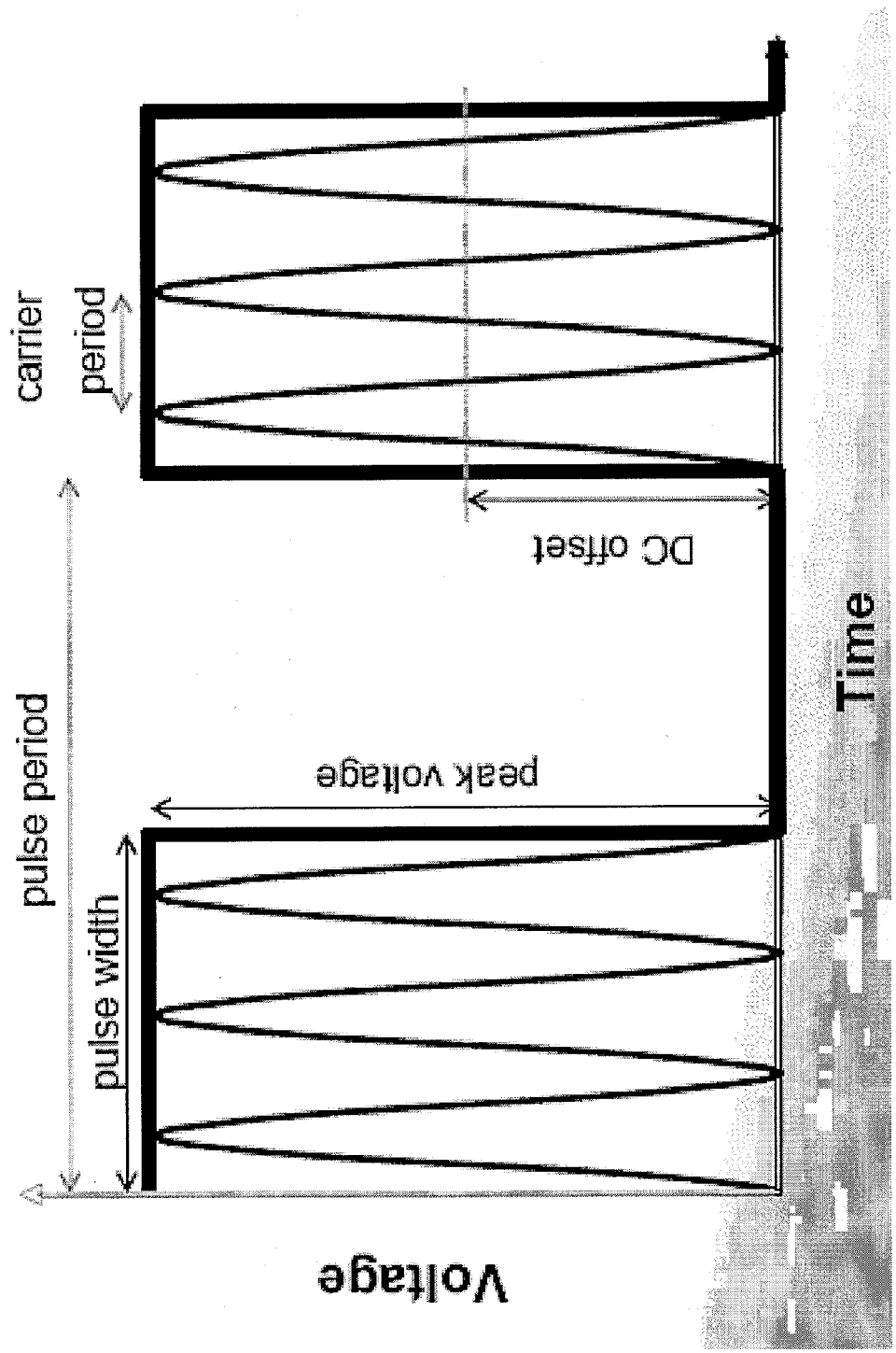
FIG. 10 is a graph showing voltage v. time for a generic electrical signal including a low frequency modulating signal and a high frequency carrier signal.

The low frequency modulating signal and a high frequency carrier signal can each have a variety of values and configurations. The low frequency modulating signal can be, e.g., a signal having an activation signal pulse frequency in a range of about 0.1 to 100 Hz, e.g., in a range of about 0.1 to 40 Hz, e.g., less than about 10 Hz. The high frequency carrier signal can be, e.g., in a range of about 10 to 400 kHz, e.g., in a range of about 200 to 250 kHz. Pulse widths can also vary, e.g., be in a range of about 10 µs to 10 ms, e.g., less than about 2 ms. In one exemplary embodiment, the electrical signal can have a modulating signal in a range of about 2 to 15 Hz, e.g., about 6 Hz, a carrier frequency of about 210 kHz, and a pulse width in a range of about 0.1 to 1 ms. FIG. 10 illustrates a generic (without any specified numerical parameters) electrical signal including a low frequency modulating signal L and a high frequency carrier signal H.

Generally, low frequency signals can cause activation of Types A and B fibers, e.g., myelinated neurons, and Type C fibers, e.g., unmyelinated neurons. The signal to activate Type C fibers can be greater than, e.g., a longer pulse width and a higher current amplitude, than a signal to activate Type A and B fibers. Postganglionic fibers innervating BAT depots likely include Type C fibers, thereby allowing a BAT depot to be activated by a low frequency signal, e.g., a signal less than about 10 Hz and having a pulse width greater than about 300 vs. Preganglionic nerves such as small diameter, unmyelinated Type C fibers and small diameter, myelinated Type B fibers may also innervate BAT, thereby also allowing a BAT depot to be activated by a low frequency signal, e.g., a signal in a range of about 10 to 40 Hz and having a pulse width less than about 200 µs.

An electrical signal delivered to a BAT depot can be applied continuously, in predetermined intervals, in sporadic or random intervals, in response to one or more predetermined trigger events, or in any combination thereof. If the signal is continuously delivered to the patient, particular care should be taken to ensure that the signal delivered to the patient will not damage the target nerves. For one non-limiting example, nerve damage can be reduced, if not entirely prevented, by continuously delivering an electrical signal via en electrode having a relatively large surface area to help distribute an electrical signal's energy between multiple nerves. For electrical signals delivered intermittently, nerve damage can be reduced, if not entirely prevented, by selecting an on/off ratio in which the signal is "off" for more time than it is "on." For non-limiting example, delivering an electrical signal to BAT intermittently with an on/off ratio of about 1:19, e.g., electrical signals delivered for 30 seconds every ten minutes (30 seconds on/9.5 minutes off), can help reduce or entirely prevent nerve damage. The device delivering the electrical signal can be configured to respond to one or more predetermined trigger events, e.g., events that are sensed by or otherwise signaled to the device. Non-limiting examples of trigger events include the patient eating, the patient resting (e.g., sleeping), a threshold temperature of the patient (e.g., a temperature in the stimulated BAT depot or a core temperature), a directional orientation of the patient (e.g., recumbent as common when sleeping), a change in the patient's weight, a change in the patient's tissue impedance, manual activation by the patient or other human (e.g., via an onboard controller, via a wired or wirelessly connected controller, or upon skin contact), a blood chemistry change in the patient (e.g., a hormonal change), low energy expenditure, menstrual cycles in women, medication intake (e.g., an appetite suppressant such as topiramate, fenfluramine, etc.) and a manually-generated or automatically-generated signal from a controller in electronic communication, wired and/or wireless, with the device. In one embodiment, the patient eating can be determined through a detection of heart rate variability, as discussed in more detail in U.S. patent application Ser. No. 12/980,695, filed Dec. 29, 2010 and entitled "Obesity Therapy and Heart Rate Variability" and U.S. patent application Ser. No. 12/980,710, filed Dec. 29, 2010 and entitled "Obesity Therapy and Heart Rate Variability". The controller can be internal to the device, be located external from but locally to device, or be located external and remotely from device. As will be appreciated by a person skilled in the art, the controller can be coupled to the device in any way, e.g., hard-wired thereto, in wireless electronic communication therewith, etc. In some embodiments, multiple devices can be applied a patient, and at least two of those devices can be configured to deliver an electrical signal based on different individual trigger events or combinations of trigger events.

Figure 11:
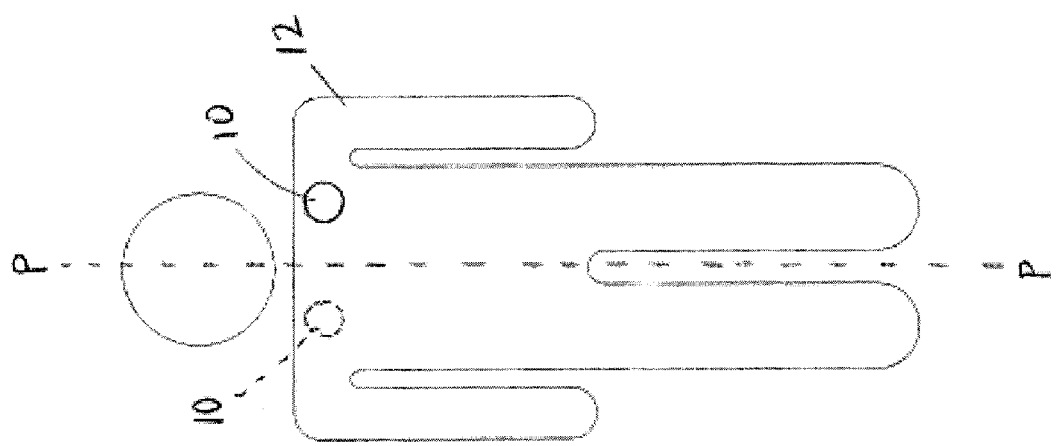
FIG. 11 is a front view of a body showing one embodiment of an electrical stimulation device positioned on opposite sides of the body's sagittal plane.

Generally, transcutaneous stimulation of BAT can include applying a device to an exterior skin surface of a patient proximate to a BAT depot and activating the device to deliver an electrical signal to the BAT depot. In this way, the electrical signal can activate the BAT proximate to the device by stimulating the nerves innervating the BAT and/or by stimulating brown adipocytes directly. As mentioned above, two or more transcutaneous devices, same or different from one another, can be simultaneously applied to a patient, proximate to the same BAT depot or to different BAT depots. Although a patient can have two or more transcutaneously applied devices and although the devices can be configured to simultaneously deliver electrical signals to BAT, the devices can be configured such that only one delivers an electrical signal at a time. As also mentioned above, a transcutaneous device can be rotated to different BAT depots of a patient and deliver an electrical signal to each of the BAT depots. Rotating a device between two or more different locations on a patient's body and/or removing a device from a patient when not in use can help prevent nerve desensitization and/or dysfunction, can help reduce any adverse effects of a device's attachment to the body, e.g., irritation from an adhesive applying a device to skin, and/or can help stimulate creation or replication of new BAT in multiple locations on a patient's body. For non-limiting example, the device can be placed in varying positions on the body to modulate the activity of different regions of BAT. In one embodiment, the device can be worn on one side of the neck, e.g., the left side, for a period of time and then on an opposite side of the neck, e.g., the right side, for the next time period, etc. In another embodiment, the device can be worn on an anterior side of a BAT depot, e.g., front of a left shoulder on one side of the patient's coronal plane, for a period of time and then on an opposite, posterior side of the BAT depot, e.g., back of the left shoulder on the opposite side of the patient's coronal plane, for the next period of time. In yet another embodiment, illustrated in FIG. 11, a device 10 can be worn proximate a BAT depot on one of a left and right side of a sagittal plane P in a supraclavicular region of a body 12 for a period of time and then the device 10 can be worn on the other of the left and right sides of the sagittal plane P in the supraclavicular region proximate to another BAT depot for the next period of time. Although the same device 10 is shown in FIG. 11 as being sequentially relocated to different tissue surface or skin positions on the body 12, as discussed herein, one or both of the devices can be implanted and/or two separate devices can be used with a patient such that a first device is positioned at one location and a second device is positioned at a second, different location.

Figure 12:
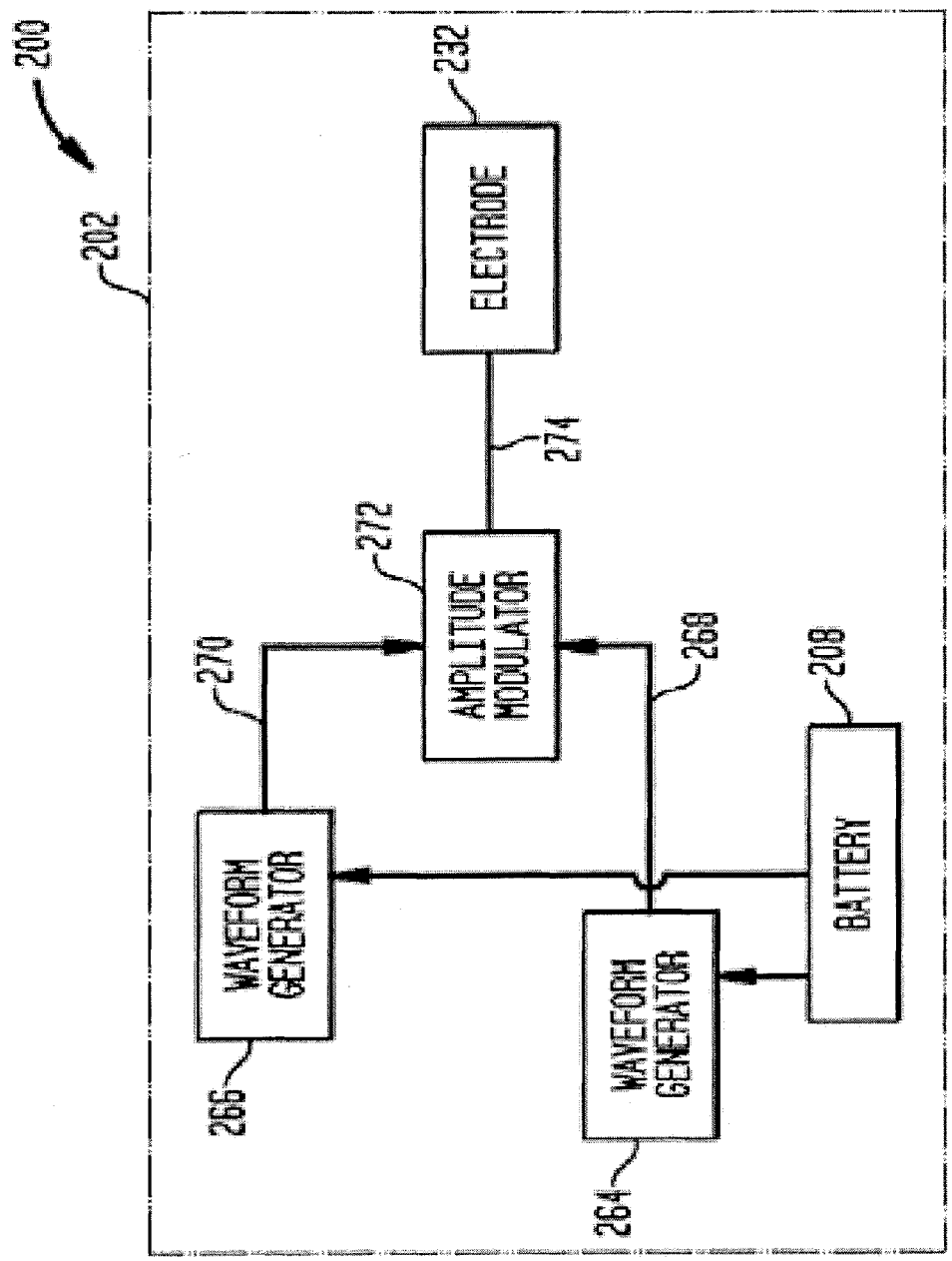
FIG. 12 is a schematic view of one embodiment of a transcutaneous device for stimulating BAT.

FIG. 12 illustrates one exemplary embodiment of a transcutaneous device 200 in the form of a selective nerve stimulation patch housing configured to generate and deliver an electrical signal to tissue such as BAT. The device 200 includes a circuitized substrate 202 configured to generate electrical signals for stimulating tissue such as BAT. The device 200 can include a suitable power source or battery 208, e.g., a lithium battery, a first waveform generator 264, and a second waveform generator 266. The first and second waveform generators 264, 266 can be electrically coupled to and powered by the battery 208. The waveform generators 264, 266 can be of any suitable type, such as those sold by Texas Instruments of Dallas, Tex. under model number NE555. The first waveform generator 264 can be configured to generate a first waveform or low frequency modulating signal 268, and the second waveform generator 266 can be configured to generate a second waveform or carrier signal 270 having a higher frequency than the first waveform 268. As discussed herein, such low frequency modulating signals cannot, in and of themselves, pass through body tissue to effectively stimulate target nerves. The second waveform 270 can, however, to overcome this problem and penetrate through body tissue. The second waveform 270 can be applied along with the first waveform 268 to an amplitude modulator 272, such as the modulator having the designation On-Semi MC1496, which is sold by Texas Instruments.

Figure 13:
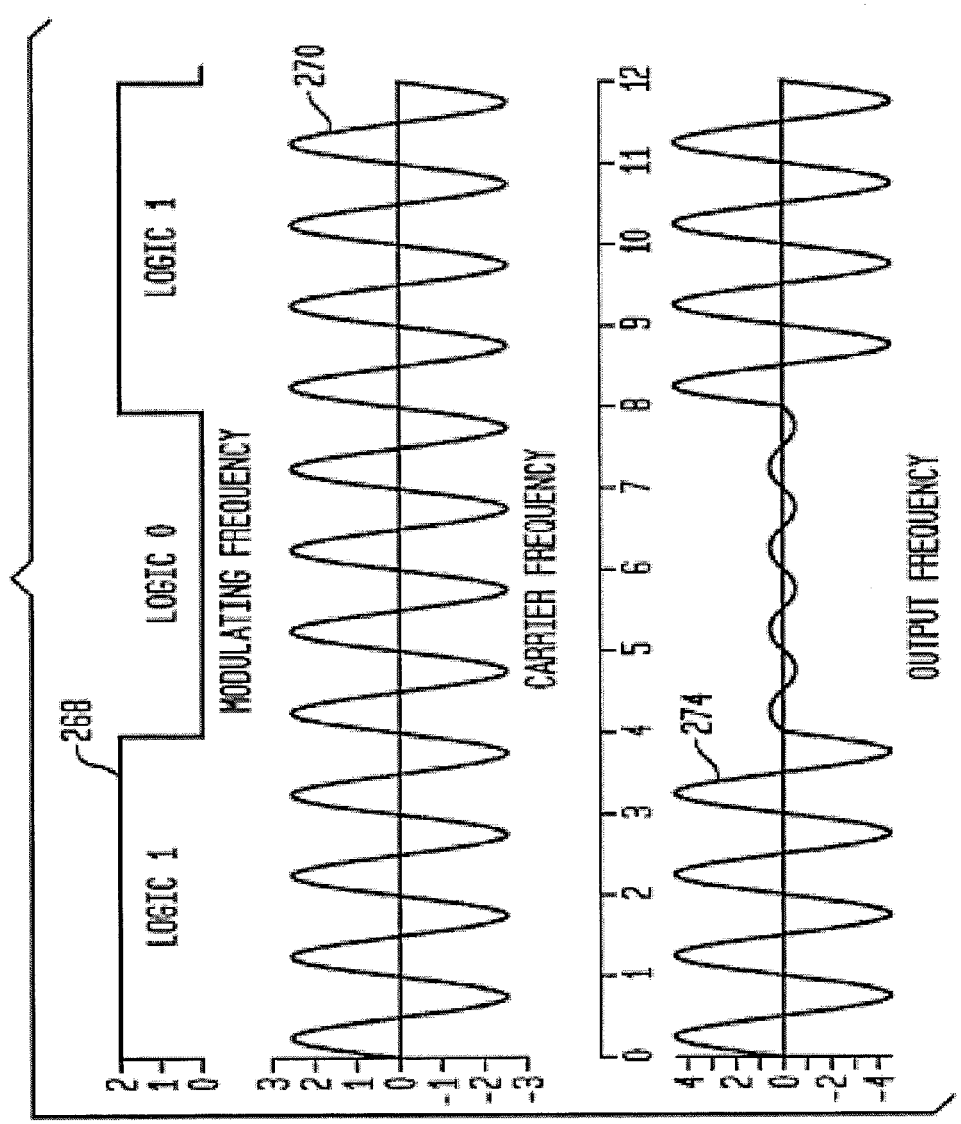
FIG. 13 is a plurality of graphs showing exemplary waveforms generated by the transcutaneous device of FIG. 12.
Figure 14:
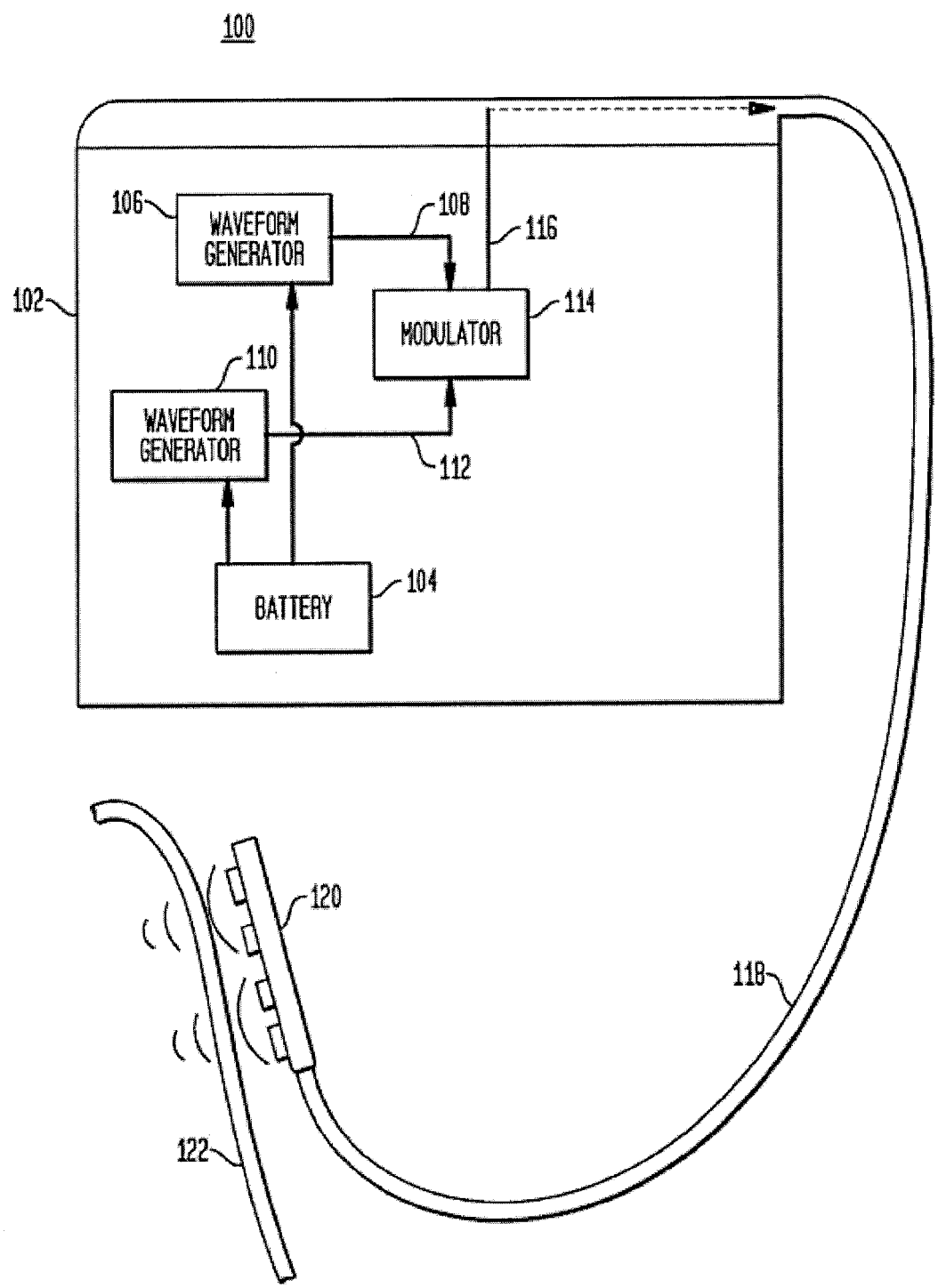
FIG. 14 is a schematic view of one embodiment of an implantable device for stimulating BAT.

The modulator 272 can be configured to generate a modulated waveform 274 that is transmitted to one or more electrodes 232 accessible at a bottom surface of the circuitized substrate 202. Although FIG. 12 shows only one electrode 232, the device 200 can include two or more electrodes. The electrodes 232 can be configured to, in turn, apply the modulated waveform 274 to a target nerve to stimulate the target nerve. As illustrated in FIGS. 12 and 13, the first waveform 268 can be a square wave, and the second waveform 270 can be a sinusoidal signal. As will be appreciated by a person skilled in the art, modulation of the first waveform 268 with the second waveform 270 can results in a modulated waveform or signal 274 having the configuration shown in FIG. 13. Although the signals in FIG. 14 are illustrated as being biphasic, the signals can be monophasic.

The transcutaneous device used to transcutaneously activate BAT can have a variety of sizes, shapes, and configurations. Generally, the device can be configured to generate and/or deliver an electrical signal to tissue at predetermined intervals, in response to a manual trigger by the patient or other human, in response to a predetermined trigger event, or any combination thereof. As will be appreciated by a person skilled in the art, and as discussed in more detail above and in U.S. Patent Publication No. 2009/0093858 filed Oct. 3, 2007 and entitled "Implantable Pulse Generators And Methods For Selective Nerve Stimulation," the body attenuates low frequency signals requiring a high frequency signal for transdermal passage. This high-frequency or carrier signal, in conjunction with a modulating low frequency wave can be applied by the transcutaneous device to stimulate the nerves innervating BAT for WA or other lipid consumption leading to loss of body fat and body weight.

Various exemplary embodiments of transcutaneous devices configured to apply an electrical signal or other stimulation means to stimulate nerves are described in more detail in U.S. Patent Publication No. 2009/0132018 filed Nov. 16, 2007 and entitled "Nerve Stimulation Patches And Methods For Stimulating Selected Nerves," U.S. Patent Publication No. 2008/0147146 filed Dec. 19, 2006 and entitled "Electrode Patch And Method For Neurostimulation," U.S. Patent Publication No. 2005/0277998 filed Jun. 7, 2005 and entitled "System And Method For Nerve Stimulation," U.S. Patent Publication No. 2006/0195153 filed Jan. 31, 2006 and entitled "System And Method For Selectively Stimulating Different Body Parts," U.S. Patent Publication No. 2007/0185541 filed Aug. 2, 2006 and entitled "Conductive Mesh For Neurostimulation," U.S. Patent Publication No. 2006/0195146 filed Jan. 31, 2006 and entitled "System And Method For Selectively Stimulating Different Body Parts," U.S. Patent Publication No. 2008/0132962 filed Dec. 1, 2006 and entitled "System And Method For Affecting Gastric Functions," U.S. Patent Publication No. 2008/0147146 filed Dec. 19, 2006 and entitled "Electrode Patch And Method For Neurostimulation," U.S. Patent Publication No. 2009/0157149 filed Dec. 14, 2007 and entitled "Dermatome Stimulation Devices And Methods," U.S. Patent Publication No. 2009/0149918 filed Dec. 6, 2007 and entitled "Implantable Antenna," U.S. Patent Publication No. 2009/0132018 filed Nov. 16, 2007 and entitled "Nerve Stimulation Patches And Methods For Stimulating Selected Nerves," U.S. patent application Ser. No. 12/317,193 filed Dec. 19, 2008 and entitled "Optimizing The Stimulus Current In A Surface Based Stimulation Device," U.S. patent application Ser. No. 12/317,194 filed Dec. 19, 2008 and entitled "Optimizing Stimulation Therapy Of An External Stimulating Device Based On Firing Of Action Potential In Target Nerve," U.S. patent application Ser. No. 12/407,840 filed Mar. 20, 2009 and entitled "Self-Locating, Multiple Application, And Multiple Location Medical Patch Systems And Methods Therefor," U.S. patent application Ser. No. 12/605,409 filed Oct. 26, 2009 and entitled "Offset Electrodes."

In an exemplary embodiment, the transcutaneous device can include an electrical stimulation patch configured to be applied to an external skin surface and to deliver an electrical signal to tissue below the skin surface, e.g., to underlying BAT. The patch can be configured to generate its own electrical signal with a signal generator and/or to deliver an electrical signal received by the patch from a source in electronic communication with the patch. The device can be wireless and be powered by an on-board and/or external source, e.g., inductive power transmission. The patch can be attached to the skin in any way, as will be appreciated by a person skilled in the art. Non-limiting examples of patch application include using a skin adhesive locally (e.g., on patch rim), using a skin adhesive globally (e.g., on skin-contacting surfaces of the patch), using an overlying support (e.g., gauze with taped edges), using an adherent frame allowing interchangeability (e.g., a brace or an article of clothing), being subdermally placed with wireless connectivity (e.g., Bluetooth) or transdermal electrodes, and using any combination thereof. Electrodes can include receiver circuitry configured to interact with a controller in electronic communication with the electrodes such that the controller can control at least some functions of the electrodes, e.g., on/off status of the electrodes and adjustment of parameters such as amplitude, frequency, length of train, etc.

In use, and as mentioned above, an electrical stimulation patch can be worn continuously or intermittently as needed. In a transcutaneous application, a patch such as one described in previously mentioned U.S. Patent Publication No. 2009/0132018, can be designed to transmit through the skin using a dual waveform approach employing a first waveform designed to stimulated a nerve coupled with a high frequency carrier waveform. The patch can be placed proximate to a BAT depot, such as over the left supraclavicular region of the patient's back, for a predetermined amount of time, e.g., twelve hours, one day, less than one week, seven days (one week), one month (four weeks), etc., and can continuously deliver an electrical signal to the BAT. As mentioned above, the BAT depot can be identified by scanning the patient prior to application of the patch proximate to the BAT depot. Seven days is likely the longest period an adhesive can be made to stick to the skin of a patient without modification and can thus be a preferable predetermined amount of time for patches applied to skin with an adhesive. After the predetermined amount of time, the patch can be removed by a medical professional or the patient, and the same patch, or more preferably a new patch, can be placed, e.g., on the right supraclavicular region of the patient's back for another predetermined amount of time, which can be the same as or different from the predetermined amount of time as the first patch applied to the patient. This process can be repeated for the duration of the treatment, which can be days, weeks, months, or years. In some embodiments, the process can be repeated until occurrence of at least one threshold event, e.g., a predetermined amount of time, a predetermined physiological effect such as a predetermined amount of weight lost by the patient, etc. If the same patch is relocated from a first region, e.g., the left supraclavicular region, to a second region, right supraclavicular region, the patch can be reconditioned after removal from the first region and prior to placement at the second region. Reconditioning can include any one or more actions, as will be appreciated by a person skilled in the art, such as replacing one or more patch components, e.g., a battery, an adhesive, etc.; cleaning the patch; etc.

To more accurately simulate a weight loss surgery that has a continuous or chronic effect on a patient for an extended period of time, the patch can be placed on a patient and continuously or chronically deliver an electrical signal thereto for an extended, and preferably predetermined, amount of time. In an exemplary embodiment, the predetermined amount of time can be at least four weeks. The electrical signal can be delivered to same BAT depot for the predetermined amount of time, or two or more different BAT depots can be stimulated throughout the predetermined amount of time, e.g., left and right supraclavicular regions being stimulated for alternate periods of seven days to total one month of predetermined time. Continued or chronic nerve stimulation to activate BAT can increase BAT energy expenditure over time and potentially induce more or faster weight loss than periodic or intermittent nerve stimulation. The electrical signal can be the same or can vary during the amount of time such that the electrical signal is continuously and chronically applied to the patient to provide 24/7 treatment mimicking the 24/7 consequences of surgery. The continuous amount of time the patient is electrically stimulated can be a total amount of continuous activation of any one BAT depot (e.g., activation of a single BAT depot), sequential activation of two or more BAT depots, simultaneous activation of two or more BAT depots, or any combination thereof. A total amount of time of sequential activation of different BAT depots can be considered as one extended amount of time despite different areas of BAT activation because activation of one BAT depot may cause the brain to signal for BAT activation in other BAT depots.

Generally, direct activation of BAT can include implanting a device below the skin surface proximate to a BAT depot, e.g., within a BAT depot, and activating the device to deliver an electrical signal to the nerves innervating the BAT depot and/or to brown adipocytes directly. BAT itself is densely innervated, with each brown adipocyte being associated with its own nerve ending, which suggests that stimulating the BAT directly can target many if not all brown adipocytes and depolarize the nerves, leading to activation of BAT. The sympathetic nerves that innervate BAT can be accessed directly through standard surgical techniques, as will be appreciated by a person skilled in the art. The device can be implanted on a nerve or placed at or near a nerve cell's body or perikaryon, dendrites, telodendria, synapse, on myelin shelth, node of Ranvier, nucleus of Schwann, or other glial cell to stimulate the nerve. While implanting such a device can require a surgical procedure, such implantation is typically relatively short, outpatient, and with greatly reduced risks from longer and more complicated surgical procedures such as gastric bypass. In an exemplary embodiment, a stimulation device with at least two electrodes can be at least partially implanted in the patient, and more preferably entirely within the patient. A person skilled in the art will appreciate that any number of electrodes, e.g., one or more, can be at least partially implanted in the patient. The leads of the at least one electrode can be implanted in a location sufficiently close to the nerves innervating the BAT so that when activated, the signal sent through the at least one electrode is sufficiently transferred to adjacent nerves, causing these nerves to depolarize. As mentioned above, electrodes can include receiver circuitry configured to interact with a controller in electronic communication with the electrodes such that the controller can control at least some functions of the electrodes, e.g., on/off status of the electrodes and adjustment of parameters such as amplitude, frequency, length of train, etc.

FIG. 14 illustrates one exemplary embodiment of an implantable device 100 configured to generate and deliver an electrical signal to tissue such as BAT. The implantable device 100 can include a housing 102 coupled to a suitable power source or battery 104, such as a lithium battery, a first waveform generator 106, and a second waveform generator 108. As in the illustrated embodiment, the battery 104 and first and second waveform generators can be located within the housing 102. In another embodiment, a battery can be external to a housing and be wired or wirelessly coupled thereto. The housing 102 is preferably made of a biocompatible material. The first and second waveform generators 106, 108 can be electrically coupled to and powered by the battery 104. The waveform generators 106, 108 can be of any suitable type, such as those sold by Texas Instruments of Dallas, Tex. under model number NE555. The first waveform generator 106 can be configured to generate a first waveform or low frequency modulating signal 108, and the second waveform generator 110 can be configured to generate a second waveform or carrier signal 112 having a higher frequency than the first waveform 108. As discussed herein, such low frequency modulating signals cannot, in and of themselves, pass through body tissue to effectively stimulate target nerves. The second waveform 108 can, however, to overcome this problem and penetrate through body tissue. The second waveform 112 can be applied along with the first waveform 108 to an amplitude modulator 114, such as the modulator having the designation On-Semi MC1496, which is sold by Texas Instruments.

Figure 15:
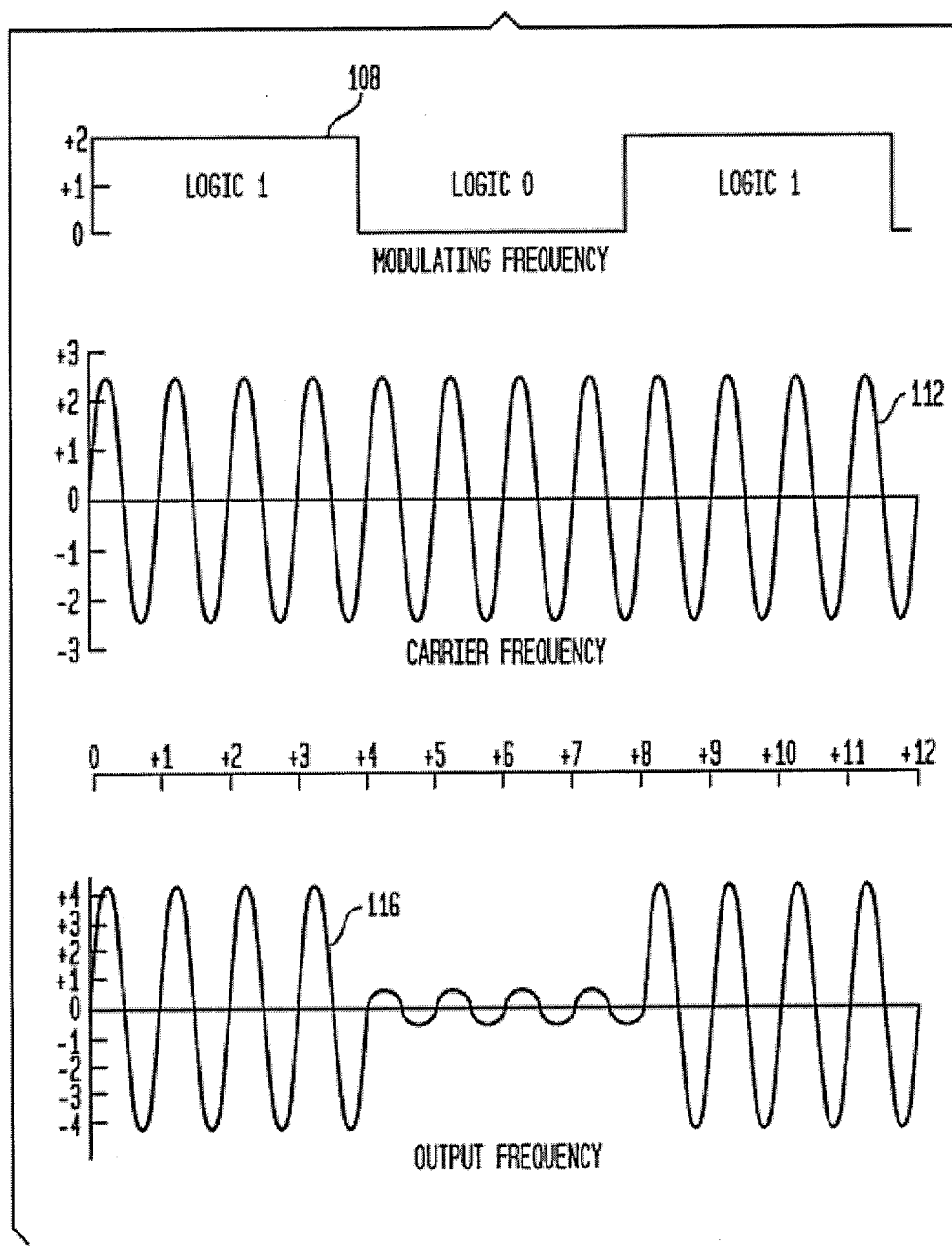
FIG. 15 is a plurality of graphs showing exemplary waveforms generated by the implantable device of FIG. 14.

The modulator 114 can be configured to generate a modulated waveform 116 that is transmitted through a lead 118 to one or more electrodes 120. Four electrodes are illustrated, but the device 100 can include any number of electrodes having any size and shape. The lead 118 can be flexible, as in the illustrated embodiment. The electrodes 120 can be configured to, in turn, apply the modulated waveform 116 to a target nerve 122 to stimulate the target nerve 122. As illustrated in FIGS. 14 and 15, the first waveform 108 can be a square wave, and the second waveform 112 can be a sinusoidal signal. As will be appreciated by a person skilled in the art, modulation of the first waveform 108 with the second waveform 112 can result in a modulated waveform or signal 116 having the configuration shown in FIG. 10.

If an electrode is implanted under a patient's skin, a waveform transmitted to the implanted electrode can include a modulating signal but not include a carrier signal because, if the implanted electrode is sufficiently near a BAT depot, the modulating signal alone can be sufficient to stimulate the target. The waveform transmitted to an implanted electrode can, however, include both a modulating signal and a carrier signal.

Various exemplary embodiments of devices configured to directly apply an electrical signal to stimulate nerves are described in more detail in U.S. Patent Publication No. 2005/0177067 filed Jan. 26, 2005 and entitled "System And Method For Urodynamic Evaluation Utilizing Micro-Electronic Mechanical System," U.S. Patent Publication No. 2008/0139875 filed Dec. 7, 2006 and entitled "System And Method For Urodynamic Evaluation Utilizing Micro Electro-Mechanical System Technology," U.S. Patent Publication No. 2009/0093858 filed Oct. 3, 2007 and entitled "Implantable Pulse Generators And Methods For Selective Nerve Stimulation," U.S. Patent Publication No. 2010/0249677 filed Mar. 26, 2010 and entitled "Piezoelectric Stimulation Device," U.S. Patent Publication No. 2005/0288740 filed Jun. 24, 2004 and entitled, "Low Frequency Transcutaneous Telemetry To Implanted Medical Device," U.S. Pat. No. 7,599,743 filed Jun. 24, 2004 and entitled "Low Frequency Transcutaneous Energy Transfer To Implanted Medical Device," U.S. Pat. No. 7,599,744 filed Jun. 24, 2004 and entitled "Transcutaneous Energy Transfer Primary Coil With A High Aspect Ferrite Core," U.S. Pat. No. 7,191,007 filed Jun. 24, 2004 and entitled "Spatially Decoupled Twin Secondary Coils For Optimizing Transcutaneous Energy Transfer (TET) Power Transfer Characteristics," and European Patent Publication No. 377695 published as International Patent Publication No. WO1989011701 published Nov. 30, 2004 and entitled "Interrogation And Remote Control Device."

In use, at least one electrode of an implantable electrical stimulation device can be placed in the area of a BAT depot and be coupled to a signal generator. As will be appreciated by a person skilled in the art, the signal generator can have a variety of sizes, shapes, and configurations, and can be external to the patient or implanted therein similar to a cardiac pacemaker. The signal generator can create the electrical signal to be delivered to the BAT and can be on continuously once activated, e.g., manually, automatically, etc. The signal generator can be in electronic communication with a device external to the patient's skin to turn it on and off, adjust signal characteristics, etc. The external device can be positioned near the patient's skin, e.g., using a belt, a necklace, a shirt or other clothing item, furniture or furnishings such as a chair or a pillow, or can be a distance away from the patient's skin, such as a source located elsewhere in the same room or the same building as the patient. The electrical stimulation device can include circuitry configured to control an activation distance, e.g., how close to a power source the electrical stimulation device must be to be powered on and/or begin delivering electrical signals. Correspondingly, the external device can include a transmitter configured to transmit a signal to the electrical stimulation device's circuitry. If implanted, the signal generator can include an internal power source, e.g., a battery, a capacitor, stimulating electrodes, a kinetic energy source such as magnets positioned within wired coils configured to generate an electrical signal within the coils when shaken or otherwise moved, etc. In one embodiment, a battery can include a flexible battery, such as a Flexion battery available from Solicore, Inc. of Lakeland, Fla. In another embodiment, a battery can include an injectable nanomaterial battery. The power source can be configured to be recharged by transcutaneous means, e.g., through transcutaneous energy transfer (TET) or inductive coupling coil, and/or can be configured to provide power for an extended period of time, e.g., months or years, regardless of how long the power source is intended to provide power to the device. In some embodiments, a power source can be configured to provide power for less than an extended period of time, e.g., about 7 days, such as if a battery is replaceable or rechargeable and/or if device real estate can be conserved using a smaller, lower power battery. In some embodiments, the signal generator can include an electrode patch onboard configured to generate a pulse, thereby eliminating a need for a battery.

The signal generator, and/or any other portion of the device or external device, as will be appreciated by a person skilled in the art, can be configured to measure and record one or more physical signals relating to the activation of BAT. For non-limiting example, the physical signals can include voltage, current, impedance, temperature, time, moisture, salinity, pH, concentration of hormones or other chemicals, etc. The recorded physical signals can be presented to the patient's physician for evaluation of system performance and efficacy of brown adipose activation. Also, the recorded physical signals can be used in a closed-loop feedback configuration to allow the device, e.g., the controller, to dynamically adjust the electrical signal settings used for treatment.

Surgical Interventions

While the pathogenesis of obesity is often multifactorial, the fundamental cause lies in a caloric (i.e., food or nutrient) intake that is disproportionately high relative to the energy expenditure. Excess calories result in increased fat storage within adipose tissue and/or increased adipose tissue production. The sustained loss of fat stored in adipose tissue or the sustained loss of such adipose tissue itself can reduce and even eliminate the dire consequences of obesity. Typically, restricting total caloric intake either alone or in combination with increasing energy expenditure through, for example, increased exercise, results in reduced adipose tissue.

Despite the simplicity of the solution, sustained weight loss in overweight and obese individuals remains extraordinarily difficult, particularly for the patient with obesity. Treatment strategies range from diet and exercise regimens, behavioral modification techniques, to surgical intervention such as gastric bypass and mechanical devices such as jaw wiring, waist cords, and balloons.

Some surgical procedures have demonstrated significant weight loss results in patients. Bariatric surgical procedures have been developed to reduce the accessible volume within the stomach. One such procedure is a gastric bypass. Gastric bypass first divides the stomach into a small upper pouch and a much larger, lower "remnant" pouch and then re-arranges the small intestine to allow both pouches to stay connected to it. All gastric bypass procedures lead to a marked reduction in the functional volume of the stomach. The most commonly employed gastric bypass technique is Roux-en-Y gastric bypass (RYGB). The RYGB is an effective clinical therapy for the treatment of metabolic disease. The small bowel is divided below the lower stomach outlet and re-arranged into a Y-configuration to enable outflow of food from the small upper stomach pouch, via a "Roux limb." RYGB has been shown to produce sustained and consistent weight loss in patient and in rodent models. However, the mechanisms through which RYGB produces its altered physiological and psychological effects remain poorly understood.

Another early restrictive type surgical procedures was the so-called "stomach stapling" operation in which a row of horizontal staples can be placed horizontally across the upper stomach and then several staples can be removed from the staple line to create an opening for a small amount of food, but not too much food. This procedure is mostly restrictive, leading to an early feeling of satiety. Other surgical procedures to treat severe obesity can include gastrectomies (removal of all or a portion of the stomach) and vertical sleeve gastrectomy and biliopancreatic diversion with or without a duodenal switch.

Other minimally invasive procedures and devices which create a feeling of early satiety have been introduced into the marketplace to reduce the invasive nature inherent in gastric bypass. The adjustable gastric banding is a band that encircles the stomach at the region of the fundus-cardia junction; it is a restrictive procedure similar to stomach stapling. The adjustable gastric handing is less invasive than the RYBG procedure and potentially reversible. Other minimally invasive procedures and devices can include intragastric balloon therapy, gastric plication and other forms of gastric volume reduction (see also US Patent Application Publication No. 2009/0024144, which is herein incorporated by reference), vertical banded gastroplasty, Magenstrasse and Mill, small bowel transposition (or interposition), biliary diversion, duodenal-jejunal bypass, duodenal endoluminal barrier and variations of these procedures.

Unfortunately, not all patients experience weight loss after surgical intervention. Failure to lose weight after gastric bypass has been categorized mainly as due to mechanical (medical complications) or metabolic reasons (eating behaviors). However, there are some patients that do not achieve successful weight loss despite successful surgical procedures and proper dietary behaviors. Therefore, other non-mechanical or non-behavior factors must be considered, such as genetic and biochemical factors.

The murine models in the Example reveals a physiological link between surgical intervention and a role for MC4R signaling to induce weight loss. Example 1 demonstrates that when mice lack MC4R (MCR4−/−) pathway activation and undergo RYGB surgery, weight increases over time similar to wildtype animals receiving no treatment and in contrast to wildtype animals that undergo RYGB surgery. The data demonstrates that loss of MC4R signaling prevents Weight loss even when metabolic restrictions are imposed. Therefore, to experience the full effects from surgical intervention, physiological activation (such as activation of MC4R signaling) needs to occur for weight loss.

One aspect of the invention is directed to a method of determining an appropriate intervention in a subject with a metabolic disorder to induce weight loss. The metabolic disorder can be any condition that is caused or characterized by abnormal energy use or consumption within the body. Some non-limiting examples can be obesity, diabetes, including type II diabetes, insulin-resistance syndrome, and syndrome X, inflammatory and immune disorders, cancer, neurodegenerative disorders, and other disorders of metabolism. The method can include the steps of performing a first intervention on a subject, where the first intervention is non-invasive.

The first intervention can include any of the non-surgical procedures listed above, such as agonist/antagonist therapy, specifically melanocortin-4 receptor agonists, activation of brown adipose tissue and the use of duodenal endoluminal barrier. Furthermore, the first intervention can be temporary. By temporarily performing the first intervention, assessment of the efficacy of the first intervention can be made. Moreover, as the first intervention is temporary and reversible, an evaluation of the efficacy can determine if a second intervention needs to be performed or if the first intervention alone is sufficient to attain the desired result.

The method can further include measuring energy expenditure of the subject to assess the subject's response to the first intervention. Energy expenditure assessments can be performed as outlined above, such as by utilizing indirect measurements including calorimetry, oxygen consumption, carbon dioxide production and/or nitrogen excretion and heat production. Other methods known by those skilled in the art are also be applicable and within the scope of the invention.

In another aspect of the invention, energy expenditure can be a surrogate for measuring the level of melanocortin receptor pathway activation, in particular MC4R pathway activation. Alternatively, melanocortin receptor pathway activation can be measured by detecting markers indicative of melanocortin receptor activation. The markers can include, but are not limited to, biochemical markers, surface markers, mutations, polymorphisms, differential gene expression, differential protein expression and physiological imaging techniques based on PET, magnetic resonance or other technologies.

After determining the energy expenditure or melanocortin pathway activation of the subject as related to the first intervention, a second intervention can be chosen that is appropriate for the subject based on the measured energy expenditure or melanocortin pathway activation. The second intervention can be the same as the first intervention or the second intervention can be a different, more invasive procedure. Such procedures can include agonist/antagonist therapy, activation of brown adipose tissue, or surgical procedures, including but not limited to, gastric bypass, biliopancreatic diversion, vertical sleeve gastrectomy, adjustable gastric banding, vertical banded gastroplasty, intragastric balloon therapy, gastric plication, Magenstrasse and Mill, small bowel transposition, biliary diversion and duodenal endoluminal barrier. Alternatively, the second intervention can be performed or administered in combination with the first intervention to increase energy expenditure or increase melanocortin pathway activation. Moreover, either the first or the second intervention can activate the melanocortin receptor, and in one embodiment both interventions activate the melanocortin receptor.

In another embodiment, the first and/or the second intervention can activate the melanocortin receptor pathway. In particular, the first and/or second intervention can activate the MC3R and/or the MC4R signaling pathway. Moreover, the second intervention can selectively activate the melanocortin receptor pathway in at least one cell in a region of a brain, spinal cord, sympathetic nervous system, parasympathetic nervous system, enteric nervous system, gastrointestinal tract and pancreas.

In a particular embodiment, a method of inducing weight loss in a subject involves performing a first procedure that is expected to achieve some level of weight loss, either by reducing the volume of the stomach or otherwise altering gastrointestinal physiology and/or by activating the MC4R pathway. In one embodiment the first procedure does not involve the delivery to the subject of a therapeutic agent that is expected to activate the MC4R pathway. The first procedure is supplemented with a second procedure that does not involve the delivery to the subject of a therapeutic agent that is expected to activate the MC4R pathway. The second procedure can be, for example, the activation of BAT. BAT can be activated by transcutaneous or direct electrical stimulation of BAT, as explained above and in concurrently filed U.S. Provisional Patent Application No. 61/297,405, entitled "Methods and Devices for Activating Brown Adipose Tissue," which is incorporated by reference herein in its entirety.

In another aspect of the invention, a composition is disclosed for selectively activating melanocortin receptor pathways in a target tissue in a subject to induce weight loss. The composition can include a therapeutic agent that activates melanocortin receptor pathways in a target tissue and a pharmaceutically acceptable carrier. The therapeutic agent can either be formulated for delivery to the target tissue or bound to a carrier molecule that is targeted for delivery to the target tissue where the target tissue can be the brain, the spinal cord, the sympathetic nervous system, the parasympathetic nervous system, the enteric nervous system, the gastrointestinal tract, the pancreas or any other tissue where activation of the melanocortin receptor pathways can induce weight loss.

EXAMPLES

Murine Models

Rat and mouse models of Roux-en-Y gastric bypass have been developed that closely mimic the effects of the human procedure, including substantial and long-lasting weight loss, improvement in insulin signaling, pancreatic beta cell function, glucose homeostasis and diabetes, and improvement in other sequelae of obesity. Rodent models for these studies include rats and mice with high-fat and/or high-carbohydrate diet-induced obesity, e.g., Sprague-Dawley rats, Long-Evans rats and C57BL/6 mice, as well as mutant or otherwise genetically modified rats and mice that exhibit obesity, insulin resistance, diabetes or other metabolic, inflammatory or neoplastic disorders. Details of the methods for Roux-en-Y gastric bypass in rats and the perioperative care of these animals are provided in Stylopoulos et al., "Roux-en-Y Gastric Bypass Enhances Energy Expenditure And Extends Lifespan In Diet-Induced Obese Rats," *Obesity* 17 (1 Oct. 2009), 1839-47. Methods for Roux-en-Y gastric bypass in mice were substantially the same except that the stomach was divided either by placement of a surgical clip or surgically dividing the stomach and suturing closed the divided segments.

Additionally, diet-induced obese C57BL/6 mice (body weight 50 g) underwent Roux-en-Y gastric bypass or sham operation (consisting of laparotomy, intestinal transection and reanastomosis) and maintained for 2 days with parenteral fluids, followed by a clear liquid diet as tolerated for several days and returned to the preoperative diet as tolerated. Animals were maintained on a high-protein, high-carbohydrate diet from weaning until surgery and postoperatively beginning 7-10 days after surgery.

Example 1

Figure 16:
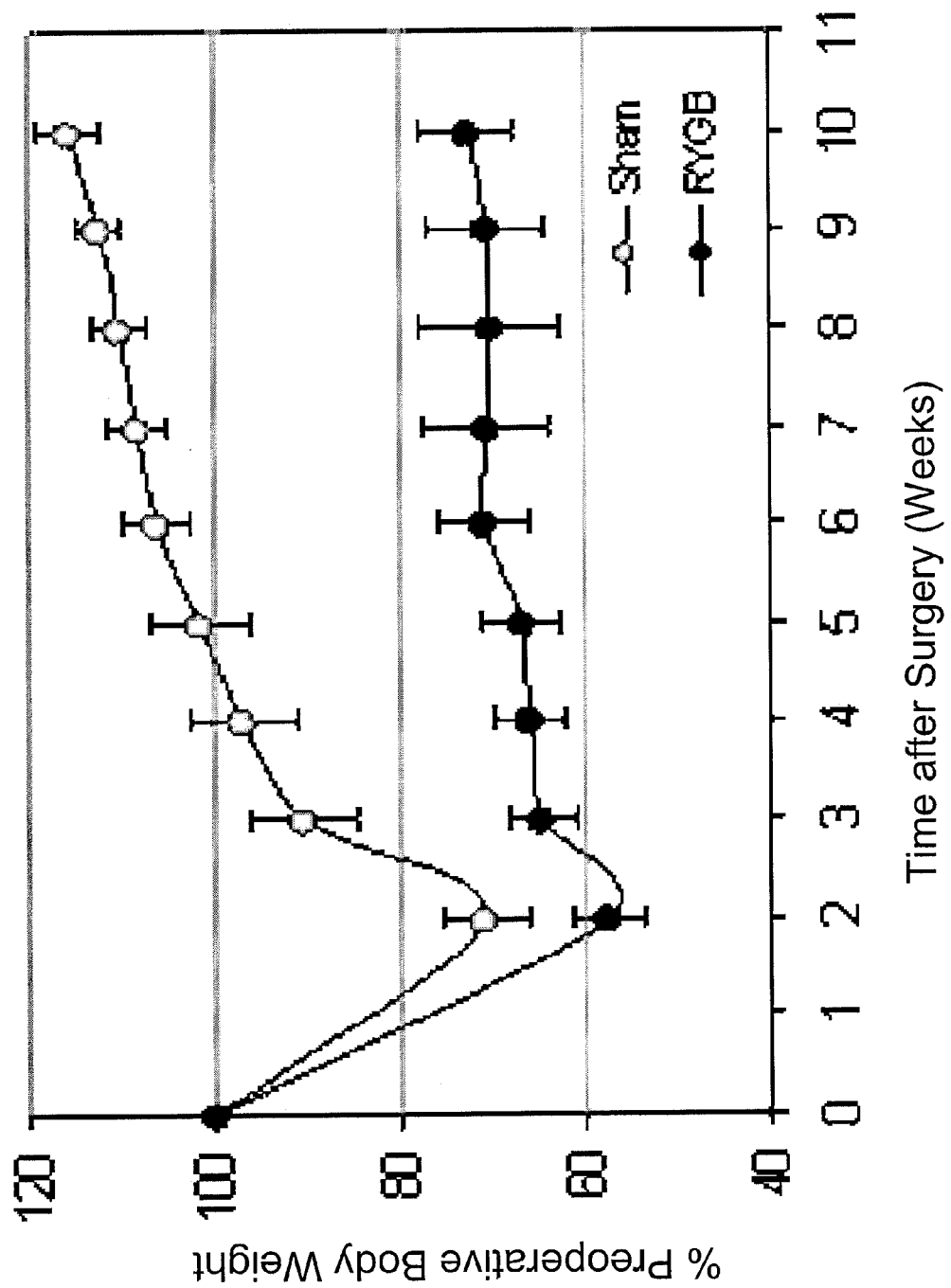
FIG. 16 a graph depicting weight loss in a C57B1/6 mouse model following RYGB surgery as compared to a sham operated animal.
Figure 17:
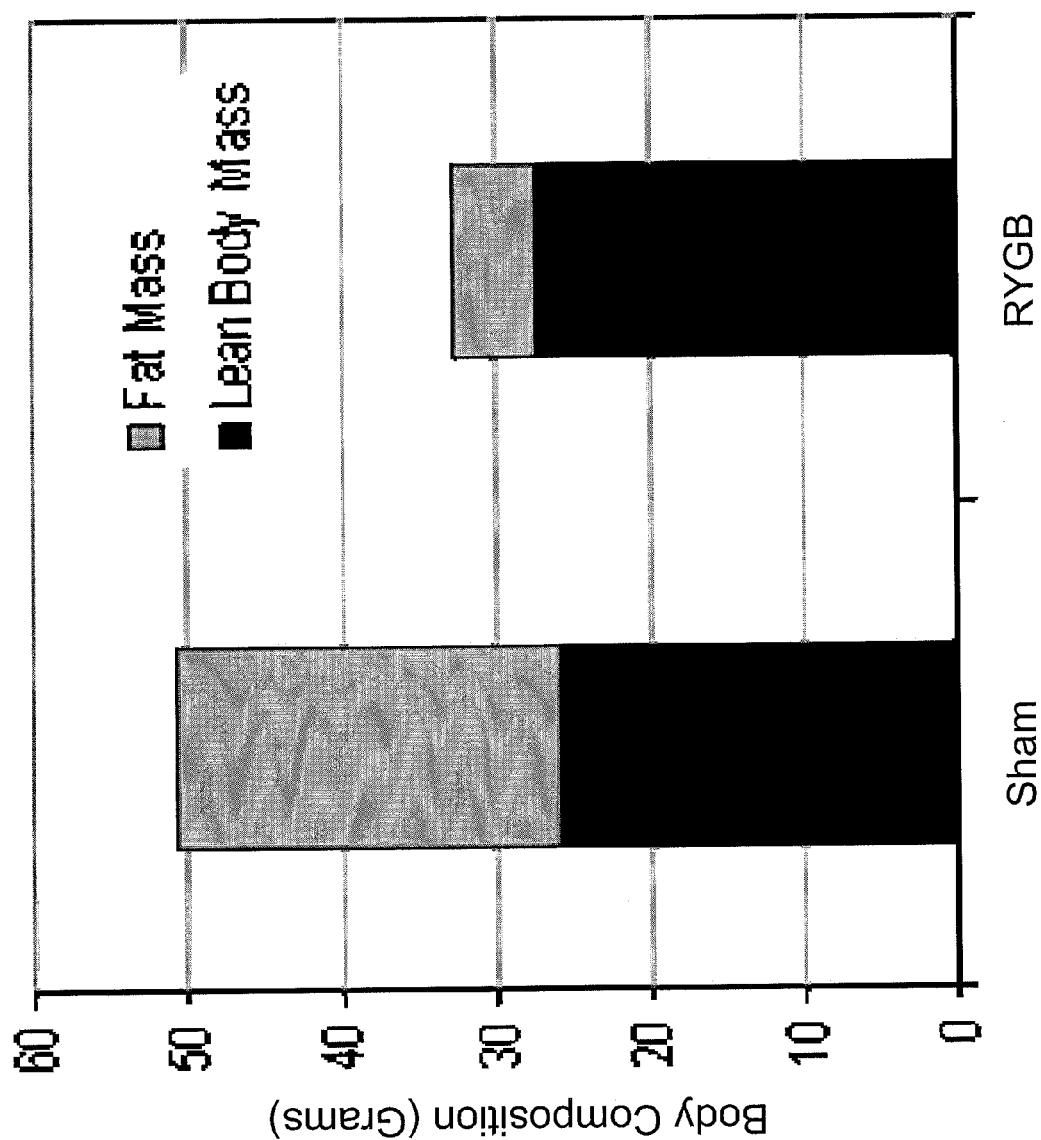
FIG. 17 is a bar graph depicting body composition changes in a C57B1/6 mouse model following RYGB surgery determined by X-ray absorptiometry.

Roux-en-Y gastric bypass (RYGB) has shown to be an effective clinical therapy for the treatment of metabolic disease. FIG. 16 shows body weight plotted as a percentage of the preoperative body weight in rodent animal models that have undergone RYGB. The graph illustrates the sustained and consistent weight loss seen in the models. Moreover, diet-induced obese C57BL/6 mice (average body weight of 50 g) that underwent Roux-en-Y gastric bypass compared to sham operation controls demonstrated decreased body composition as assessed by X-ray absorptiometry 16 weeks after surgery, see FIG. 17.

Figure 18:
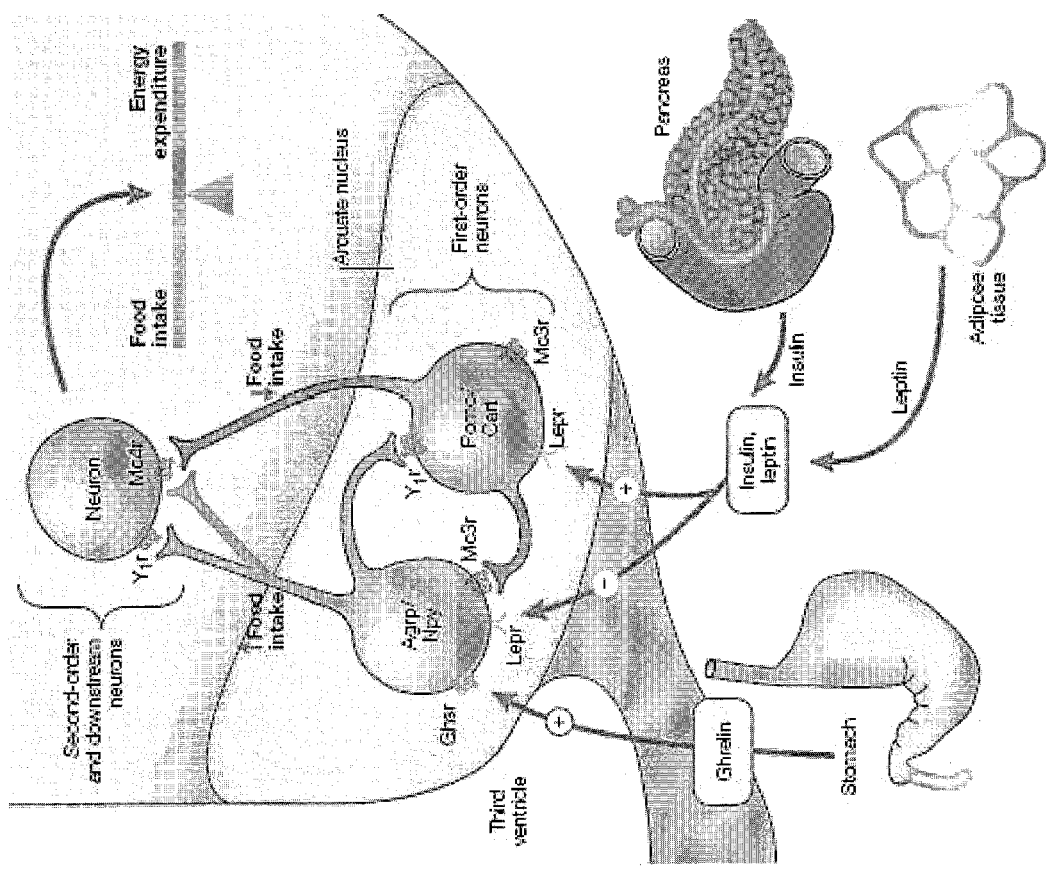
FIG. 18 is an illustration showing critical pathways involved in the regulation of energy balance.
Figure 19:
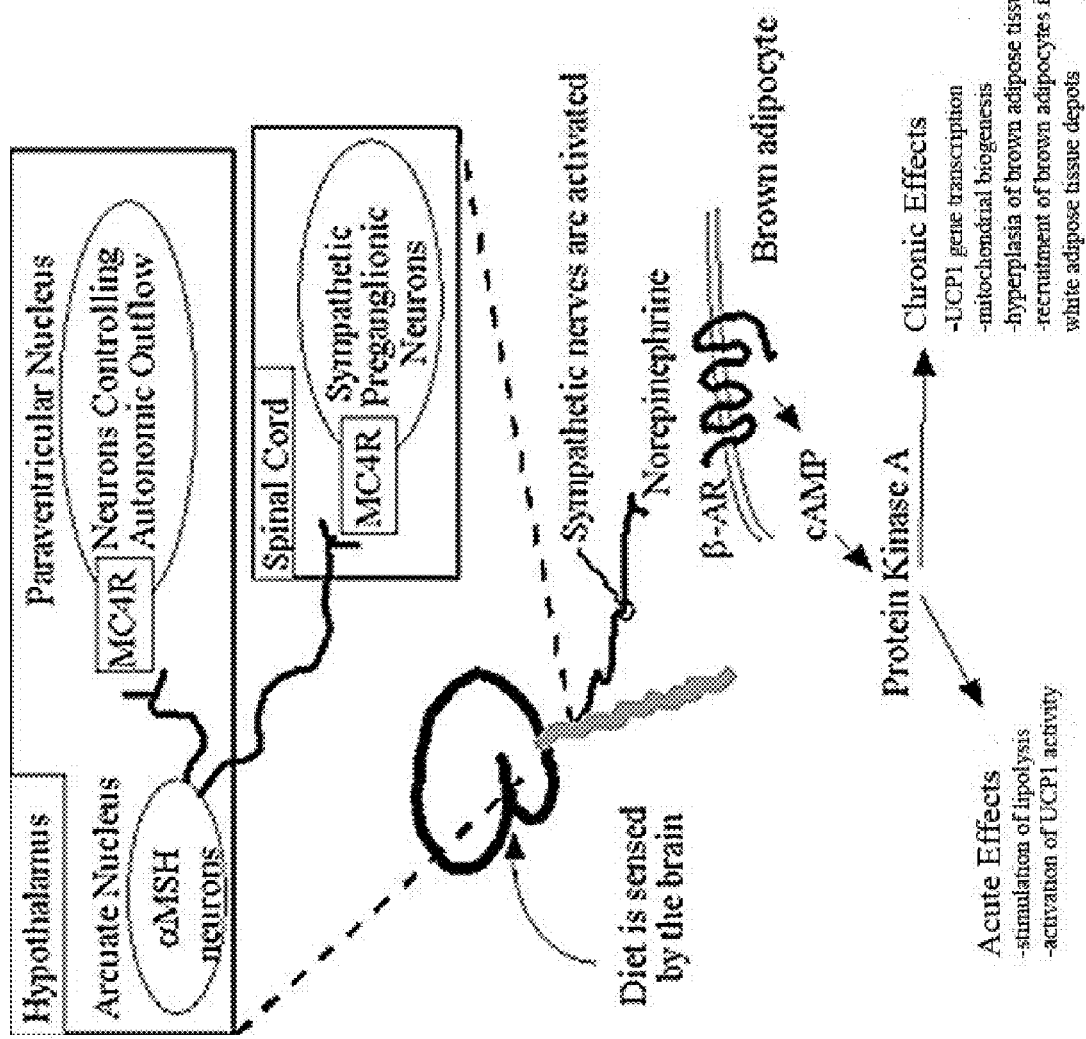
FIG. 19 is an illustration to show MC4R signaling pathway as critical to the regulation of energy expenditure.
Figure 20:
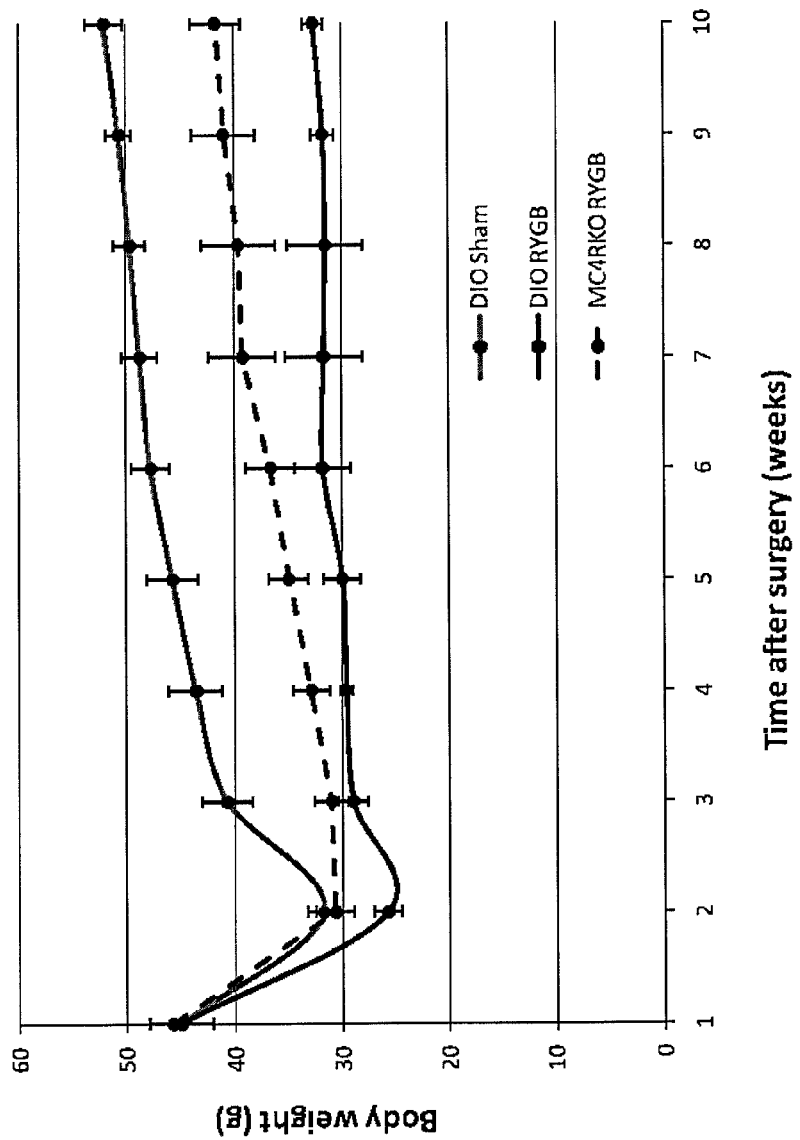
FIG. 20 is a graph showing body weight plotted as a percentage of the preoperative body weight after RYGB surgery in wildtype and MC4R knockout with wildtype sham operated mice as controls.
Figure 21:
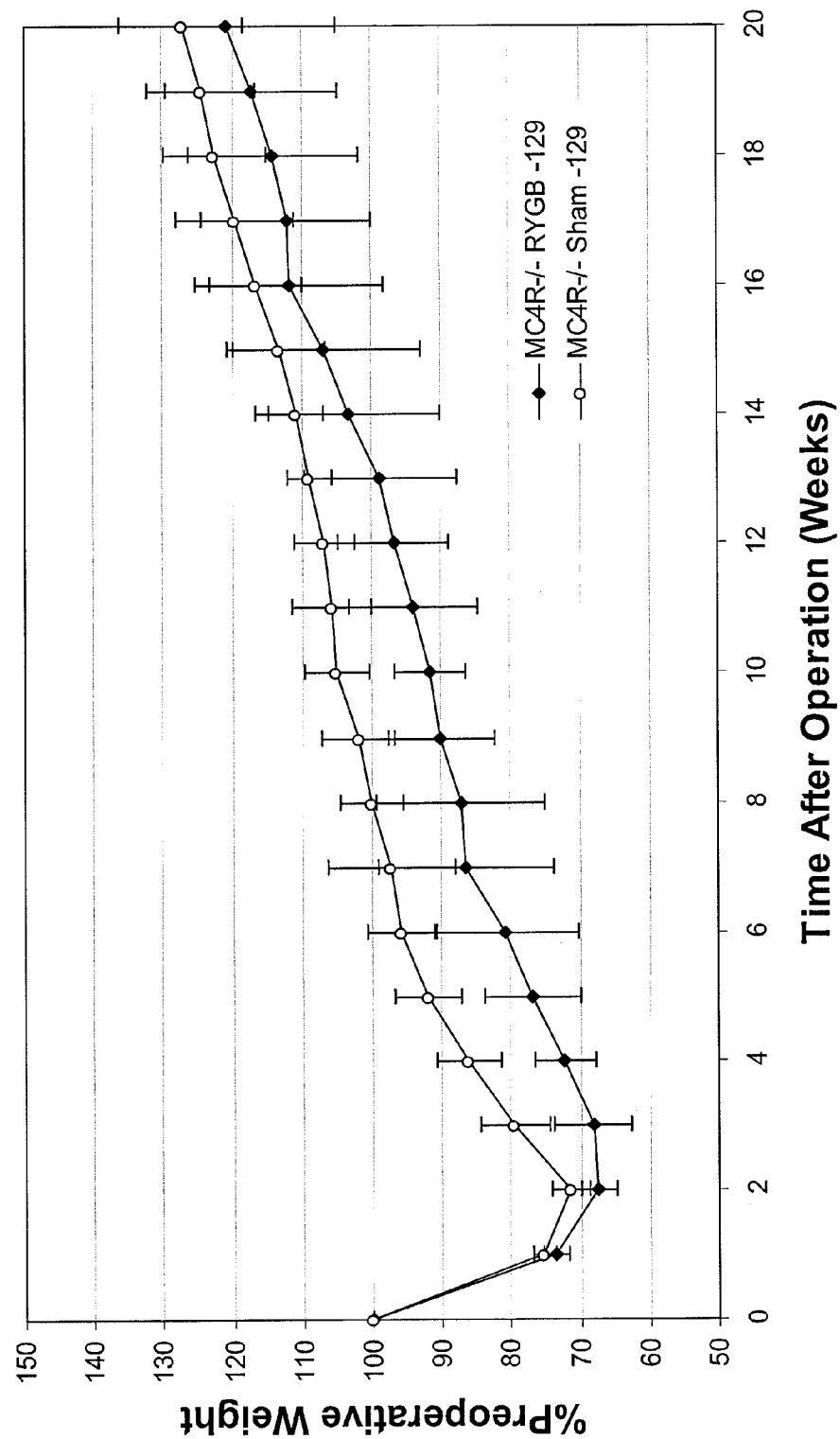
FIG. 21 is a graph showing body weight plotted as a percentage of the preoperative body weight after RYGB surgery in MC4R knockout and MC4R knockout sham operated mice.
Figure 22:
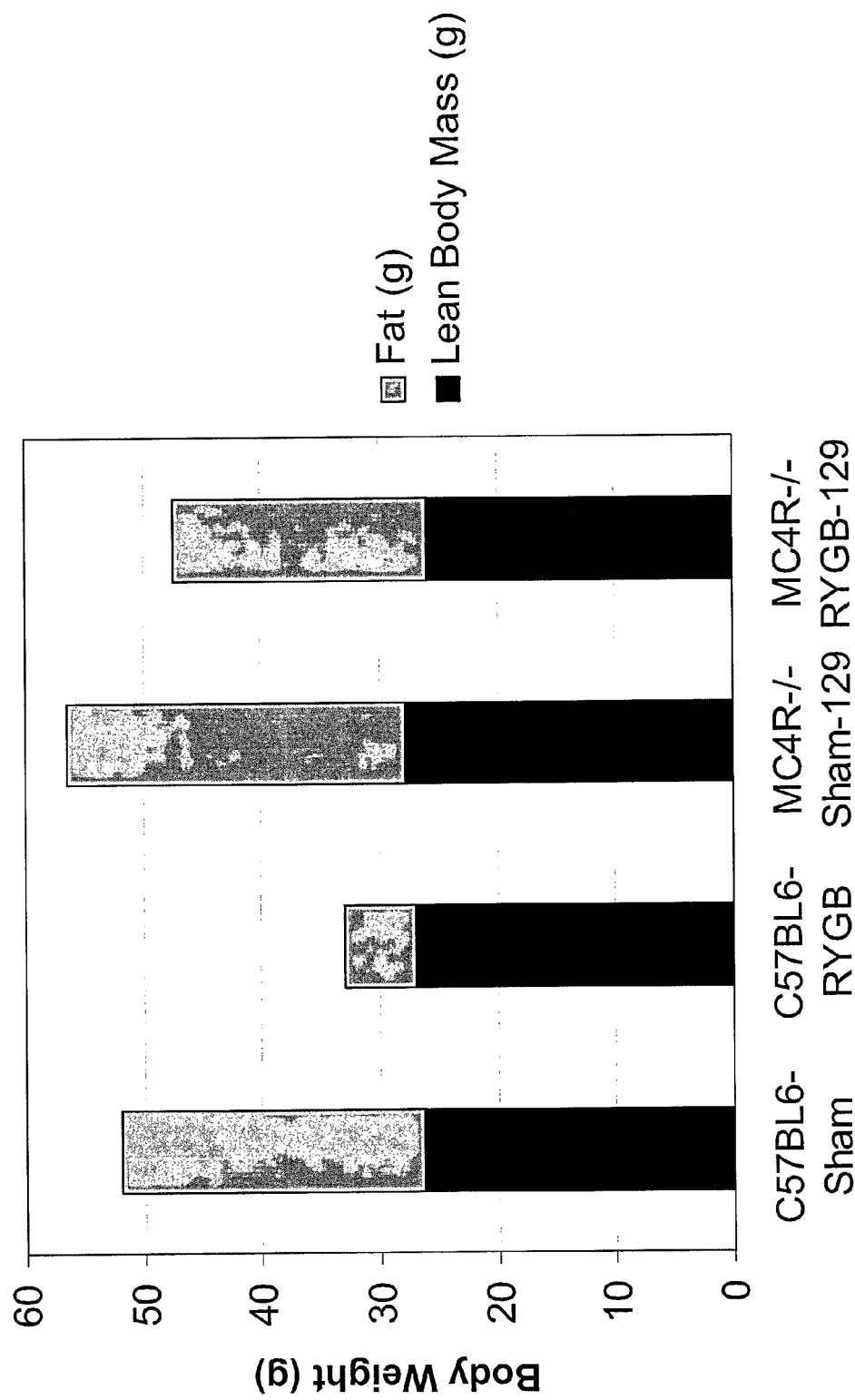
FIG. 22 is a bar graph depicting body composition changes after RYGB surgery in MC4R knockout mice as determined by X-ray absorptiometry.

Given importance of melanocortin receptor signaling in feeding behavior and metabolism (see FIGS. 18 and 19), experiments were designed to investigate mechanisms through which RYGB produces its altered physiological and psychological effects. MC4R knockout mice (body weight >45 g) underwent Roux-en-Y gastric bypass, wildtype RYGB operated mice, wildtype sham operation mice or MC4R knockout sham operation mice according to the protocol used for the experiment shown in FIG. 16 and maintained according to the same postoperative dietary protocol. Body weight was plotted as a percentage of the preoperative body weight in FIG. 20. Weights of MC4R knockout mice that underwent Roux-en-Y gastric bypass or sham operation were directly compared in FIG. 21. Percentage of the preoperative body weight in MC4R knockout mice increased similar to sham operated mice, see FIG. 20 and FIG. 21. The optimal effects of surgery on body weight, food intake, energy expenditure, energy balance and metabolic function thus require MC4R signaling in the brain and/or peripheral sites, and surgery alters MC4R signaling in one or more of these regions FIGS. 18 and 19. Moreover, body composition of MC4R knockout mice that underwent Roux-en-Y gastric bypass or sham operation demonstrated similar fat to lean body mass composition as wildtype diet-induced obese C57BL/6 mice at 20 weeks after surgery, see FIG. 22.

The data demonstrate that melanocortin type 4 receptor (MC4R) signaling is required for the weight loss effects of RYGB surgery and the associated improvement in comorbid disease. The effects of RYGB surgery were reduced by at least 85% when performed in mice with defective signaling through MC4R. These results dispel the notion that results from RYGB are mechanical (i.e., combination of restriction and malabsorption) and demonstrate that physiological weight and metabolic regulatory pathways are modified by this surgical procedure.

Example 2

An additional study to look at the effect of heterozygous mutations was performed. A study population of 1018 individuals who have undergone RYGB surgical intervention was chosen. A total of 971 patients were successfully sequenced for the MC4R gene. After at least 10 months, 845 of the patients were successfully sequenced for the MC4R gene. Patients were sorted into four categories (no MC4R mutations, pathogenic MC4R mutations, non-pathogenic mutations and compound MC4R mutations).

Table 1: Baseline characteristics and measurement of the patients.

TABLE 1

Baseline characteristics and measurement of the patients.

| Characteristic | Pathogenic Heterozygous | Non-pathogenic Heterozygous | Compound Heterozygous | Non-pathogenic Homozygous | No MC4R Variants |
|---|---|---|---|---|---|
| Number | 13 | 46 | 3 | 1 | 908 |
| BMI | 47.4 (4.9) | 49.5 (9.1) | 48.4 (1.3) | 57 | 50.6 (9.2) |
| LDL | 109.9 (36.1) | 112.4 (39.0) | 118.7 (47.0) | 128 | 109.2 (32.2) |
| HDL | 50.4 (11.6) | 46.3 (11.4) | 57.0 (6.3) | 49 | 48.0 (12.3) |
| Diabetes | 69.2% | 43.5% | 33.3% | No | 40.2% |
| Diabetes Rx | 50% | 22.50% | 0% | No | 17.60% |
| Glucose | 149.9 (69.3) | 142.4 (84.4) | 81.0 (16.0) | 114 | 121.7 (53.9) |
| Insulin | 16.5 (8.6) | 22.5 (12.8) | 22.9 (28.1) | 15 | 23.1 (20.2) |
| HbA1c | 6.9 (2.0) | 6.47 (1.27) | 6.3 (0.56) | 5.8 | 6.39 (1.44) |

Figure 23:
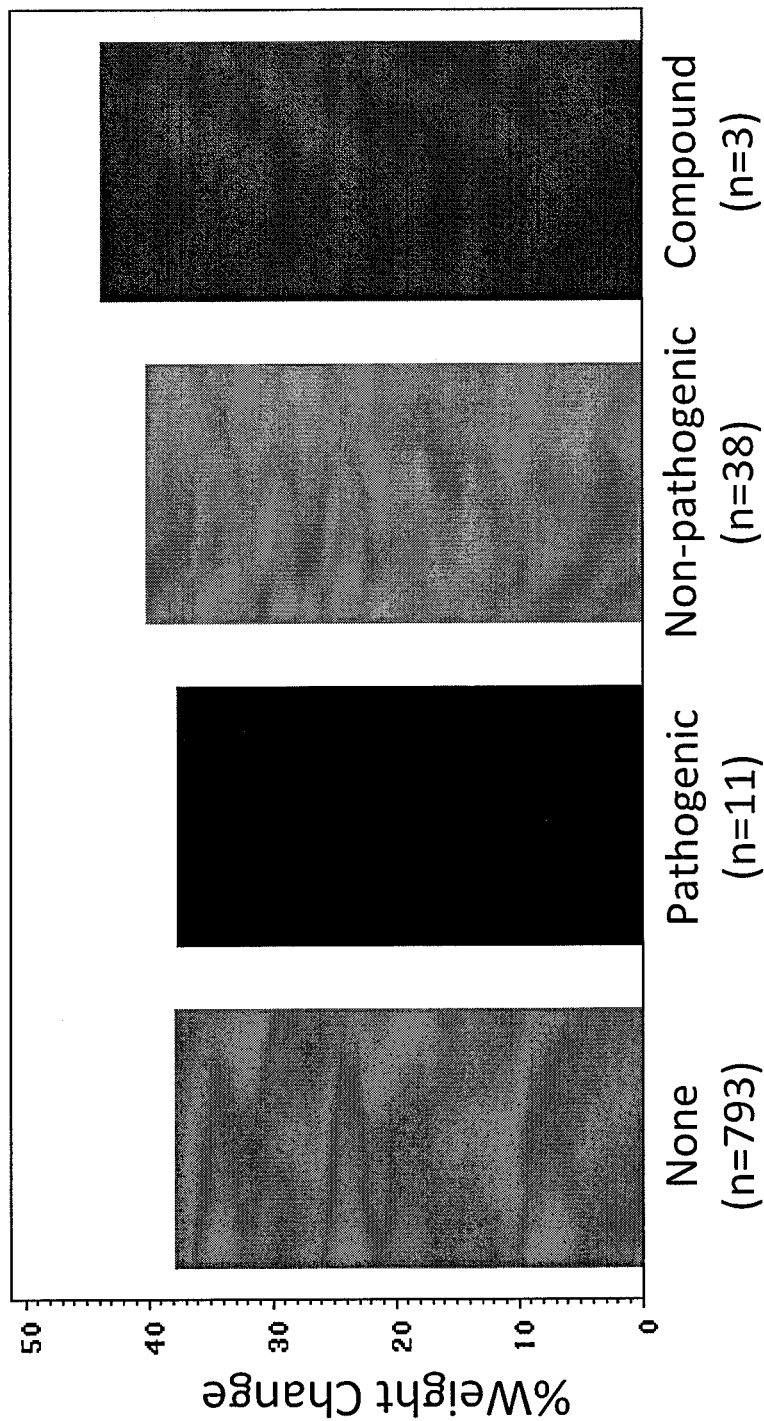
FIG. 23 compares weight change after RYGB surgical intervention in the four groups of patients, i.e. no MC4R mutations, pathogenic MC4R mutations, non-pathogenic mutations and compound MC4R mutations.
Figure 24:
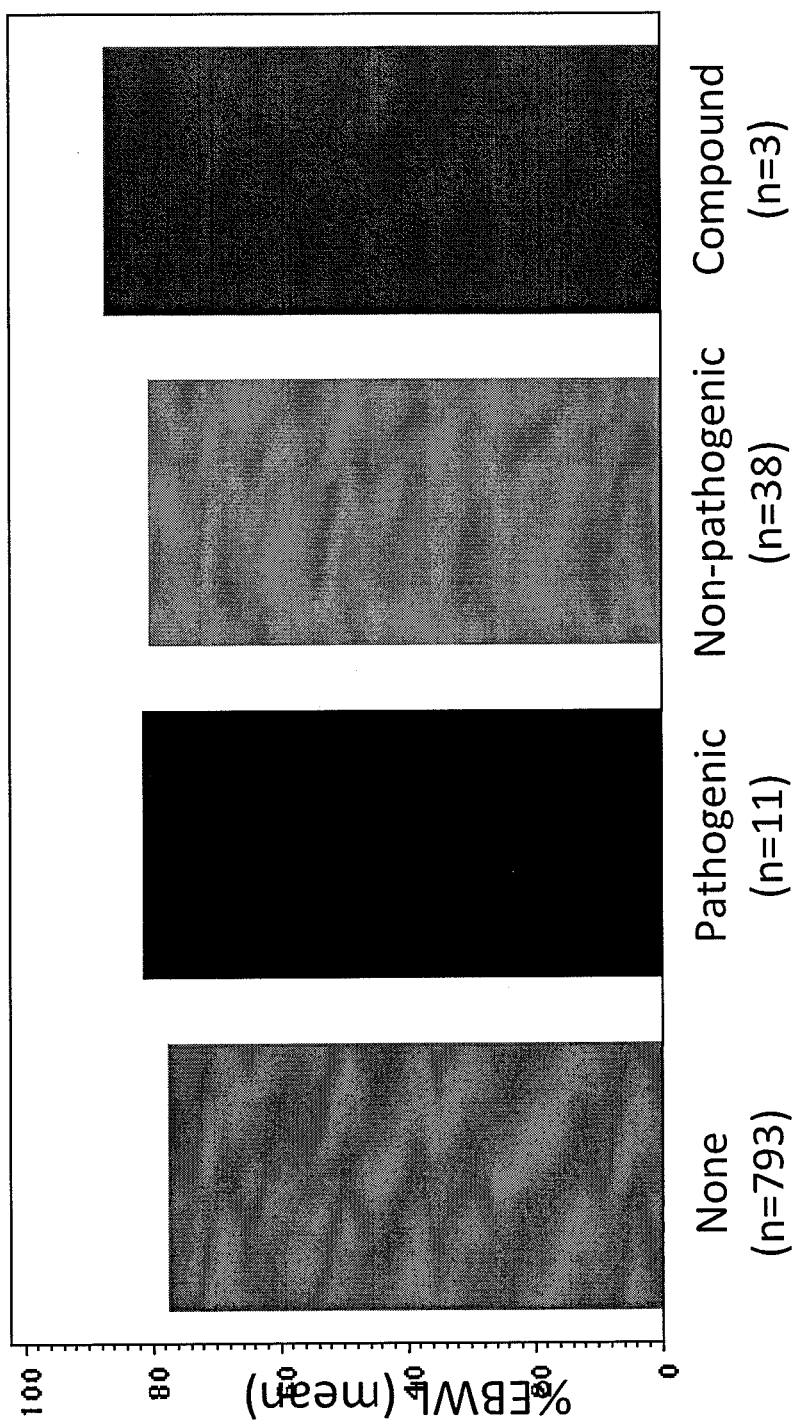
FIG. 24 compares excess body weight loss (EBWL) after RYGB surgical intervention in the four groups of patients.
Figure 25:
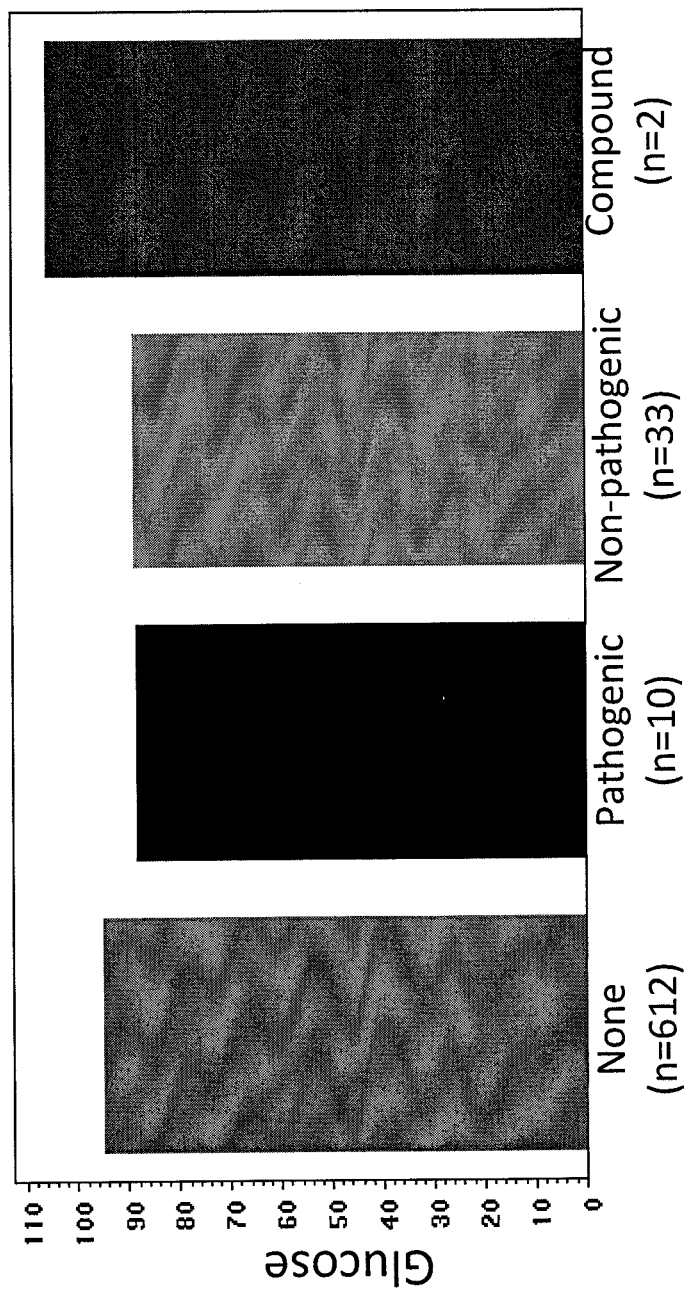
FIG. 25 shows glucose homeostasis in the four groups of patients after RYGB surgical intervention.

FIG. 23 shows that while heterozygous MC4R mutations are associated with metabolic parameters prior to RYGB surgical intervention, the heterozygous mutations have little impact on weight change or excess body weight loss (EBWL) (FIG. 24) after RYGB surgical intervention. Moreover, glucose homeostasis is similar among the groups after RYGB surgical intervention, FIG. 25.

One skilled in the art will appreciate further features and advantages of the invention based on the above-described embodiments. Accordingly, the invention is not to be limited by what has been particularly shown and described in the examples or figures, except as indicated by the appended claims. All publications and references cited herein are expressly incorporated herein by reference in their entirety.

What is claimed is:

1. A method of activating a melanocortin-4 receptor (MC4R) pathway in an obese subject, the method comprising:
   (a) performing a first intervention on a subject, wherein the first intervention is a non-surgical procedure;
   (b) measuring energy expenditure of the subject to measure MC4R pathway activation in response to the first intervention; and
   (c) performing a second intervention that activates the melanocortin receptor pathway, wherein the second intervention is chosen based on the measured energy expenditure and appropriate for the subject to increase energy expenditure, and wherein the first intervention is different from the second intervention.

2. The method of claim 1, wherein the first intervention is a temporary procedure.

3. The method of claim 1, wherein the first intervention is at least one selected from the group consisting of a melanocortin-4 receptor agonist therapy, activation of brown adipose tissue and a duodenal endoluminal barrier.

4. The method of claim 1, wherein the second intervention is at least one selected from the group consisting of melanocortin-4 receptor agonist therapy, activation of brown adipose tissue, gastric bypass, biliopancreatic diversion, vertical sleeve gastrectomy, adjustable gastric banding, vertical banded gastroplasty, intragastric balloon therapy, gastric plication, Magenstrasse and Mill, small bowel transposition, biliary diversion and duodenal endoluminal barrier.

5. The method of claim 1, wherein the first intervention is continued in combination with the second intervention.

6. The method of claim 1, wherein the second intervention activates the melanocortin receptor pathway in at least one cell in region selected from the group consisting of the brain, spinal cord, sympathetic nervous system, parasympathetic nervous system, enteric nervous system, gastrointestinal tract and pancreas.

7. The method of claim 1, wherein the method comprises inducing weight loss, altered energy balance or altered metabolic function in the subject.

8. A method of activating a melanocortin-4 receptor pathway in an obese subject, the method comprising:
   (a) performing a first intervention on a subject, wherein the first intervention is a non-surgical procedure; and;
   (b) performing a second intervention that is distinct from the first intervention to increase energy expenditure and activate the melanocortin receptor pathway.

9. The method of claim 8, wherein the first intervention is a temporary procedure.

10. The method of claim 8, wherein the first intervention is selected from the group consisting of a melanocortin-4 receptor agonist therapy and activation of brown adipose tissue.

11. The method of claim 8, further comprises measuring melanocortin receptor pathway activation.

12. The method of claim 11, wherein the step of measuring melanocortin receptor pathway activation comprises detecting markers of melanocortin receptor activation.

13. The method of claim 8, further comprises measuring energy expenditure.

14. The method of claim 8, wherein the second intervention is at least one selected from the group consisting of melanocortin-4 receptor agonist therapy, activation of brown adipose tissue, gastric bypass, biliopancreatic diversion, vertical sleeve gastrectomy, adjustable gastric banding, vertical banded gastroplasty, intragastric balloon therapy, gastric plication, Magenstrasse and Mill, small bowel transposition, biliary diversion and duodenal endoluminal barrier.

15. The method of claim 8, wherein the method comprises inducing weight loss in the subject.

16. The method of claim 8, wherein the second intervention activates the melanocortin receptor pathway in at least one cell in region selected from the group consisting of the brain, spinal cord, sympathetic nervous system, parasympathetic nervous system, enteric nervous system, gastrointestinal tract and a pancreas.

17. A method of activating a melanocortin-4 receptor pathway to induce weight loss in an obese subject, the method comprising:
   (a) performing a first intervention on a subject to affect the MC4R pathway;
   (b) performing a second intervention to increase energy expenditure and activate the MC4R pathway to induce weight loss, and wherein the first intervention is different from the second intervention.

18. A method of activating a melanocortin-4 receptor pathway to induce weight loss in an obese subject, comprising:
   (a) performing a first intervention on a subject to affect the MC4R pathway; and
   (b) performing a bariatric surgery to increase energy expenditure and activate the MC4R pathway to induce weight loss, and wherein the first intervention is different from the second intervention.

19. The method of claim 18, wherein the first intervention does not involve the administration to the subject of a therapeutic agent effective to activate the MC4R pathway.

20. The method of claim 18, wherein the bariatric surgery activates brown adipose tissue.

* * * * *

SEQUENCE LISTING

<160> NUMBER OF SEQ ID NOS: 6

<210> SEQ ID NO 1
<211> LENGTH: 3115
<212> TYPE: DNA
<213> ORGANISM: Homo sapiens

```
<400> SEQUENCE: 1
agacgcagtc ttcagcaagg aagtgctggg aacgccctgg agtgaaccca ggaagatgcc      60
tgcagtgggt gccagggccc ctctccaccg tccctgctgg gcttcggggc cacgcccgac     120
tgctgtgaac ggcctgcgga gcaccacgtg cgacggctgg aggcgagagg tctgcctttg     180
atgtggctgt tggtgcaggg cctgtggtgc cttccgcagc ggaaatggcg cgccgcccgg     240
ggagggcggg agcagcgtcc cgggtgcccc tgtgaggatg agcgacgaga tgactggagg     300
gtccctgaag acctcactag ggtgcccca gccggtccgc tcccaggaag cgacaccccc      360
acagccccag ggctgcagct gaggggtcg ccactctggc tgggcgaggc tgggcccttg      420
ggggcaggcg ccagagtggc ctcaggctct acaagatgcc tgaaaacacc aacctctcca     480
gggctcacta gcattggacg cttttcacgct ctgcctggc cggaagcccc ctcaccccgc     540
gcgatgtgca aactcctgca gggctcactc agtttccaga actttaatta ttggaaagtt     600
ctccctggtc cagcccccaa atctgccgtg aacgttgaca gctgagttgc tgctccatgc     660
gtgctttggc tgagagcaga ggggaccccct gtcctccctg agctgctgac gaggggaggg     720
gtgaagggtg gggcctctgg agagggcagg tcccggggaa gctccggact cctagagggg     780
cggccaggtg ggggccctgg tgaccaggac agactgtggt gtttttttaac gtaaaggaga     840 tccgcggtgt gagggacccc ctgggtcctg cacgccgcct ggtggcaggc cgggccatgg     900
tgggtgctca cgcccccggc atgtggccgc cctcagtggg aggggctctg agaacgactt     960
tttaaaacgc agagaaaagc tccattcttc ccaggacctc agcgcagccc tggcccagga    1020
aggcaggaga cagaggccag gacggtccag aggtgtcgaa atgtcctggg gacctgagca    1080
gcagccacca gggaagaggc agggaggag ctgaggacca ggcttggttg tgagaatccc     1140
tgagcccagg cggtagatgc caggaggtgt ctggactggc tgggccatgc ctgggctgac    1200
ctgtccagcc agggagaggg tgtgagggca gatctggggg tgcccagatg aaggaggca    1260 ggcatggggg acacccaagg cccctggca gcaccatgaa ctaagcagga cacctggagg     1320
ggaagaactg tggggacctg gaggcctcca acgactcctt cctgcttcct ggacaggact    1380
atggctgtgc agggatccca gagaagactt ctgggctccc tcaactccac ccccacagcc    1440 atccccagc tggggctggc tgccaaccag acaggagccc ggtgcctgga ggtgtccatc     1500
tctgacgggc tcttcctcag cctggggctg gtgagcttgg tggagaacgc gctggtggtg    1560
gccaccatcg ccaagaaccg gaacctgcac tcacccatgt actgcttcat ctgctgcctg    1620
gccttgtcgg acctgctggt gagcgggagc aacgtgctgg agacggccgt catcctcctg    1680
ctggaggccg gtgcactggt ggcccgggct gcggtgctgc agcagctgga caatgtcatt    1740
gacgtgatca cctgcagctc catgctgtcc agcctctgct tcctgggcgc catcgccgtg    1800
gaccgctaca tctccatctt ctacgcactg cgctaccaca gcatcgtgac cctgccgcgg    1860
gcgcggcgag ccgttgcggc catctgggtg ccagtgtcg tcttcagcac gctcttcatc     1920
gcctactacg accacgtggc cgtcctgctg tgcctcgtgg tcttcttcct ggctatgctg    1980
gtgctcatgg ccgtgctgta cgtccacatg ctggcccggg cctgccagca cgcccagggc    2040
atcgcccggc tccacaagag gcagcgcccg gtccaccagg gctttggcct taaaggcgct    2100 gtcacccctca ccatcctgct gggcattttc ttcctctgct ggggcccctt cttcctgcat    2160
ctcacactca tcgtcctctg ccccgagcac cccacgtgcg gctgcatctt caagaacttc    2220
aacctctttc tcgccctcat catctgcaat gccatcatcg accccctcat ctacgccttc    2280
cacagccagg agctccgcag gacgctcaag gaggtgctga catgctcctg gtgagcgcgg    2340
```

-continued

| | |
|---|---|
| tgcacgcggc tttaagtgtg ctgggcagag ggaggtggtg atattgtgtg gtctggttcc | 2400 |
| tgtgtgaccc tgggcagttc cttacctccc tggtccccgt tgtcaaaga ggatggacta | 2460 |
| aatgatctct gaaagtgttg aagcgcggac ccttctgggt ccagggaggg gtccctgcaa | 2520 |
| aactccaggc aggacttctc accagcagtc gtggggaacg gaggaggaca tggggaggtt | 2580 |
| gtggggcctc aggctccggg caccaggggc caacctcagg ctcctaaaga gacattttcc | 2640 |
| gcccactcct gggacactcc gtctgctcca atgactgagc agcatccacc ccaccccatc | 2700 |
| tttgctgcca gctctcagga ccgtgccctc gtcagctggg atgtgaagtc tctgggtgga | 2760 |
| agtgtgtgcc aagagctact cccacagcag ccccaggaga aggggctttg tgaccagaaa | 2820 |
| gcttcatcca cagccttgca gcggctcctg caaaaggagg tgaaatccct gcctcaggcc | 2880 |
| aagggaccag gtttgcagga gccccctag tggtatgggg ctgagccctc ctgagggccg | 2940 |
| gttctaaggc tcagactggg cactggggcc tcagcctgct ttcctgcagc agtcgcccaa | 3000 |
| gcagacagcc ctggcaaatg cctgactcag tgaccagtgc ctgtgagcat ggggccagga | 3060 |
| aagtctggta ataaatgtga ctcagcatca cccaccttaa aaaaaaaaa aaaaa | 3115 |

<210> SEQ ID NO 2
<211> LENGTH: 3652
<212> TYPE: DNA
<213> ORGANISM: Homo sapiens

<400> SEQUENCE: 2

| | |
|---|---|
| attccttctc attcattttg cccagaaagt tcctgcttca gagctgaagg tgattgggag | 60 |
| attttaactt agatctccag caagtgctac aaggaagaaa agatcctgaa gaatcaatca | 120 |
| agttttccgt gaagtcaagt ccaagtaaca tccccgcctt aaccacaagc aggagaaatg | 180 |
| aagcacatta tcaactcgta tgaaaacatc aacaacacag caagaaataa ttccgactgt | 240 |
| cctcgtgtgg ttttgccgga ggagatattt ttcacaattt ccattgttgg agttttggag | 300 |
| aatctgatcg tcctgctggc tgtgttcaag aataagaatc tccaggcacc catgtacttt | 360 |
| ttcatctgta gcttggccat atctgatatg ctgggcagcc tatataagat cttggaaaat | 420 |
| atcctgatca tattgagaaa catgggctat ctcaagccac gtggcagttt tgaaaccaca | 480 |
| gccgatgaca tcatcgactc cctgtttgtc ctctccctgc ttggctccat cttcagcctg | 540 |
| tctgtgattg ctgcgaccg ctacatcacc atcttccacg cactgcggta ccacagcatc | 600 |
| gtgaccatgc gccgcactgt ggtggtgctt acggtcatct ggacgttctg cacggggact | 660 |
| ggcatcacca tggtgatctt ctcccatcat gtgcccacag tgatcacctt cacgtcgctg | 720 |
| ttcccgctga tgctggtctt catcctgtgc ctctatgtgc acatgttcct gctggctcga | 780 |
| tcccacacca ggaagatctc cacccctccc agagccaaca tgaaagggc catcacactg | 840 |
| accatcctgc tcggggtctt catcttctgc tgggcccct tgtgcttca tgtcctcttg | 900 |
| atgacattct gccaagtaa cccctactgc gcctgctaca tgtctctctt ccaggtgaac | 960 |
| ggcatgttga tcatgtgcaa tgccgtcatt gacccttca tatatgcctt ccggagccca | 1020 |
| gagctcaggg acgcattcaa aaagatgatc ttctgcagca ggtactggta gaatggctga | 1080 |
| tccctggttt tagaatccat gggaataacg ttgccaagtg ccagaatagt gtaacattcc | 1140 |
| aacaaatgcc agtgctcctc actggccttc cttccctaat ggatgcaagg atgatcccac | 1200 |
| cagctagtgt ttctaatagc taggttctat gtgaacagtc ttattgtagg ggcaacctct | 1260 |
| taactttgtg actggacaga taaaacgatg tagtaaaaga aggatagaat acaaagtatt | 1320 |
| aggtaggtac aaaagtaatt aaggtttttg ccattacttt caatgaccaa aaattgcaat | 1380 |

```
tacttttgca ccaatctagt aaaacagcaa taaaaattca agggctttgg gctaaggcaa    1440
agacttgctt tcctgtggac atctaacaag ccagttctga ggtggccttt ccaggtggag    1500
gccattgcag ccaatttcca gaagttaagt acctggacat gcgactccag gcagaagatg    1560
tagggtctct gtaagccaat aataaattgg aaggaatgca ttgctgcagc tgaatttgtc    1620
tgtctcccac agccatgtgg aatctccacc ctcctctttc tccctgttag tctgatgtat    1680
tgatgccacc tcagtttcag aaagtaggct gagtataaac tataaatgtc aaataacgag    1740
cttcgagttt ccaatgataa atggaccttc tctgttagtc ttctttgctc actcagtatc    1800
ccactggcct taaacccctt tcctgttaca tttcctcatg ctttatgagc atacatttca    1860
aaggaagaaa tgaaaattta atccatttag ttcccatgtg ggaatacata aaggccagat    1920
gaaaattgtc actatttgaa gaagctgtaa ccaaactatg tgtgttacaa tgtagaagta    1980
caagaaaaga gccccaacat gtattttaag aaataaagag agagagacag agacagacag    2040
agagagagag agagagagag agagagagtg tgtgtgtgtg tgtgtgtgtg tgtgtgtgtg    2100
tgtgtgtgtg tgtgtgtgta ttttcccat gcttttggac tatgggaaa accaaaacca      2160
aagcaagaca tcaagcaatg gtgctgttat tatagcccca agtcaaagac ctgagggagg    2220
caaacaccac ctcattctgc agatgaatgt gaaagcagac ccagtcactg ggaaatgtca    2280
tcctcccatc agccaagatg ccagcaatgg aagagtggca accccagtag gaataaaaga    2340
aacataattt gcaagttcat tcatttttaa tagctaaaaa tcagcttaaa ggagaagcac    2400
atcctgattg taagtcccca ctaagttgga gggtgacttg aatggggtga aggtgaaag     2460
ggacagagga gagcagtggg gcttcagagg ccaccaggct caggatctgc aggatggatg    2520
gtatcttcca gaacaggcaa tgcttttgccc tcaggagaat ttcccagagc tgctgagggg   2580
agaagacagc cacacacagg acagaccatt tggtgatggg tttgatatta gaagtggcag    2640
ggacaggaac ttcagaagca aaggaggcaa ggcagctgga gtcaagtgag gacagtggca    2700
ggcgtgcttt cacatggcct gtcccacaga tggaggtgaa aggtgcacct tcttgtcctc    2760
tgttctgtag aaatccttcc ctgtttgatc cttcccctgc caaatgaact atgttactct    2820
aatactaacc tgtattaatt aatatatgag atatatataa gttaattttt catgaaatct    2880
aaagcacaac cctagaacta atttttaaaa gtgttatttc taccattgaa aaagtaatgt    2940
ataacatatt ttatgtgatt aaagtgcgta ttctcaataa gaggtaaacct ttttttgatg   3000
ctgcaatgct ctgtgatacc acagaggtaa gcaatgccac ttaacctgta tcataaatag    3060
tcccaaactc ctcttcctat aaaattctgc ctttgtcaac agctttgctg tctcctaatc    3120
actctcaagc tctctgctgt gcatgtgact gttgtcagaa ggaaaatcac caagaaactt    3180
cacctctcac tgcctttgat ttgttgcagt taatctaaga aacaaaatga agatggctag    3240
tctaatggtg gatgaaacaa aaatgaagtc tgagtgctaa ttcagagaac ttgcaattcc    3300
agacattttc aattctaggt cttctgctat attccaatca gaacagaagc ttcagggctc    3360
atagttactg agaaaaactca cgttttttcta cctctaactt catatagaat tccaaatgaa   3420
agcaccacca aactgcacat atttgtgtga ggaagatcaa caagcttcag acttttccca    3480
tgaggactta attctttttat caaattaccc aattttttaaa ctgctgtgtg gatactgtga   3540
gtgttcagct ttatcgatga cctagccttg gaccagatag ctgaaaatgt tcaggatgtg    3600
tactcaagct gatagtaatt ctgagccctg tctaataaaa aaggaaggat gt             3652
```

<210> SEQ ID NO 3
<211> LENGTH: 1084
<212> TYPE: DNA

<213> ORGANISM: Homo sapiens

<400> SEQUENCE: 3

```
aatgagcatc caaaagacgt atctggaggg agattttgtc tttcctgtga gcagcagcag    60
cttcctacgg accctgctgg agccccagct cggatcagcc cttctgacag caatgaatgc   120
ttcgtgctgc ctgccctctg ttcagccaac actgcctaat ggctcggagc acctccaagc   180
cccttctttc agcaaccaga gcagcagcgc cttctgtgag caggtcttca tcaagcccga   240
ggttttcctg tctctgggca tcgtcagtct gctggaaaac atcctggtta tcctggccgt   300
ggtcaggaac ggcaacctgc actccccgat gtacttcttt ctctgcagcc tggcggtggc   360
cgacatgctg gtaagtgtgt ccaatgccct ggagaccatc atgatcgcca tcgtccacag   420
cgactacctg accttcgagg accagtttat ccagcacatg gacaacatct tcgactccat   480
gatctgcatc tccctggtgg cctccatctg caacctcctg gccatcgccg tcgacaggta   540
cgtcaccatc ttttacgcgc tccgctacca cagcatcatg accgtgagga aggccctcac   600
cttgatcgtg gccatctggg tctgctgcgg cgtctgtggc gtggtgttca tcgtctactc   660
ggagagcaaa atggtcattg tgtgcctcat caccatgttc ttcgccatga tgctcctcat   720
gggcacccte tacgtgcaca tgttcctctt tgcgcggctg cacgtcaagc gcatagcagc   780
actgccacct gccgacgggg tggccccaca gcaacactca tgcatgaagg gggcagtcac   840
catcaccatt ctcctgggcg tgttcatctt ctgctgggcc cccttcttcc tccacctggt   900
cctcatcatc acctgcccca ccaacccta ctgcatctgc tacactgccc acttcaacac   960
ctacctggtc ctcatcatgt gcaactccgt catcgaccca ctcatctacg ctttccggag  1020
cctggaattg cgcaacacct tagggagat tctctgtggc tgcaacggca tgaacttggg  1080
atag                                                              1084
```

<210> SEQ ID NO 4
<211> LENGTH: 1319
<212> TYPE: DNA
<213> ORGANISM: Homo sapiens

<400> SEQUENCE: 4

```
catagggaga ccctgtctct taaaaaaaaa aaaaaaaaag gactgagtga gccgagccca    60
gtcctctgat gcactgtgtc attcatcccc tttcttaggc tgtgttggtt ctaggctagc   120
tgctgtcttt cttttggtagg ctgctaacct ctttggattg tgaatttaaa acatgtttta   180
cagtaaattt gctgccaaga caagaggtgt atttctccag caatgaattc ctcatttcac   240
ctgcatttct tggatctcaa cctgaatgcc acagagggca accttcagg acccaatgtc   300
aaaaacaagt cttcaccatg tgaagacatg ggcattgctg tggaggtgtt tctcactctg   360
ggtgtcatca gcctcttgga aacatcttg tcatagggg ccatagtgaa gaacaaaaac   420
ctgcactccc ccatgtactt cttcgtgtgc agcctggcag tggcggacat gctggtgagc   480
atgtccagtg cctgggagac catcaccatc tacctactca caacaagca cctagtgata   540
gcagacgcct ttgtgcgcca cattgacaat gtgtttgact ccatgatctg catttccgtg   600
gtggcatcca tgtgcagctt actggccatt gcagtggata ggtacgtcac catcttctac   660
gccctgcgct accaccacat catgacgcg aggcgctcag gggccatcat cgccggcatc   720
tgggcttttct gcacgggctg cggcattgtc ttcatcctgt actcagaatc cacctacgtc   780
atcctgtgcc tcatctccat gttcttcgct atgctgttcc tcctggtgtc tctgtacata   840
cacatgttcc tcctggcgcg gactcacgtc aagcggatcg cggctctgcc cggggccagc   900
```

-continued

```
tctgcgcggc agaggaccag catgcagggc gcggtcaccg tcaccatgct gctgggcgtg      960
tttaccgtgt gctgggcccc gttcttcctt catctcactt taatgctttc ttgccctcag     1020
aacctctact gctctcgctt catgtctcac ttcaatatgt acctcatact catcatgtgt     1080
aattccgtga tggaccctct catatatgcc ttccgcagcc aagagatgcg gaagaccttt     1140
aaggagatta tttgctgccg tggtttcagg atcgcctgca gctttcccag aagggattaa     1200
gcacaaagtg ctcctctctg tggctctgtt tcctttgtt tgctcaccta tgacaaagcg      1260
acagccaagg ggtaggcggg agtgctagca tcccattttt ctctttacca gctcagaca     1319
```

<210> SEQ ID NO 5
<211> LENGTH: 1438
<212> TYPE: DNA
<213> ORGANISM: Homo sapiens

<400> SEQUENCE: 5

```
aaagcaacgc tcaggctgga aacagaagct tccgagaggc agccgatgtg agcatgtgcg       60
cacagattcg tctcccaatg gcatggcagc ttcaaggaaa attattttga acagacttga      120
atgcataaga ttaaagttaa agcagaagtg agaacaagaa agcaaagagc agactctttc      180
aactgagaat gaatattttg aagcccaaga ttttaaagtg atgatgatta gagtcgtacc      240
taaaagagac taaaaactcc atgtcaagct ctggacttgt gacatttact cacagcaggc      300
atggcaattt tagcctcaca actttcagac agataaagac ttggaggaaa taactgagac      360
gactccctga cccaggaggt taaatcaatt caggggggaca ctggaattct cctgccagca     420
tggtgaactc cacccaccgt gggatgcaca cttctctgca cctctggaac cgcagcagtt      480
acagactgca cagcaatgcc agtgagtccc ttggaaaagg ctactctgat ggagggtgct      540
acgagcaact ttttgtctct cctgaggtgt ttgtgactct gggtgtcatc agcttgttgg      600
agaatatctt agtgattgtg gcaatagcca agaacaagaa tctgcattca cccatgtact      660
ttttcatctg cagcttggct gtggctgata tgctggtgag cgtttcaaat ggatcagaaa      720
ccattgtcat caccctatta aacagtacag atacggatgc acagagtttc acagtgaata      780
ttgataatgt cattgactcg gtgatctgta gctccttgct tgcatccatt tgcagcctgc      840
tttcaattgc agtggacagg tactttacta tcttctatgc tctccagtac cataacatta      900
tgacagttaa gcgggttggg atcatcataa gttgtatctg ggcagcttgc acggtttcag      960
gcattttgtt catcattac tcagatagta gtgctgtcat catctgcctc atcaccatgt      1020
tcttcaccat gctggctctc atggcttctc tctatgtcca catgttcctg atggccaggc     1080
ttcacattaa gaggattgct gtcctccccg gcactggtgc catccgccaa ggtgccaata     1140
tgaagggagc gattaccttg accatcctga ttggcgtctt tgttgtctgc tgggccccat     1200
tcttcctcca cttaatattc tacatctctt gtcctcagaa tccatattgt gtgtgcttca     1260
tgtctcactt taacttgtat ctcatactga tcatgtgtaa ttcaatcatc gatcctctga     1320
tttatgcact ccggagtcaa gaactgagga aaaccttcaa agagatcatc tgttgctatc     1380
ccctgggagg cctttgtgac ttgtctagca gatattaaat ggggacagag cacgcaat      1438
```

<210> SEQ ID NO 6
<211> LENGTH: 332
<212> TYPE: PRT
<213> ORGANISM: Homo sapiens

<400> SEQUENCE: 6

```
Met Val Asn Ser Thr His Arg Gly Met His Thr Ser Leu His Leu Trp
1               5                   10                  15
```

```
Asn Arg Ser Ser Tyr Arg Leu His Ser Asn Ala Ser Glu Ser Leu Gly
            20                  25                  30

Lys Gly Tyr Ser Asp Gly Gly Cys Tyr Glu Gln Leu Phe Val Ser Pro
        35                  40                  45

Glu Val Phe Val Thr Leu Gly Val Ile Ser Leu Leu Glu Asn Ile Leu
        50                  55                  60

Val Ile Val Ala Ile Ala Lys Asn Lys Asn Leu His Ser Pro Met Tyr
65                  70                  75                  80

Phe Phe Ile Cys Ser Leu Ala Val Ala Asp Met Leu Val Ser Val Ser
            85                  90                  95

Asn Gly Ser Glu Thr Ile Val Ile Thr Leu Leu Asn Ser Thr Asp Thr
            100                 105                 110

Asp Ala Gln Ser Phe Thr Val Asn Ile Asp Asn Val Ile Asp Ser Val
            115                 120                 125

Ile Cys Ser Ser Leu Leu Ala Ser Ile Cys Ser Leu Leu Ser Ile Ala
130                 135                 140

Val Asp Arg Tyr Phe Thr Ile Phe Tyr Ala Leu Gln Tyr His Asn Ile
145                 150                 155                 160

Met Thr Val Lys Arg Val Gly Ile Ile Ile Ser Cys Ile Trp Ala Ala
                165                 170                 175

Cys Thr Val Ser Gly Ile Leu Phe Ile Ile Tyr Ser Asp Ser Ser Ala
            180                 185                 190

Val Ile Ile Cys Leu Ile Thr Met Phe Phe Thr Met Leu Ala Leu Met
        195                 200                 205

Ala Ser Leu Tyr Val His Met Phe Leu Met Ala Arg Leu His Ile Lys
        210                 215                 220

Arg Ile Ala Val Leu Pro Gly Thr Gly Ala Ile Arg Gln Gly Ala Asn
225                 230                 235                 240

Met Lys Gly Ala Ile Thr Leu Thr Ile Leu Ile Gly Val Phe Val Val
                245                 250                 255

Cys Trp Ala Pro Phe Phe Leu His Leu Ile Phe Tyr Ile Ser Cys Pro
            260                 265                 270

Gln Asn Pro Tyr Cys Val Cys Phe Met Ser His Phe Asn Leu Tyr Leu
        275                 280                 285

Ile Leu Ile Met Cys Asn Ser Ile Ile Asp Pro Leu Ile Tyr Ala Leu
        290                 295                 300

Arg Ser Gln Glu Leu Arg Lys Thr Phe Lys Glu Ile Ile Cys Cys Tyr
305                 310                 315                 320

Pro Leu Gly Gly Leu Cys Asp Leu Ser Ser Arg Tyr
                325                 330
```